United States Patent
Iijima et al.

(10) Patent No.: US 10,711,091 B2
(45) Date of Patent: Jul. 14, 2020

(54) LIGHT-EMITTING DEVICE AND METHOD FOR PRODUCING SAME

(71) Applicants: Sumitomo Chemical Company, Limited, Tokyo (JP); Cambridge Display Technology Limited, Cambridgeshire (GB)

(72) Inventors: Takayuki Iijima, Tsukuba (JP); Satoshi Kobayashi, Tsukuba (JP); Masanobu Tanaka, Tsukuba (JP); Nobuhiko Akino, Tsukuba (JP); Sheena Zuberi, Cambridgeshire (GB)

(73) Assignees: SUMITOMO CHEMICAL COMPANY, LIMITED, Tokyo (JP); Cambridge Display Technology Limited, Cambridgeshire (GB)

( * ) Notice: Subject to any disclaimer, the term of this patent is extended or adjusted under 35 U.S.C. 154(b) by 0 days.

(21) Appl. No.: 16/089,464

(22) PCT Filed: Mar. 21, 2017

(86) PCT No.: PCT/JP2017/011173
§ 371 (c)(1),
(2) Date: Sep. 28, 2018

(87) PCT Pub. No.: WO2017/169972
PCT Pub. Date: Oct. 5, 2017

(65) Prior Publication Data
US 2019/0048131 A1 Feb. 14, 2019

(30) Foreign Application Priority Data
Mar. 29, 2016 (JP) .................... 2016-066107

(51) Int. Cl.
| | |
|---|---|
| H01L 51/50 | (2006.01) |
| C08G 61/10 | (2006.01) |
| H05B 33/10 | (2006.01) |
| H01L 51/00 | (2006.01) |
| C07D 235/18 | (2006.01) |

(52) U.S. Cl.
CPC ............ *C08G 61/10* (2013.01); *H01L 51/002* (2013.01); *H01L 51/005* (2013.01); *H01L 51/5076* (2013.01); *H05B 33/10* (2013.01); *C07D 235/18* (2013.01); *H01L 51/5016* (2013.01); *H01L 2251/552* (2013.01)

(58) Field of Classification Search
None
See application file for complete search history.

(56) References Cited

U.S. PATENT DOCUMENTS

| | | | |
|---|---|---|---|
| 2010/0187515 | A1 | 7/2010 | Limmert et al. |
| 2011/0108772 | A1 | 5/2011 | Zeika et al. |
| 2014/0070178 | A1 | 3/2014 | Lee et al. |
| 2017/0033286 | A1 | 2/2017 | Kugler et al. |

FOREIGN PATENT DOCUMENTS

| | | | |
|---|---|---|---|
| JP | 2007-273978 A | | 10/2007 |
| JP | 2009-530836 A | | 8/2009 |
| JP | 2010-532555 A | | 10/2010 |
| JP | 2016-041670 A | | 3/2016 |
| JP | 2017-033929 A | | 2/2017 |

OTHER PUBLICATIONS

Int'l Preliminary Report on Patentability dated Oct. 2, 2018 in Int'l Application No. PCT/JP2017/011173.
Zhengyang et al., "Efficient n-type dopants with extremely low doping ratios for high performance inverted perovskite solar cells", Energy & Environmental Science, vol. 9, No. 11, 2016.
Search Report dated Nov. 16, 2018 in EP Application No. 17774513.0.
Bao et al, "Use of a 1H-Benzoimidazole Derivative as an n-Type Dopant and To Enable Air-Stable Solution-Processed n-Channel Organic Thin-Film Transistors," Journal of the American Chemical Society, vol. 132, No. 26, pp. 8852-8853 (2010).
Int'l Search Report dated Jun. 20, 2017 in Int'l Application No. PCT/JP2017/011173.
Wei et al, "2-(2-Methoxyphenyl)-1,3-dimethyl-1H-benzoimidazol-3-ium Iodide as a New Air-Stable n-Type Dopant for Vacuum-Processed Organic Semiconductor Thin Films," Journal of the American Chemical Society, vol. 134, No. 9, pp. 3999-4002 (Mar. 7, 2012).
Naab et al, "Mechanistic Study on the Solution-Phase n-Doping of 1,3-Dimethyl-2-aryl-2,3-dihydro-1H-benzoimidazole Derivatives," Journal of the American Chemical Society, vol. 135, No. 40, pp. 15018-15025 (Oct. 9, 2013).
Bin et al, "Air Stable Organic Salt As an n-Type Dopant for Efficient and Stable Organic Light-Emitting Diodes," Applied Materials & Interfaces, vol. 7, pp. 6444-6450 (Mar. 13, 2015).
Office Action dated May 20, 2019 in CN Application No. 201780020282.3.

*Primary Examiner* — Gregory D Clark
(74) *Attorney, Agent, or Firm* — Panitch Schwarze Belisario & Nadel LLP

(57) ABSTRACT

Provided is a light-emitting device including an anode, a light-emitting layer, an electron-transporting layer and a cathode. The electron-transporting layer contains at least one electron-transporting material whose LUMO level is −3.0 eV or more and at least one dopant material selected from the group consisting of a heterocyclic compound whose SOMO level is −2.2 to −1.5 eV and a derivative thereof. The LUMO level of the electron-transporting material is smaller than the SOMO level of the heterocyclic compound.

7 Claims, No Drawings

LIGHT-EMITTING DEVICE AND METHOD FOR PRODUCING SAME

CROSS-REFERENCE TO RELATED APPLICATION

This application is a Section 371 of International Application No. PCT/JP2017/011173, filed Mar. 21, 2017, which was published in the Japanese language on Oct. 5, 2017, under International Publication No. WO 2017/169972 A1, which claims priority to Japanese Patent Application No. 2016-066107, filed on Mar. 29, 2016, the disclosures of which are incorporated herein by reference in their entireties.

TECHNICAL FIELD

The present invention relates to a light-emitting device and a method for producing the same.

BACKGROUND ART

In recent years, research on various electronic devices such as organic light-emitting diodes (OLED), polymer light-emitting diodes (PLED), organic photovoltaics (OPV), and organic thin film transistors (OTFT) using ultrathin films of organic matter has been actively made. For these electronic devices, methods using doping materials are known as methods for improving conductivity.

For example, an organic thin film transistor using N-DMBI as a n-type doping material is disclosed in Non Patent Literature 1; an organic light-emitting diode using N-DMBI as a n-type doping material is disclosed in Patent Literature 1; and a n-type dopant precursor for doping an organic semiconductor material is disclosed in Patent Literature 2.

CITATION LIST

Patent Literature

Patent Literature 1: U.S. Patent Application Publication No. 2010/0070178
Patent Literature 2: Japanese Unexamined Patent Publication No. 2010-532555

Non Patent Literature

Non Patent Literature 1: Bao et al., "Use of a 1H-Benzoimidazole Derivative as an n-Type Dopant and To Enable Air-Stable Solution-Processed n-Channel Organic Thin-Film Transistors" J. Am. Chem. Soc. 2010, 132, 8852

SUMMARY OF INVENTION

Technical Problem

However, sufficient findings on stable n-type doping materials that permit film formation by a coating method have not yet been obtained. For example, compounds described in n-type doping materials in the cited literatures mentioned above did not always have sufficient electron-donating ability.

Accordingly, an object of the present invention is to provide a light-emitting device using a strong n-type doping material, and a method for producing the same.

Solution to Problem

The present invention provides the following [1] to [10]:

[1] A light-emitting device comprising an anode, a light-emitting layer, an electron-transporting layer and a cathode, the electron-transporting layer containing at least one electron-transporting material whose LUMO level is −3.0 eV or more and at least one dopant material selected from the group consisting of a heterocyclic compound whose SOMO level is −2.2 to −1.5 eV and a derivative thereof, wherein the LUMO level of the electron-transporting material is smaller than the SOMO level of the heterocyclic compound.

[2] The light-emitting device according to [1], wherein the electron-transporting layer and the cathode are adjacent.

[3] The light-emitting device according to [1] or [2], wherein a content of the dopant material in the electron-transporting layer is 1 to 50 parts by mass with respect to 100 parts by mass of the electron-transporting material.

[4] The light-emitting device according to any of [1] to [3], wherein the light-emitting layer comprises a phosphorescent material.

[5] The light-emitting device according to any of [1] to [4], wherein
the heterocyclic compound is a compound represented by the formula (1-A), and
the derivative is a compound represented by the formula (1-B) or the formula (1-C):

[Chemical Formula 1]

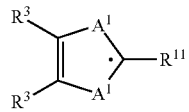

(1-A)

[Chemical Formula 2]

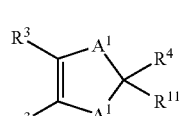

(1-B)

[Chemical Formula 3]

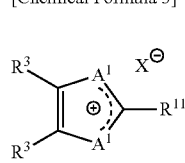

(1-C)

wherein
$A^1$ represents an oxygen atom, a sulfur atom, —$NR^5$— or —$PR^5$—; two $A^1$ are the same as or different from each other, and at least one $A^1$ is —$NR^5$— or —$PR^5$—;
$R^3$ represents a hydrogen atom, an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; —$CH_2$— in these groups is optionally substituted by an oxygen atom, a sulfur atom, —$NR^5$— or —C(=O)O—, and a portion or the whole of hydrogen atoms in these groups is optionally replaced with a halogen atom, provided that adjacent two —$CH_2$— are not substituted at the same time; two $R^3$ are the same or different and are optionally bonded to each other to form a ring, and a substituent is optionally bonded onto the ring;

$R^4$ represents a hydrogen atom, —C($R^6$)$_3$, —N($R^7$)$_2$ or —Si($R^7$)$_3$; —CH$_2$— in these groups is optionally substituted by an oxygen atom, a sulfur atom, —NR$^5$— or —C(=O)O—, and a portion or the whole of hydrogen atoms in these groups is optionally replaced with a halogen atom, provided that adjacent two —CH$_2$— are not substituted at the same time;

$R^5$ represents an alkyl group, a cycloalkyl group, an aryl group or a monovalent heterocyclic group; —CH$_2$— in these groups is optionally substituted by an oxygen atom, a sulfur atom, —NR$^8$— or and a portion or the whole of hydrogen atoms in these groups is optionally replaced with a halogen atom, provided that adjacent two —CH$_2$— are not substituted at the same time; when a plurality of $R^5$ are present, the plurality of $R^5$ are the same as or different from each other;

$R^6$ represents a hydrogen atom, an alkyl group, a cycloalkyl group, an aryl group or a monovalent heterocyclic group; a portion or the whole of hydrogen atoms in these groups is optionally replaced with a halogen atom; a plurality of $R^6$ are the same as or different from each other; two $R^6$ are optionally bonded to form a ring;

$R^7$ represents an alkyl group, a cycloalkyl group, an aryl group or a monovalent heterocyclic group; a portion or the whole of hydrogen atoms in these groups is optionally replaced with a halogen atom; a plurality of $R^7$ are the same as or different from each other; two $R^7$ are optionally bonded to form a ring;

$R^8$ represents an alkyl group, a cycloalkyl group, an aryl group or a monovalent heterocyclic group; a portion or the whole of hydrogen atoms in these groups is optionally replaced with a halogen atom; when a plurality of $R^8$ are present, the plurality of $R^8$ are the same as or different from each other;

$R^{11}$ represents an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group or a disubstituted amino group; —CH$_2$— in these groups is optionally substituted by an oxygen atom, a sulfur atom, —NR$^5$— or —C(=O)O—, and a portion or the whole of hydrogen atoms in these groups is optionally replaced with a halogen atom, provided that adjacent two —CH$_2$— are not substituted at the same time; and $X^-$ represents a counter anion for the cation.

[6] The light-emitting device according to [5], wherein the heterocyclic compound is a compound represented by the formula (2-A), and the derivative is a compound represented by the formula (2-B) or the formula (2-C):

[Chemical Formula 4]

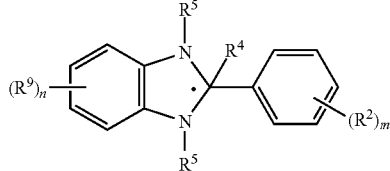

(2-A)

[Chemical Formula 5]

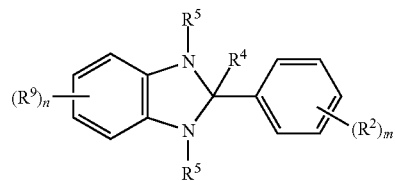

(2-B)

[Chemical Formula 6]

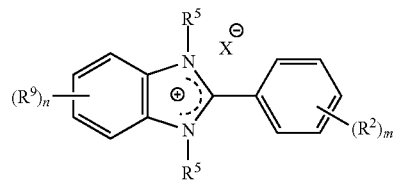

(2-C)

wherein $R^4$, $R^5$ and $X^-$ are the same as above;

$R^2$ represents an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; —CH$_2$— in these groups is optionally substituted by an oxygen atom, a sulfur atom, —NR$^5$— or —C(=O)O—, and a portion or the whole of hydrogen atoms in these groups is optionally replaced with a halogen atom, provided that adjacent two —CH$_2$— are not substituted at the same time; in the case where m is 2 or larger, a plurality of $R^2$ are the same as or different from each other; adjacent $R^2$ are optionally bonded to each other to form a ring;

$R^9$ represents an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; —CH$_2$— in these groups is optionally substituted by an oxygen atom, a sulfur atom, —NR$^5$— or —C(=O)O—, and a portion or the whole of hydrogen atoms in these groups is optionally replaced with a halogen atom, provided that adjacent two —CH$_2$— are not substituted at the same time; in the case where n is 2 or larger, a plurality of $R^9$ are the same as or different from each other; adjacent $R^9$ are optionally bonded to each other to form a ring;

m represents an integer of 0 to 5;

n represents an integer of 0 to 4; and m+n is 2 or larger.

[7] The light-emitting device according to any of [1] to [6], wherein the electron-transporting material comprises a polymer compound having a constitutional unit represented by the formula (ET-1):

[Chemical Formula 7]

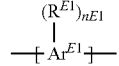

(ET-1)

wherein nE1 represents an integer of 1 or larger;

$Ar^{E1}$ represents an aromatic hydrocarbon group or a heterocyclic group, and these groups optionally have a substituent other than $R^{E1}$;

$R^{E1}$ represents an alkyl group, a cycloalkyl group, an aryl group, an alkoxy group, a cycloalkoxy group, an aryloxy group, a monovalent heterocyclic group, or a group represented by $-R^{E2}(-X^1)_{m1}$; when a plurality of $R^{E1}$ are present, the plurality of $R^{E1}$ are the same as or different from each other;

$X^1$ represents a monovalent group containing a heteroatom; when a plurality of $X^1$ are present, the plurality of $X^1$ are the same as or different from each other;

$R^{E2}$ represents a direct bond or an (m1+1)-valent group; and m1 represents an integer of 1 or larger.

[8] The light-emitting device according to any of [1] to [6], wherein the electron-transporting material comprises a compound represented by the formula (H-1):

[Chemical Formula 8]

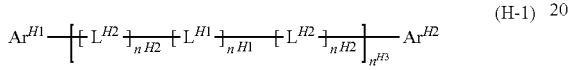

(H-1)

wherein $Ar^{H1}$, $Ar^{H2}$ and $L^{H1}$ each represent an aromatic hydrocarbon group or a heterocyclic group;

$L^{H2}$ represents a group represented by $-N(-L^{H21}-R^{H21})-$;

$L^{H21}$ represents a single bond, an arylene group or a divalent heterocyclic group, and these groups optionally have a substituent;

$R^{H21}$ represents a hydrogen atom, an alkyl group, a cycloalkyl group, an aryl group or a monovalent heterocyclic group, and these groups optionally have a substituent;

when a plurality of $L^{H1}$ are present, the plurality of $L^{H1}$ are the same as or different from each other; when a plurality of $L^{H2}$ are present, the plurality of $L^{H2}$ are the same as or different from each other; and $n^{H1}$, $n^{H2}$ and $n^{H3}$ represent an integer of 0 or larger.

[9] A method for producing an electron-transporting layer, comprising a step of doping an electron-transporting material whose LUMO level is −3.0 eV or more with a heterocyclic compound whose SOMO level is −2.2 to −1.5 eV, wherein the LUMO level of the electron-transporting material is smaller than the SOMO level of the heterocyclic compound.

[10] A method for producing a light-emitting device having an anode, a light-emitting layer, an electron-transporting layer and a cathode, comprising:

a step of providing a composition containing at least one electron-transporting material whose LUMO level is −3.0 eV or more and at least one dopant material selected from the group consisting of a heterocyclic compound whose SOMO level is −2.2 to −1.5 eV and a derivative thereof; and a step of forming a film of the composition by a coating method to form the electron-transporting layer, wherein the LUMO level of the electron-transporting material is smaller than the SOMO level of the heterocyclic compound.

Advantageous Effects of Invention

The light-emitting device according to the present invention employs a strong n-type doping material and emits light with a high luminance. Also, the light-emitting device according to the present invention can be easily produced using a coating method because the n-type doping material is relatively stable in a solvent.

DESCRIPTION OF EMBODIMENTS

Hereinafter, preferable embodiments of the present invention will be described in detail.

Description of Common Terms

The terms commonly used in the present specification have the following meanings unless otherwise specified.

Me represents a methyl group, Et represents an ethyl group, Bu represents a butyl group, i-Pr represents an isopropyl group, t-Bu represents a tert-butyl group, and Ph represents a phenyl group.

The hydrogen atom may be a heavy hydrogen atom or may be a light hydrogen atom.

In a formula that represents a metal complex, a solid line that represents a bond to a central metal means a covalent bond or a coordinate bond.

The "polymer compound" means a polymer that has a molecular weight distribution and has a polystyrene-equivalent number-average molecular weight of $1\times10^3$ or larger (e.g., $1\times10^3$ to $1\times10^8$). The polymer compound may be any of a block copolymer, a random copolymer, an alternate copolymer, and a graft copolymer, or may be in other forms.

The terminal group of the polymer compound is preferably a stable group because there is a possibility that if a polymerization active group remains as it is, light-emitting characteristics or luminance lifetime is reduced in the case of using the polymer compound in the preparation of a light-emitting device. This terminal group is preferably a group covalently bonded to the backbone, and examples include a group bonded to an aryl group or a monovalent heterocyclic group via a carbon-carbon bond.

The "constitutional unit" means one or more units present in a polymer compound.

The "low-molecular compound" means a compound that does not have a molecular weight distribution and has a molecular weight of $1\times10^4$ or smaller.

The "alkyl group" may be linear or branched. The number of carbon atoms of the linear alkyl group is usually 1 to 50, preferably 1 to 10, more preferably 1 to 6, which excludes the number of carbon atoms of a substituent. The number of carbon atoms of the branched alkyl group is usually 3 to 50, preferably 3 to 30, more preferably 4 to 20, which excludes the number of carbon atoms of a substituent.

The alkyl group optionally has a substituent. Examples of the alkyl group include a methyl group, an ethyl group, a propyl group, an isopropyl group, a butyl group, a 2-butyl group, an isobutyl group, a tert-butyl group, a pentyl group, an isoamyl group, a 2-ethylbutyl group, a hexyl group, a heptyl group, an octyl group, a 2-ethylhexyl group, a 3-propylheptyl group, a decyl group, a 3,7-dimethyloctyl group, a 2-ethyloctyl group, a 2-hexyldecyl group, and a dodecyl group. Alternatively, the alkyl group may be a group in which a portion or the whole of hydrogen atoms in these groups is replaced with a cycloalkyl group, an alkoxy group, a cycloalkoxy group, an aryl group, a fluorine atom or the like. Examples of such alkyl group include a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-di-hexylphenyl)propyl group, and a 6-ethyloxyhexyl group.

The number of carbon atoms of the "cycloalkyl group" is usually 3 to 50, preferably 3 to 30, more preferably 4 to 20, which excludes the number of carbon atoms of a substituent.

The cycloalkyl group optionally has a substituent. Examples of the cycloalkyl group include a cyclohexyl group, a cyclohexylmethyl group, and a cyclohexylethyl group.

The "aryl group" means a remaining atomic group excluding one hydrogen atom directly bonded to an annular carbon atom from an aromatic hydrocarbon. The number of carbon atoms of the aryl group is usually 6 to 60, preferably 6 to 20, more preferably 6 to 10, which excludes the number of carbon atoms of a substituent.

The aryl group optionally has a substituent. Examples of the aryl group include a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group, and a 4-phenylphenyl group. Alternatively, the aryl group may be a group in which a portion or the whole of hydrogen atoms in these groups is replaced with an alkyl group, a cycloalkyl group, an alkoxy group, a cycloalkoxy group, an aryl group, a fluorine atom or the like.

The "alkoxy group" may be linear or branched. The number of carbon atoms of the linear alkoxy group is usually 1 to 40, preferably 1 to 6, which excludes the number of carbon atoms of a substituent. The number of carbon atoms of the branched alkoxy group is usually 3 to 40, preferably 4 to 10, which excludes the number of carbon atoms of a substituent.

The alkoxy group optionally has a substituent. Examples of the alkoxy group include a methoxy group, an ethoxy group, a propyloxy group, an isopropyloxy group, a butyloxy group, an isobutyloxy group, a tert-butyloxy group, a pentyloxy group, a hexyloxy group, a heptyloxy group, an octyloxy group, a 2-ethylhexyloxy group, a nonyloxy group, a decyloxy group, a 3,7-dimethyloctyloxy group, and a lauryloxy group. Alternatively, the alkoxy group may be a group in which a portion or the whole of hydrogen atoms in these groups is replaced with a cycloalkyl group, an alkoxy group, a cycloalkoxy group, an aryl group, a fluorine atom or the like.

The number of carbon atoms of the "cycloalkoxy group" is usually 3 to 40, preferably 4 to 10, which excludes the number of carbon atoms of a substituent.

The cycloalkoxy group optionally has a substituent. Example of the cycloalkoxy group includes a cyclohexyloxy group.

The number of carbon atoms of the "aryloxy group" is usually 6 to 60, preferably 6 to 48, which excludes the number of carbon atoms of a substituent.

The aryloxy group optionally has a substituent. Examples of the aryloxy group include a phenoxy group, a 1-naphthyloxy group, a 2-naphthyloxy group, a 1-anthracenyloxy group, a 9-anthracenyloxy group, and a 1-pyrenyloxy group. Alternatively, the aryloxy group may be a group in which a portion or the whole of hydrogen atoms in these groups is replaced with an alkyl group, a cycloalkyl group, an alkoxy group, a cycloalkoxy group, a fluorine atom or the like.

The "alkylsulfenyl group" may be linear or branched. The number of carbon atoms of the linear alkylsulfenyl group is usually 1 to 40, preferably 4 to 10, which excludes the number of carbon atoms of a substituent. The number of carbon atoms of the branched alkylsulfenyl group is usually 3 to 40, preferably 4 to 10, which excludes the number of carbon atoms of a substituent.

The alkylsulfenyl group optionally has a substituent. Examples of the alkylsulfenyl group include a methylsulfenyl group, an ethylsulfenyl group, a propylsulfenyl group, an isopropylsulfenyl group, a butylsulfenyl group, an isobutylsulfenyl group, a tert-butylsulfenyl group, a pentylsulfenyl group, a hexylsulfenyl group, a heptylsulfenyl group, an octylsulfenyl group, a 2-ethylhexylsulfenyl group, a nonylsulfenyl group, a decylsulfenyl group, a 3,7-dimethyloctylsulfenyl group, and a laurylsulfenyl group. Alternatively, the alkylsulfenyl group may be a group in which a portion or the whole of hydrogen atoms in these groups is replaced with a cycloalkyl group, an alkoxy group, a cycloalkoxy group, an aryl group, a fluorine atom or the like.

The number of carbon atoms of the "cycloalkylsulfenyl group" is usually 3 to 40, preferably 4 to 10, which excludes the number of carbon atoms of a substituent.

The cycloalkylsulfenyl group optionally has a substituent. Examples of the cycloalkylsulfenyl group include a cyclohexylsulfenyl group.

The number of carbon atoms of the "arylsulfenyl group" is usually 6 to 60, preferably 7 to 48, which excludes the number of carbon atoms of a substituent.

The arylsulfenyl group optionally has a substituent. Examples of the arylsulfenyl group include a phenylsulfenyl group, a 1-naphthylsulfenyl group, a 2-naphthylsulfenyl group, a 1-anthracenylsulfenyl group, a 9-anthracenylsulfenyl group, and a 1-pyrenylsulfenyl group. Alternatively, the arylsulfenyl group may be a group in which a portion or the whole of hydrogen atoms in these groups is replaced with an alkyl group, a cycloalkyl group, an alkoxy group, a cycloalkoxy group, a fluorine atom or the like.

The "p-valent heterocyclic group" (p represents an integer of 1 or larger) means a remaining atomic group excluding p hydrogen atom(s) among hydrogen atoms directly bonded to annular carbon atoms or heteroatoms from a heterocyclic compound. Among the p-valent heterocyclic groups, a "p-valent aromatic heterocyclic group" is preferable which is a remaining atomic group excluding p hydrogen atom(s) among hydrogen atoms directly bonded to annular carbon atoms or heteroatoms from an aromatic heterocyclic compound.

The "aromatic heterocyclic compound" means a compound in which a heterocyclic ring itself exhibits aromaticity, such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, or dibenzophosphole, and a compound in which an aromatic ring is condensed with a heterocyclic ring even though the heterocyclic ring itself does not aromaticity, such as phenoxazine, phenothiazine, dibenzoborole, dibenzosilole, or benzopyran.

The number of carbon atoms of the p-valent heterocyclic group is usually 2 to 60, preferably 3 to 20, more preferably 4 to 20, which excludes the number of carbon atoms of a substituent.

The p-valent heterocyclic group optionally has a substituent. Among the p-valent heterocyclic group, examples of the monovalent heterocyclic group include a thienyl group, a pyrrolyl group, a furyl group, a pyridyl group, a piperidinyl group, a quinolinyl group, an isoquinolinyl group, a pyrimidinyl group, and a triazinyl group. Alternatively, the monovalent heterocyclic group may be a group in which a portion or the whole of hydrogen atoms in the these groups is replaced with an alkyl group, a cycloalkyl group, an alkoxy group, a cycloalkoxy group or the like.

The "halogen atom" refers to a fluorine atom, a chlorine atom, a bromine atom or an iodine atom.

The "amino group" optionally has a substituent, and a substituted amino group is preferable. An alkyl group, a cycloalkyl group, an aryl group or a monovalent heterocyclic group is preferable as the substituent carried by the amino group.

A disubstituted amino group is preferable as the substituted amino group. Examples of the disubstituted amino group include a dialkylamino group, a dicycloalkylamino group and a diarylamino group. The substituents of the disubstituted amino group are optionally bonded to each other to form a ring. The number of carbon atoms of the alkyl group as the substituent of the disubstituted amino group is preferably 1 to 10, more preferably 1 to 6, further preferably 1 to 4.

Examples of the disubstituted amino group include a dimethylamino group, a diethylamino group, a diphenylamino group, a bis(4-methylphenyl)amino group, a bis(4-tert-butylphenyl)amino group, and a bis(3,5-di-tert-butylphenyl)amino group.

The "alkenyl group" may be linear or branched. The number of carbon atoms of the linear alkenyl group is usually 2 to 30, preferably 3 to 20, which excludes the number of carbon atoms of a substituent. The number of carbon atoms of the branched alkenyl group is usually 3 to 30, preferably 4 to 20, which excludes the number of carbon atoms of a substituent.

The number of carbon atoms of the "cycloalkenyl group" is usually 3 to 30, preferably 4 to 20, which excludes the number of carbon atoms of a substituent.

The alkenyl group and the cycloalkenyl group optionally have a substituent. Examples of the alkenyl group include a vinyl group, a 1-propenyl group, a 2-propenyl group, a 2-butenyl group, a 3-butenyl group, a 3-pentenyl group, a 4-pentenyl group, a 1-hexenyl group, a 5-hexenyl group, a 7-octenyl group, and groups in which a portion or the whole of hydrogen atoms in these groups is replaced with a substituent.

The "alkynyl group" may be linear or branched. The number of carbon atoms of the alkynyl group is usually 2 to 20, preferably 3 to 20, which excludes the carbon atoms of a substituent. The number of carbon atoms of the branched alkynyl group is usually 4 to 30, preferably 4 to 20, which excludes the carbon atoms of a substituent.

The number of carbon atoms of the "cycloalkynyl group" is usually 4 to 30, preferably 4 to 20, which excludes the carbon atoms of a substituent.

The alkynyl group and the cycloalkynyl group optionally have a substituent. Examples of the alkynyl group include an ethynyl group, a 1-propynyl group, a 2-propynyl group, a 2-butynyl group, a 3-butyryl group, a 3-pentynyl group, a 4-pentynyl group, a 1-hexynyl group, a 5-hexynyl group, and groups in which a portion or the whole of hydrogen atoms in these groups is replaced with a substituent.

The "arylene group" means a remaining atomic group excluding two hydrogen atoms directly bonded to annular carbon atoms from an aromatic hydrocarbon. The number of carbon atoms of the arylene group is usually 6 to 60, preferably 6 to 30, more preferably 6 to 18, which excludes the number of carbon atoms of a substituent.

The arylene group optionally has a substituent. Examples of the arylene group include a phenylene group, a naphthalenediyl group, an anthracenediyl group, a phenanthrenediyl group, a dihydrophenanthrenediyl group, a naphthacenediyl group, a fluorenediyl group, a pyrenediyl group, a perylenediyl group, a chrysenediyl group, and groups in which a portion or the whole of hydrogen atoms in these groups is replaced with a substituent. The arylene group is preferably groups represented by the formula (A-1) to the formula (A-20). The arylene group includes groups in which a plurality of these groups are bonded.

[Chemical Formula 9]

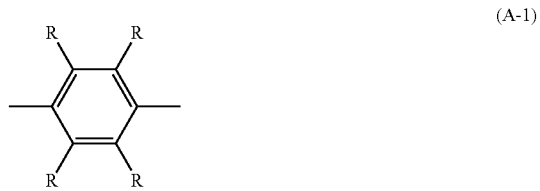

(A-1)

(A-2)

(A-3)

(A-4)

(A-5)

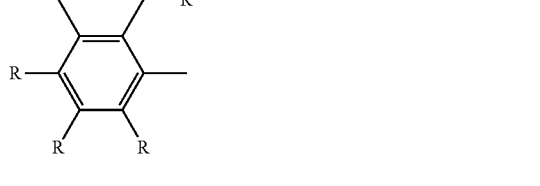

(A-6)

[Chemical Formula 10]
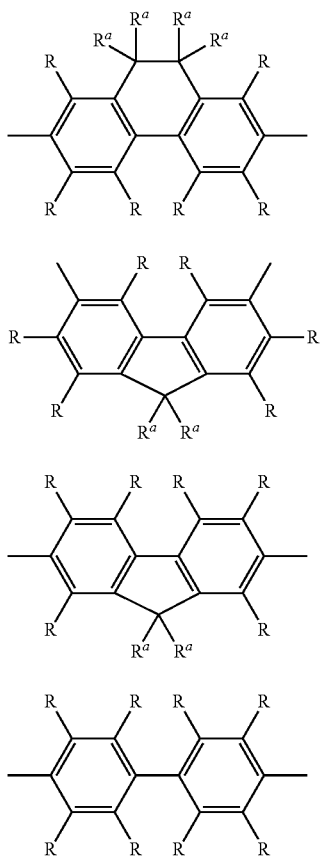
(A-7)
(A-8)
(A-9)
(A-10)
[Chemical Formula 11]
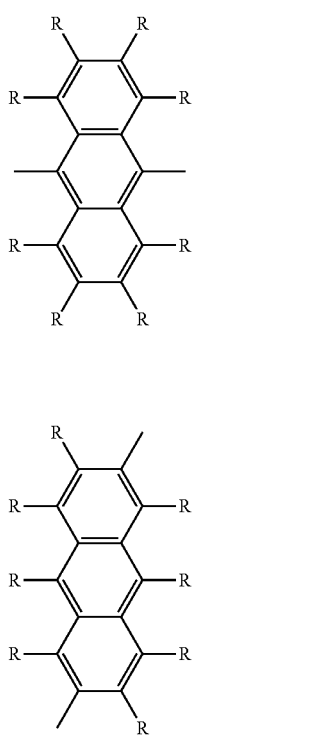
(A-11)
(A-12)
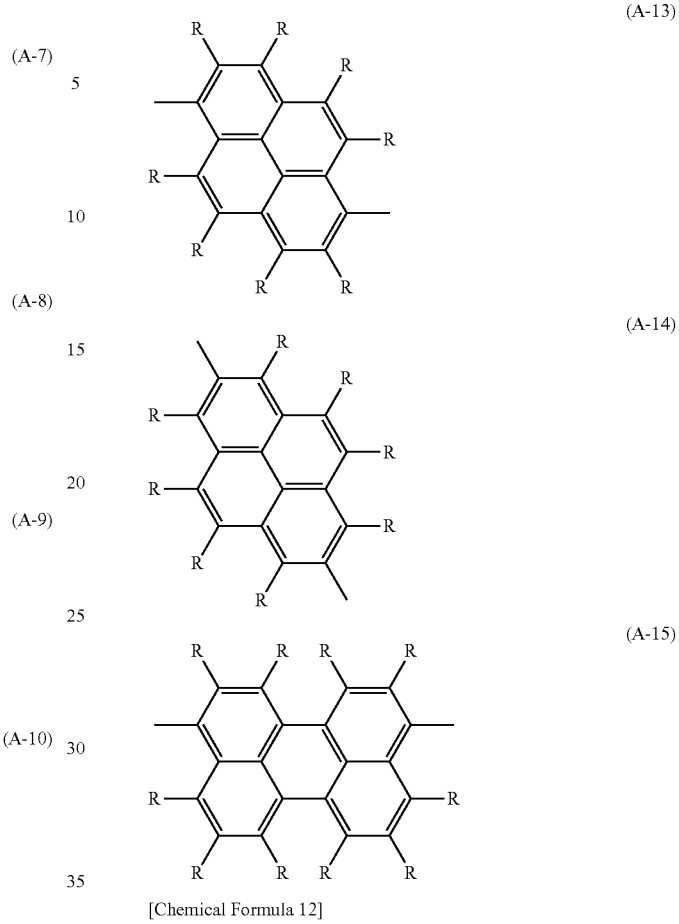
(A-13)
(A-14)
(A-15)
[Chemical Formula 12]
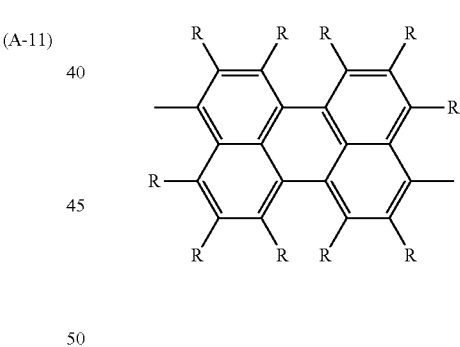
(A-16)
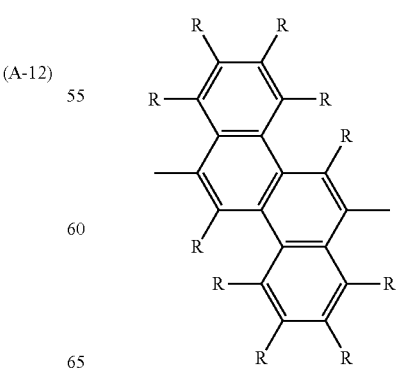
(A-17)

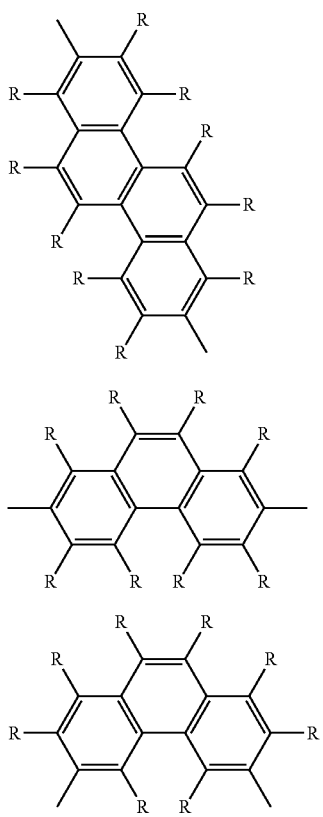

(A-18)

(A-19)

(A-20)

In the formulas, R and $R^a$ each independently represent a hydrogen atom, an alkyl group, a cycloalkyl group, an aryl group or a monovalent heterocyclic group. Pluralities of R and $R^a$ present are respectively the same or different, and a plurality of $R^a$ are optionally bonded to each other to form a ring together with the atoms to which they are attached.

The number of carbon atoms of the divalent heterocyclic group is usually 2 to 60, preferably 3 to 20, more preferably 4 to 15, which excludes the number of carbon atoms of a substituent.

The divalent heterocyclic group optionally has a substituent. Examples of the divalent heterocyclic group include divalent groups excluding two hydrogen atoms among hydrogen atoms directly bonded to annular carbon atoms or heteroatoms from pyridine, diazabenzene, triazine, azanaphthalene, diazanaphthalene, carbazole, dibenzofuran, dibenzothiophene, dibenzosilole, phenoxazine, phenothiazine, acridine, dihydroacridine, furan, thiophene, azole, diazole, or triazole. The divalent heterocyclic group is preferably groups represented by the formula (AA-1) to the formula (AA-34). The divalent heterocyclic group includes groups in which a plurality of these groups are bonded.

[Chemical Formula 13]

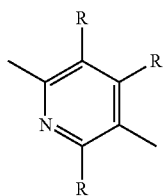

(AA-1)

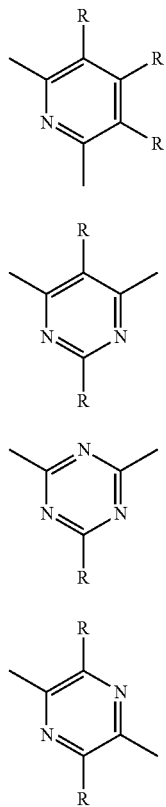

(AA-2)

(AA-3)

(AA-4)

(AA-5)

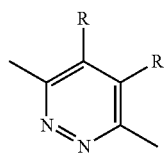

(AA-6)

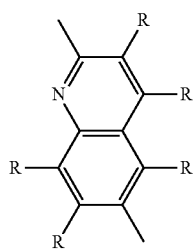

(AA-7)

[Chemical Formula 14]

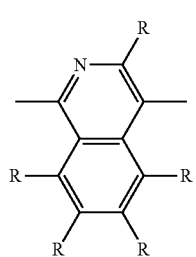

(AA-8)

[Chemical Formula 15]

(AA-9), (AA-10), (AA-11), (AA-12), (AA-13), (AA-14), (AA-15)

[Chemical Formula 16]

(AA-16), (AA-17), (AA-18), (AA-19), (AA-20)

[Chemical Formula 17]

(AA-21), (AA-22)

(AA-23) 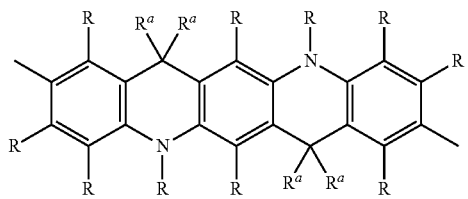

(AA-24) 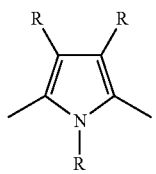

[Chemical Formula 18]

(AA-25) 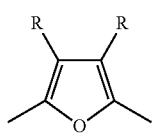

(AA-26) 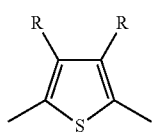

(AA-27) 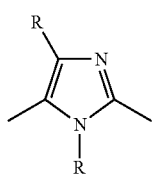

(AA-28) 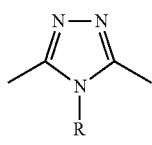

(AA-29) 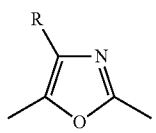

(AA-30) 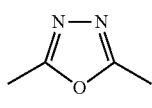

(AA-31) 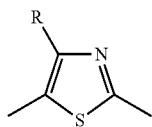

(AA-32) 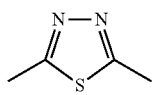

[Chemical Formula 19]

(AA-33) 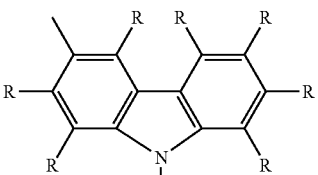

(AA-34) 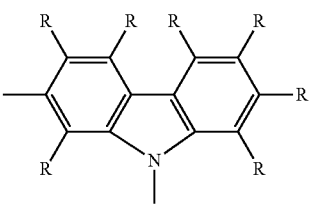

In the formulas, R and $R^a$ represent the same meanings as above.

The "cross-linking group" is a group capable of being subjected to heating, ultraviolet irradiation, near-ultraviolet irradiation, visible light irradiation, infrared irradiation, radical reaction or the like and thereby forming a new bond. The cross-linking group is preferably a group represented by any of the formulas (B-1) to (B-17). These groups optionally have a substituent.

[Chemical Formula 20]

(B-1) 

(B-2) 

(B-3) 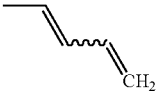

(B-4) 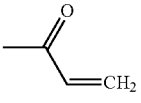

(B-5) 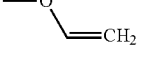

(B-6) 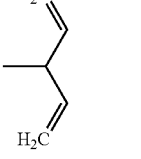

(B-7) 

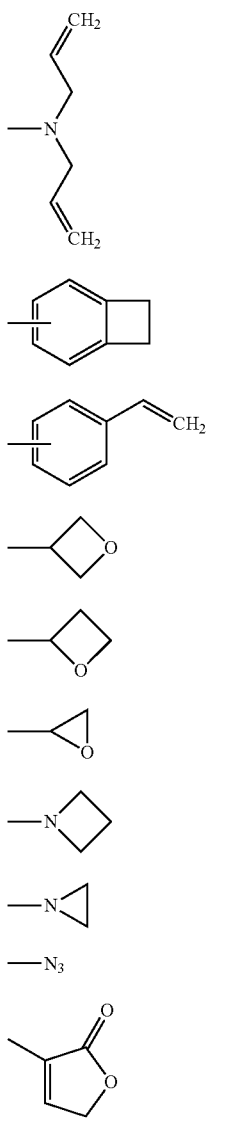

The "substituent" represents a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group or a cycloalkynyl group. The substituent may be a cross-linking group.

<Light-Emitting Device>

The light-emitting device according to the present embodiment has an anode, a light-emitting layer, an electron-transporting layer and a cathode. In the light-emitting device according to the present embodiment, the electron-transporting layer contains at least one electron-transporting material whose LUMO (lowest unoccupied molecular orbital) level is −3.0 eV or more and at least one dopant material selected from the group consisting of a heterocyclic compound whose SOMO (singly occupied molecular orbital) level is −2.2 to −1.5 eV and a derivative thereof. Also, the LUMO level of the electron-transporting material is smaller than the SOMO level of the heterocyclic compound.

Hereinafter, each factor carried by the light-emitting device according to the present embodiment will be described in detail.

<Electron-Transporting Layer>

In the present embodiment, the dopant material contained in the electron-transporting layer is selected from the group consisting of a heterocyclic compound whose SOMO level is −2.2 to −1.5 eV, and a derivative of the heterocyclic compound. The heterocyclic compound can also be interpreted as an organic compound having a heterocyclic ring.

The SOMO level of the heterocyclic compound employs a quantum-chemical calculation program Gaussian 09, and the structure optimization of a radical state of the heterocyclic compound can be performed by a density functional method at the B3LYP level using MIDI! as a basis to determine the SOMO level in the optimized structure.

The upper limit of the SOMO level is preferably −1.5 eV, more preferably −1.8 eV, and the lower limit of the SOMO level is preferably −1.9 eV, more preferably −2.0 eV, because of being excellent in the stability of the dopant.

The derivative of the heterocyclic compound can be a compound that is converted to the heterocyclic compound by activation by heat or light irradiation, etc., or a compound that is formed from the heterocyclic compound by electron donation to the electron-transporting material. For example, when the heterocyclic compound having the predetermined SOMO level is a radical form, the derivative of the heterocyclic compound can be a compound that is converted to the radical form by heat or light irradiation, or a cation form that is formed by removing one electron from the radical form.

It is preferable that the heterocyclic compound should be a compound represented by the formula (1-A).

[Chemical Formula 21]

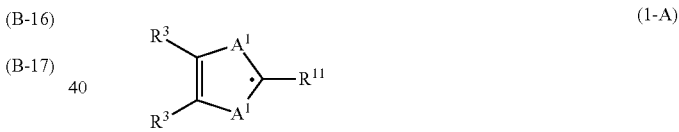

Also, it is preferable that the derivative of the heterocyclic compound should be a compound represented by the formula (1-B) or the formula (1-C).

[Chemical Formula 22]

[Chemical Formula 23]

It is preferable for $A^1$ that both of two $A^1$ should be —$NR^5$— or —$PR^5$—, and it is more preferable that both of two $A^1$ should be —$NR^5$—.

It is more preferable that the heterocyclic compound should be a compound represented by the formula (2-A).

[Chemical Formula 24]

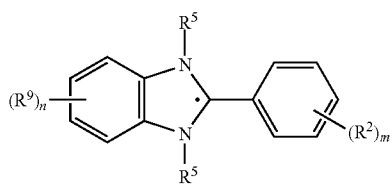

(2-A)

Also, it is more preferable that the derivative of the heterocyclic compound should be a compound represented by the formula (1-B) or the formula (1-C).

[Chemical Formula 25]

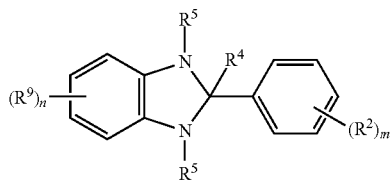

(2-B)

[Chemical Formula 26]

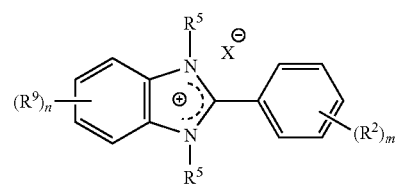

(2-C)

Specific examples of the heterocyclic compound and the SOMO levels thereof are shown in Table 1 and Table 2. However, in the present invention, the heterocyclic compound is not limited to those described below.

TABLE 1

| Compound name | Structural formula | SOMO level (eV) |
|---|---|---|
| DP1 | [structure: tetrahydropyrazino-fused benzimidazole with N-Me groups, 2-aryl substituent bearing two NMe$_2$ groups] | −2.05 |
| DP2 | [structure: 5,6-bis(dimethylamino)-1,3-dimethyl-2-(4-dimethylaminophenyl)benzimidazole] | −2.19 |
| DP3 | [structure: bis-benzimidazole fused system with two 4-NMe$_2$-phenyl substituents and N-Me groups] | −2.06 |
| DP4 | [structure: 5,6-bis(dimethylamino)-1,3-dimethyl-2-(2,6-dimethoxy-4-dimethylaminophenyl)benzimidazole] | −1.76 |

TABLE 1-continued

| Compound name | Structural formula | SOMO level (eV) |
|---|---|---|
| DP5 | (benzimidazole with N-Me groups connected to 2,6-dimethoxy-4-(NEt₂)phenyl) | −1.81 |
| DP6 | (benzimidazole with N-Me groups connected to 2,6-dimethoxy-4-(NMe₂)phenyl) | −1.88 |

TABLE 2

| Compound name | Structural formula | SOMO level (eV) |
|---|---|---|
| DP7 | (N,N-dimethylbenzimidazole connected to 2,6-bis(NMe₂)-4-(NMe₂)phenyl) | −2.05 |
| DP8 | (benzimidazole with N-CH₂CH₂OMe groups connected to 2,6-dimethoxy-4-(OCH₂CH₂OMe)phenyl) | −2.05 |
| DP9 | (N,N-dimethylimidazole connected to 2,6-dimethoxy-4-(NMe₂)phenyl) | −1.66 |

TABLE 2-continued

| Compound name | Structural formula | SOMO level (eV) |
|---|---|---|
| DP10 | | −1.62 |
| DP11 | | −1.80 |

For reference, publicly known compounds and the SOMO levels thereof are shown in Table 3.

TABLE 3

| Compound name | Structural formula | SOMO level (eV) |
|---|---|---|
| Publicly known compound 1 N-DMBI radical | | −2.31 |
| Publicly known compound 2 DP12 | | −2.75 |

In the present embodiment, the LUMO level of the electron-transporting material contained in the electron-transporting layer is lower than the SOMO level of the heterocyclic compound and is −3.0 eV or more. The LUMO level of the electron-transporting material is usually −2.0 eV or less.

The electron-transporting material is classified into a polymer compound and a low-molecular compound. In the present embodiment, the electron-transporting material may be a polymer compound or may be a low-molecular compound, and it is preferable to be an aromatic compound. The electron-transporting material can have a cross-linking group and may be cross-linked by a cross-linking group.

In the case where the electron-transporting material is a polymer compound, examples include polyphenylene, poly- fluorene, and their derivatives. Also, a polymer compound having a constitutional unit represented by the formula (ET-1) is preferable as the electron-transporting material.

[Chemical Formula 27]

Examples of the (m1+1)-valent group represented by $R^{E2}$ include a remaining atomic group excluding m1 hydrogen atom(s) from a hydrocarbyl group or a monovalent heterocyclic group, and the atomic group optionally has a substituent. Examples of $R^{E2}$ also include a group represented by the formula —O—(R'O)$_m$— (in the case of m1=1).

The (m1+1)-valent group represented by $R^{E2}$ is preferably a remaining atomic group excluding m1 hydrogen atom(s) from an alkyl group optionally having a substituent, a remaining atomic group excluding m1 hydrogen atom(s) from an aryl group optionally having a substituent, a remaining atomic group excluding m1 hydrogen atom(s) from a monovalent heterocyclic group, a remaining atomic group excluding m1 hydrogen atom(s) from an alkyl group substituted by a monovalent heterocyclic group, or a remaining atomic group excluding m1 hydrogen atom(s) from an aryl group substituted by a monovalent heterocyclic group, more preferably a remaining atomic group excluding m1 hydrogen atom(s) from an alkyl group having 1 to 6 carbon atoms, a remaining atomic group excluding m1 hydrogen atom(s) from a phenyl group, a remaining atomic group excluding m1 hydrogen atom(s) from a triazinyl group, a remaining atomic group excluding m1 hydrogen atom(s) from an alkyl group substituted by a triazinyl group, or a remaining atomic group excluding m1 hydrogen atom(s) from an aryl group substituted by a triazinyl group, further preferably a remaining atomic group excluding m1 hydrogen atom(s) from a hexyl group, a remaining atomic group excluding m1 hydrogen atom(s) from a phenyl group, or a remaining atomic group excluding m1 hydrogen atom(s) from a phenyl group substituted by a triazinyl group.

Preferable examples of $X^1$ include a group represented by the formula: —SM, a group represented by the formula: —OM, a group represented by the formula: —CO$_2$M, a group represented by the formula: —NM$_2$, a group represented by the formula: —NRM, a group represented by the formula: —PO$_3$M, a group represented by the formula: —OP(=O)(OM)$_2$, a group represented by the formula: —P(=O)(OM)$_2$, a group represented by the formula: —C(=O)NM$_2$, a group represented by the formula: —C(=O)NRM, a group represented by the formula: —SO$_3$M, a group represented by the formula: —SO$_2$M, a group represented by the formula: —NR$_3$M', a carboxyl group, a sulfo group, a hydroxy group, a mercapto group, an amino group, a substituted amino group, a cyano group, a pyrrolidonyl group, a phosphoric acid group, a phosphonic acid group, a substituted phosphonic acid group, and a monovalent heterocyclic group.

R is the same as above.

M represents a metal cation or an ammonium cation optionally having a substituent.

M' represents an anion.

A monovalent, divalent or, trivalent ion is preferable as the metal cation represented by M, and examples include ions of metals such as Li, Na, K, Cs, Be, Mg, Ca, Ba, Ag, Al, Bi, Cu, Fe, Ga, Mn, Pb, Sn, Ti, W, Y, Yb, Zn and Zr, with an ion of Li, Na, K or Cs being preferable.

Examples of the substituent optionally carried by the ammonium cation represented by M include alkyl groups having 1 to 10 carbon atoms, such as a methyl group, an ethyl group, a propyl group, an isopropyl group, a butyl group, an isobutyl group, a sec-butyl group and a tert-butyl group.

Examples of the anion represented by M' include F$^-$, Cl$^-$, Br$^-$, I$^-$, OH$^-$, ClO$^-$, ClO$_2^-$, ClO$_3^-$, ClO$_4^-$, SCN$^-$, CN$^-$, NO$_3^-$, SO$_4^{2-}$, HSO$_4^-$, PO$_4^{3-}$, HPO$_4^{2-}$, H$_2$PO$_4^-$, BF$_4^-$, PF$_6^-$, CH$_3$SO$_3^-$, CF$_3$SO$_3^-$, [(CF$_3$SO$_2$)$_2$N]$^-$, tetrakis(imidazolyl) borate anions, 8-quinolinolato anions, 2-methyl-8-quinolinolato anions and 2-phenyl-8-quinolinolato anions.

Examples of the substituted amino group include an amino group in which one or more of hydrogen atoms in the amino group are replaced with one or more groups selected from the group consisting of an alkyl group, an aryl group, an arylalkyl group and a monovalent heterocyclic group. The number of carbon atoms of the substituted amino group is usually 1 to 60, and 2 to 48 is preferable. Examples of the substituted amino group include a methylamino group, a dimethylamino group, an ethylamino group, a diethylamino group, a propylamino group, a dipropylamino group, an isopropylamino group, a diisopropylamino group, a 2-ethylhexylamino group, a nonylamino group, a decylamino group, a 3,7-dimethyloctylamino group, a laurylamino group, a cyclopentylamino group, a dicyclopentylamino group, a cyclohexylamino group, a dicyclohexylamino group, a pyrrolidyl group, a piperidyl group, a ditrifluoromethylamino group, a phenylamino group, a diphenylamino group, a 1-naphthylamine group, a 2-naphthylamino group, a pentafluorophenylamino group, a pyridylamino group, a pyridazinylamino group, a pyrimidinylamino group, a pyrazylamino group, and a triazylamino group.

Examples of the substituted phosphonic acid group include a phosphonic acid group in which one or more of hydrogen atoms in the phosphonic acid group are substituted by one or more groups selected from the group consisting of an alkyl group, an aryl group, an arylalkyl group and a monovalent heterocyclic group. The number of carbon atoms of the substituted phosphonic acid group is usually 1 to 60, and 2 to 48 is preferable. Examples of the substituted amino group include a methylphosphonic acid group, a dimethylphosphonic acid group, an ethylphosphonic acid group, a diethylphosphonic acid group, a propylphosphonic acid group, a dipropylphosphonic acid group, an isopropylphosphonic acid group, a diisopropylphosphonic acid group, a 2-ethylhexylphosphonic acid group, a nonylphosphonic acid group, a decylphosphonic acid group, a 3,7-dimethyloctylphosphonic acid group, a laurylphosphonic acid group, a cyclopentylphosphonic acid group, a dicyclopentylphosphonic acid group, a cyclohexylphosphonic acid group, a dicyclohexylphosphonic acid group, a ditrifluoromethylphosphonic acid group, a phenylphosphonic acid group, a diphenylphosphonic acid group, a 1-naphthylphosphonic acid group, a 2-naphthylphosphonic acid group, a pentafluorophenylphosphonic acid group, a pyridylphosphonic acid group, a pyridazinylphosphonic acid group, a pyrimidinylphosphonic acid group, a pyrazylphosphonic acid group, and a triazylphosphonic acid group.

Preferable examples of $X^1$ also include groups represented by the formula (I) to the formula (IX).

(I)

[Chemical Formula 28]

(II)

(III)

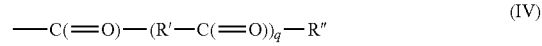
(IV)

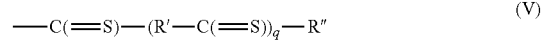
(V)

(VI)

(VII)

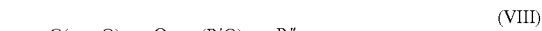
(VIII)

(IX)

R' represents a hydrocarbylene group optionally having a substituent.

R" represents a hydrogen atom, a hydrocarbyl group optionally having a substituent, a carboxyl group, a sulfo group, a hydroxy group, a mercapto group, an amino group, a group represented by —NR$^c_2$, a cyano group or a group represented by —C(=O)NR$^c_2$.

R''' represents a trivalent hydrocarbon group optionally having a substituent.

m represents an integer of 1 or larger.

q represents an integer of 0 or larger.

R$^c$ represents an alkyl group having 1 to 30 carbon atoms and optionally having a substituent or an aryl group having 6 to 50 carbon atoms and optionally having a substituent.

In the case where pluralities of R', R" and R''' are present, they are respectively the same or different.

The polymer compound as the electron-transporting material can be synthesized according to a method described in, for example, Japanese Unexamined Patent Publication Nos. 2009-239279, 2012-033845, 2012-216821, 2012-216822, or 2012-216815.

In the case where the electron-transporting material is a low-molecular compound, examples include metal complexes with 8-hydroxyquinoline as a ligand, oxadiazole, anthraquinodimethane, benzoquinone, naphthoquinone, anthraquinone, tetracyanoanthraquinodimethane, fluorenone, diphenyldicyanoethylene, carbazole, azacarbazole, diazacarbazole, benzimidazole, triazine, diphenoquinone, and their derivatives. Also, a low-molecular compound represented by the formula (H-1) is preferable as the electron-transporting material.

[Chemical Formula 29]

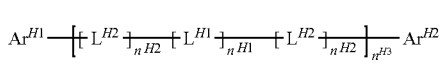
(H-1)

It is preferable that each of $Ar^{H1}$ and $Ar^{H2}$ should be a phenyl group, a fluorenyl group, a spirobifluorenyl group, a pyridyl group, a pyrimidinyl group, a triazinyl group, a quinolinyl group, an isoquinolinyl group, a thienyl group, a benzothienyl group, a dibenzothienyl group, a furyl group, a benzofuryl group, a dibenzofuryl group, a pyrrolyl group, an indolyl group, an azaindolyl group, a carbazolyl group, an azacarbazolyl group, a diazacarbazolyl group, a phenoxazinyl group or a phenothiazinyl group, it is more preferable to be a phenyl group, a spirobifluorenyl group, a pyridyl group, a pyrimidinyl group, a triazinyl group, a dibenzothienyl group, a dibenzofuryl group, a carbazolyl group or an azacarbazolyl group, it is further preferable to be a phenyl group, a pyridyl group, a carbazolyl group or an azacarbazolyl group, it is particularly preferable to be a group represented by the formula (TDA-1) or (TDA-3) mentioned later, and it is especially preferable to be a group represented by the formula (TDA-3) mentioned later, and these groups optionally have a substituent.

A halogen atom, an alkyl group, a cycloalkyl group, an alkoxy group, a cycloalkoxy group, an aryl group or a monovalent heterocyclic group is preferable as the substituent optionally carried by $Ar^{H1}$ and $Ar^{H2}$, an alkyl group, a cycloalkoxy group, an alkoxy group or a cycloalkoxy group is more preferable, and an alkyl group or a cycloalkoxy group is further preferable, and these groups optionally further have a substituent.

$n^{H1}$ is preferably 1. $n^{H2}$ is preferably 0.

$n^{H3}$ is usually an integer of 0 or larger and 10 or smaller, preferably an integer of 0 or larger and 5 or smaller, further preferably an integer of 1 or larger and 3 or smaller, particularly preferably 1.

It is preferable that $L^{H1}$ should be an arylene group or a divalent heterocyclic group.

It is preferable that $L^{H1}$ should be groups represented by the formulas (A-1) to (A-3), the formulas (A-8) to (A-10), the formulas (AA-1) to (AA-6), the formulas (AA-10) to (AA-21) or the formulas (AA-24) to (AA-34), it is more preferable to be groups represented by the formula (A-1), the formula (A-2), the formula (A-8), the formula (A-9), the formulas (AA-1) to (AA-4), the formulas (AA-10) to (AA-15) or the formulas (AA-29) to (AA-34), it is further preferable to be groups represented by the formula (A-1), the formula (A-2), the formula (A-8), the formula (A-9), the formula (AA-2), the formula (AA-4), the formulas (AA-10) to (AA-15), it is particularly preferable to be a group represented by the formula (A-1), the formula (A-2), the formula (A-8), the formula (AA-2), the formula (AA-4), the formula (AA-10) or the formula (AA-12) or the formula (AA-14), and it is especially preferable to be a group represented by the formula (A-1), the formula (A-2), the formula (AA-2), the formula (AA-4) or the formula (AA-14).

A halogen atom, an alkyl group, a cycloalkyl group, an alkoxy group, a cycloalkoxy group, an aryl group or a monovalent heterocyclic group is preferable as the substituent optionally carried by $L^{H1}$, an alkyl group, an alkoxy group, an aryl group or a monovalent heterocyclic group is more preferable, and an alkyl group, an aryl group or a monovalent heterocyclic group is further preferable, and these groups optionally further have a substituent.

$L^{H2}$ represents a group represented by $-N(-L^{H21}-R^{H21})-$. It is preferable that $L^{H21}$ should be a single bond or an arylene group, and it is more preferable to be a single bond, and this arylene group optionally has a substituent. A definition and examples of the arylene group or the divalent heterocyclic group represented by $L^{H21}$ are similar to the definition and the examples of the arylene group or the divalent heterocyclic group represented by $L^{H1}$. It is preferable that $R^{H21}$ should be an aryl group or a monovalent heterocyclic group, and these groups optionally have a substituent. Definitions and examples of the aryl group and the monovalent heterocyclic group represented by $R^{H21}$ are similar to the definitions and the examples of the aryl group and the monovalent heterocyclic group represented by $Ar^{H1}$ and $Ar^{H2}$. A definition and examples of the substituent optionally carried by $R^{H21}$ are similar to the definition and the examples of the substituent optionally carried by $Ar^{H1}$ and $Ar^{H2}$.

It is preferable that the compound represented by the formula (H-1) should be a compound represented by the formula (H-2).

[Chemical Formula 30]

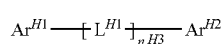
(H-2)

In the formula, $Ar^{H1}$, $Ar^{H2}$ and $L^{H1}$ are the same as above, and $n^{H3}$ represents an integer of 0 or larger.

Examples of the compound represented by the formula (H-1) include compounds represented by the formulas (H-101) to (H-118).

[Chemical Formula 31]

(H-101)

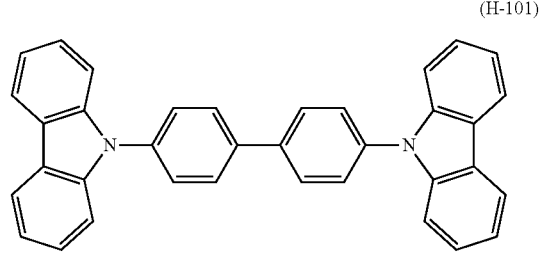

(H-102)
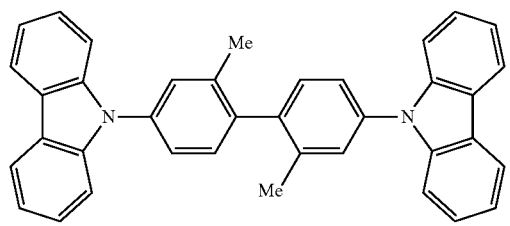
(H-103)
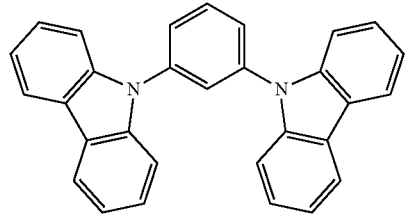
(H-104)
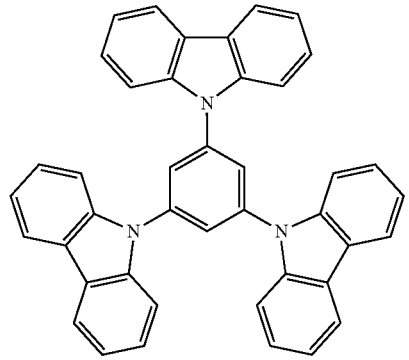
(H-105)
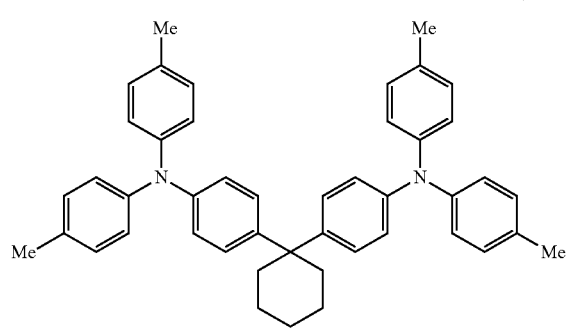
(H-106)
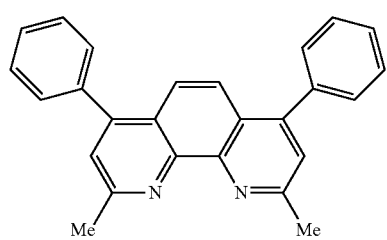
[Chemical Formula 32]
(H-107)
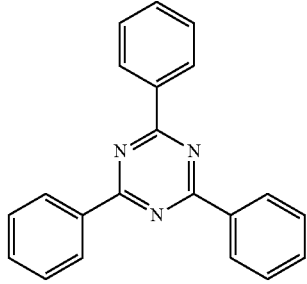
(H-108)
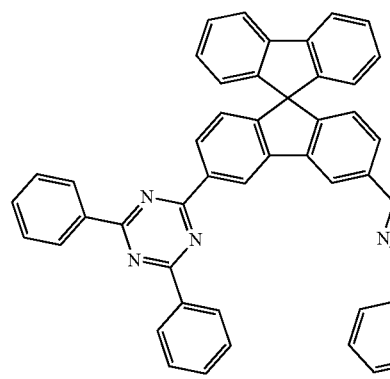
(H-109)
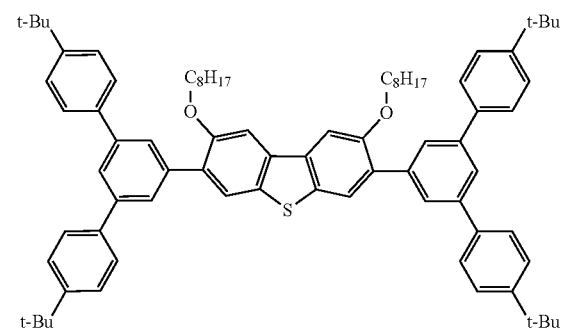
(H-110)
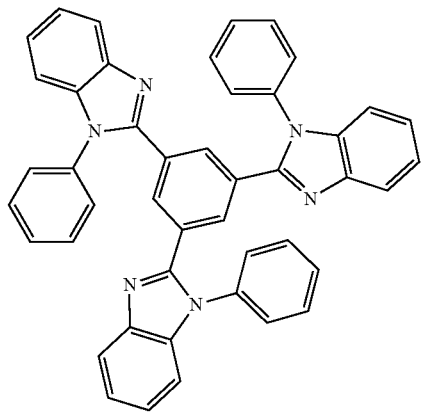

-continued (H-111)

[Chemical Formula 33]

(H-112)

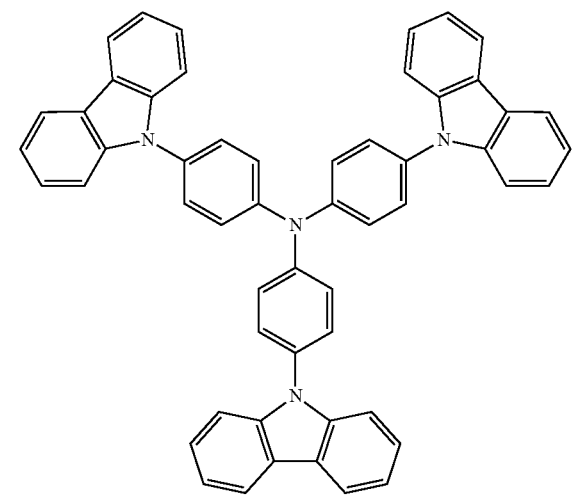

(H-113)

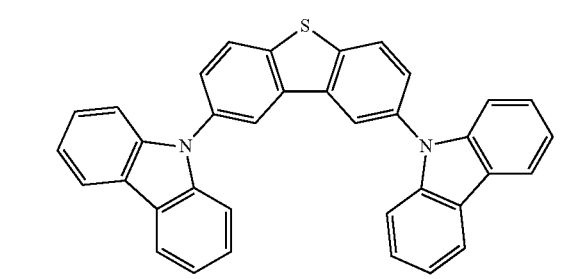

(H-114)

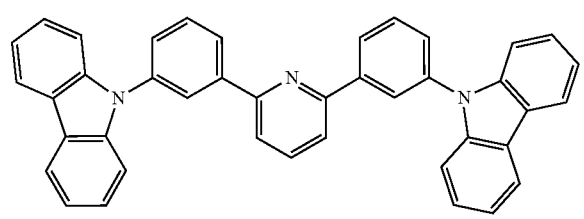

-continued
[Chemical Formula 34]

(H-115)

(H-116)

(H-117)

(H-118)

In the light-emitting device according to the present embodiment, a publicly known one can be used as an electron-transporting material other than the polymer compound comprising a constitutional unit represented by the formula (ET-1) and the compound represented by the formula (H-1), and examples include various metal complexes typified by metal complexes of triazole derivatives, oxazole derivatives, oxadiazole derivatives, imidazole derivatives, fluorene derivatives, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, anthraquinodimethane derivatives, anthrone derivatives, thiopyran dioxide derivatives, carbodiimide derivatives, fluorenylidenemethane derivatives, distyrylpyrazine derivatives, tetracarboxylic anhydrides of aromatic rings such as naphthalene and perylene, phthalocyanine derivatives, and 8-quinolinol derivatives, metallophthalocyanine, and metal complexes with benzoxazole or benzothiazole as a ligand, organosilane derivative, metal complexes of 8-hydroxyquinoline and derivatives thereof, polyquinoline and derivatives thereof, polyquinoxaline and derivatives thereof, and polyfluorene and derivatives thereof. Among these, metal complexes of triazole derivatives, oxadiazole derivatives, benzoquinone and derivatives thereof, anthraquinone and derivatives thereof, and 8-hydroxyquinoline and derivatives thereof, polyquinoline and derivatives thereof, polyquinoxaline and derivatives thereof, and polyfluorene and derivatives thereof are preferable.

In the electron-transporting layer, it is preferable that the ratio of the dopant material to 100 parts by mass of the electron-transporting material should be 1 to 50 parts by mass. Also, the ratio is preferably 5 parts by mass or more, preferably 10 parts by mass or more, further preferably 20 parts by mass or more, because the electron-transporting material can be more efficiently doped. Also, the ratio is preferably 40 parts by mass or less, more preferably 30 parts by mass or less, because the film formability of the electron-transporting layer becomes favorable.

The electron-transporting layer can be one in which the electron-transporting material is doped by activating the dopant material. For example, the electron-transporting layer can be one in which the electron-transporting material is doped by converting the derivative of the heterocyclic compound to the heterocyclic compound by activation.

The activation of the dopant material can be performed by heat or irradiation with light. The timing of the activation can be during preparation of the light-emitting device or may be after preparation of the light-emitting device.

The activation by heat can convert the derivative of the heterocyclic compound to the heterocyclic compound having the predetermined SOMO by heating the dopant material using a heat source. The heat source can be, for example, an oven, a hot plate, infrared heating, or vacuum deposition energy.

The activation by light irradiation can convert the derivative of the heterocyclic compound to the heterocyclic compound having the predetermined SOMO by irradiating the dopant material with light using a light source that can emit any light of ultraviolet light, visible light and infrared light. It is preferable for the light source to use a light source that can emit any light of ultraviolet light and visible light, because the intensity of the light is sufficiently obtained.

<Light-Emitting Layer>

In the present embodiment, the light-emitting layer can be a layer containing a light-emitting material. The light-emitting material is classified into a low-molecular compound and a polymer compound. The light-emitting material may be a polymer compound or may be a low-molecular compound. The light-emitting material can have a cross-linking group and may be cross-linked by a cross-linking group.

Examples of the low-molecular compound that is used as the light-emitting material include naphthalene and derivatives thereof, anthracene and derivatives thereof, perylene and derivatives thereof, and triplet light-emitting complexes with iridium, platinum or europium as a central metal (i.e., phosphorescent materials).

Examples of the polymer compound that is used as the light-emitting material include polymer compounds containing a phenylene group, a naphthalenediyl group, a fluorenediyl group, a phenanthrenediyl group, a dihydrophenanthrenediyl group, a group represented by the formula (X) mentioned later, a carbazolediyl group, a phenoxazinediyl group, a phenothiazinediyl group, an anthracenediyl group, a pyrenediyl group, or the like.

In the present embodiment, it is preferable that the light-emitting material should contain a triplet light-emitting complex (i.e., a phosphorescent material).

Iridium complexes such as metal complexes represented by the formulas Ir-1 to Ir-5 are preferable as the triplet light-emitting complex.

[Chemical Formula 35]

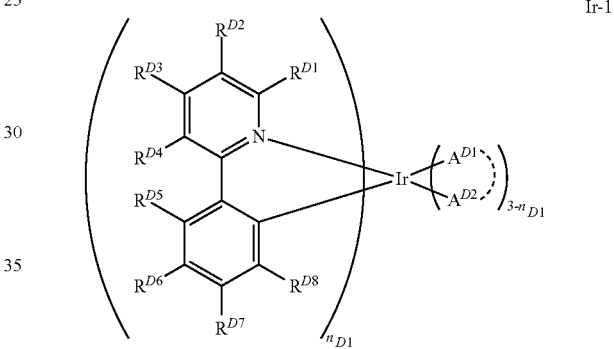

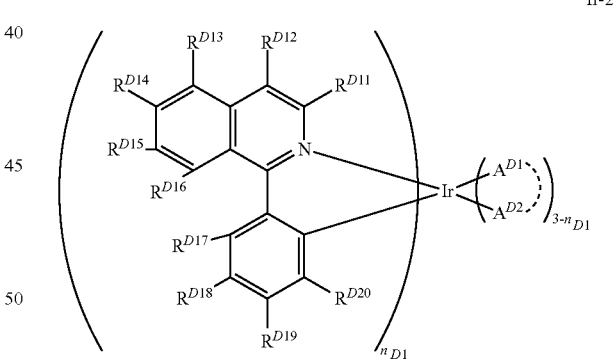

[Chemical Formula 36]

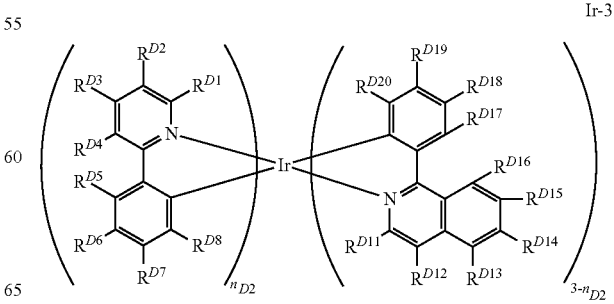

[Chemical Formula 37]

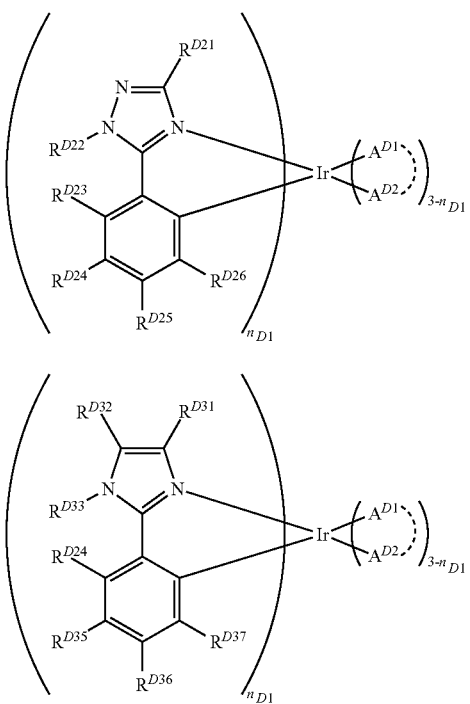

Ir-4

Ir-5

In the formulas, $R^{D1}$ to $R^{D8}$, $R^{D11}$ to $R^{D20}$, $R^{D21}$ to $R^{D26}$ and $R^{D31}$ to $R^{D37}$ each independently represent a hydrogen atom, an alkyl group, a cycloalkyl group, an alkoxy group, a cycloalkoxy group, an aryl group, an aryloxy group, a monovalent heterocyclic group or a halogen atom, and a portion or the whole of hydrogen atoms in these groups is optionally replaced with a substituent. In the case where pluralities of $R^{D1}$ to $R^{D8}$, $R^{D11}$ to $R^{D20}$, $R^{D21}$ to $R^{D26}$ and $R^{D31}$ to $R^{D37}$ are present, they are respectively the same or different.

$-A^{D1}-A^{D2}-$ represents an anionic bidentate ligand, $A^{D1}$ and $A^{D2}$ each independently represent a carbon atom, an oxygen atom or a nitrogen atom bonded to the iridium atom, and these atoms may be ring-constituting atoms. In the case where a plurality of $-A^{D1}-A^{D2}-$ are present, they are the same or different.

$n^{D1}$ represents 1, 2 or 3, and $n^{D2}$ represents 1 or 2.

In the metal complex represented by the formula Ir-1, at least one of $R^{D1}$ to $R^{D8}$ is preferably a group represented by the formula (D-A).

In the metal complex represented by the formula Ir-2, preferably, at least one of $R^{D11}$ to $R^{D20}$ is a group represented by the formula (D-A).

In the metal complex represented by the formula Ir-3, preferably, at least one of $R^{D1}$ to $R^{D8}$ and $R^{D11}$ to $R^{D20}$ is a group represented by the formula (D-A).

In the metal complex represented by the formula Ir-4, preferably, at least one of $R^{D21}$ to $R^{D26}$ is a group represented by the formula (D-A).

In the metal complex represented by the formula Ir-5, preferably, at least one of $R^{D31}$ to $R^{D37}$ is a group represented by the formula (D-A).

[Chemical Formula 38]

(D-A)

In the formula, $m^{DA1}$, $m^{DA2}$ and $m^{DA3}$ each independently represent an integer of 0 or larger.

$G^{DA}$ represents a nitrogen atom, an aromatic hydrocarbon group or a heterocyclic group, and a portion or the whole of hydrogen atoms in these groups is optionally replaced with a substituent.

$Ar^{DA1}$, $Ar^{DA2}$ and $Ar^{DA3}$ each independently represent an arylene group or a divalent heterocyclic group, and a portion or the whole of hydrogen atoms in these groups is optionally replaced with a substituent. In the case where pluralities of $Ar^{DA1}$, $Ar^{DA2}$ and $Ar^{DA3}$ are present, they are respectively the same or different.

$T^{DA}$ represents an aryl group or a monovalent heterocyclic group, and a portion or the whole of hydrogen atoms in these groups is optionally replaced with a substituent. A plurality of $T^{DA}$ are the same or different.

$m^{DA1}$, $m^{DA2}$ and $m^{DA3}$ are usually an integer of 10 or smaller, preferably an integer of 5 or smaller, more preferably 0 or 1. It is preferable that $m^{DA1}$, $m^{DA2}$ and $m^{DA3}$ should be the same integers.

$G^{DA}$ is preferably groups represented by the formulas (GDA-11) to (GDA-15), and a portion or the whole of hydrogen atoms in these groups is optionally replaced with a substituent.

[Chemical Formula 39]

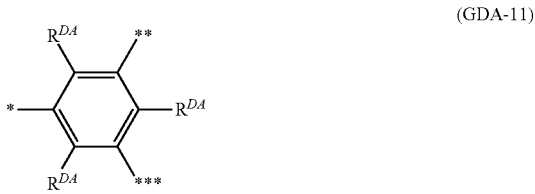

(GDA-11)

(GDA-12)

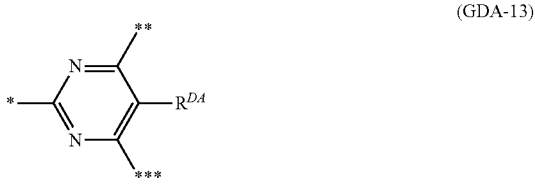

(GDA-13)

(GDA-14)

-continued (GDA-15)

[structure of carbazole with R^DA substituents and bonds *, , *]

In the formulas,

*,  and * represent bonds to Ar$^{DA1}$, Ar$^{DA2}$ and Ar$^{DA3}$, respectively.

R$^{DA}$ represents a hydrogen atom, an alkyl group, a cycloalkyl group, an alkoxy group, a cycloalkoxy group, an aryl group or a monovalent heterocyclic group, and a portion or the whole of hydrogen atoms in these groups is optionally replaced with a substituent. In the case where a plurality of R$^{DA}$ are present, they are the same or different.

R$^{DA}$ is preferably a hydrogen atom, an alkyl group, a cycloalkyl group, an alkoxy group or a cycloalkoxy group, more preferably a hydrogen atom, an alkyl group or a cycloalkyl group, and a portion or the whole of hydrogen atoms in these groups is optionally replaced with a substituent.

Ar$^{DA1}$, Ar$^{DA2}$ and Ar$^{DA3}$ are preferably groups represented by the formulas (ArDA-1) to (ArDA-3).

[Chemical Formula 40]

(ArDA-1)

[benzene ring with R$^{DA}$ substituents]

(ArDA-2)

[fluorene structure with R$^{DA}$ and R$^{DB}$ substituents]

(ArDA-3)

[carbazole structure with R$^{DA}$ and R$^{DB}$ substituents]

In the formulas,

R$^{DA}$ represents the same meaning as above.

R$^{DB}$ represents a hydrogen atom, an alkyl group, a cycloalkyl group, an aryl group or a monovalent heterocyclic group, and a portion or the whole of hydrogen atoms in these groups is optionally replaced with a substituent. In the case where a plurality of R$^{DB}$ are present, they are the same or different.

T$^{DA}$ is preferably groups represented by the formulas (TDA-1) to (TDA-3).

[Chemical Formula 41]

(TDA-1)

[benzene ring with R$^{DA}$ substituents]

(TDA-2)

[fluorene structure with R$^{DA}$ and R$^{DB}$ substituents]

(TDA-3)

[carbazole structure with R$^{DA}$ substituents]

In the formulas, R$^{DA}$ and R$^{DB}$ represent the same meanings as above.

The group represented by the formula (D-A) is preferably groups represented by the formulas (D-A1) to (D-A3).

[Chemical Formula 42]

(D-A1)

[three phenyl rings connected, with (R$^{p1}$)$_{np1}$, (R$^{p2}$)$_{np2}$, (R$^{p1}$)$_{np1}$ substituents]

(D-A2)

[phenyl-pyrazine-phenyl structure with (R$^{p1}$)$_{np1}$, (R$^{p3}$)$_{np3}$, (R$^{p1}$)$_{np1}$ substituents]

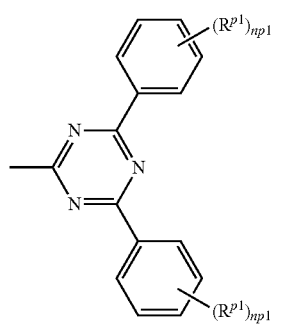
(D-A3)

In the formulas, $R^{p1}$, $R^{p2}$ and $R^{p3}$ each independently represent an alkyl group, a cycloalkyl group, an alkoxy group, a cycloalkoxy group or a halogen atom. In the case where pluralities of $R^{p1}$ and $R^{p2}$ are present, they are respectively the same or different.

np1 represents an integer of 0 to 5, np2 represents an integer of 0 to 3, and np3 represents 0 or 1. A plurality of np1 are the same or different.

np1 is preferably an integer of 0 to 3, more preferably an integer of 1 to 3, further preferably 1. np2 is preferably 0 or 1, more preferably 0. np3 is preferably 0.

Each of $R^{p1}$, $R^{p2}$ and $R^{p3}$ is preferably an alkyl group or a cycloalkyl group.

Examples of the anionic bidentate ligand represented by -$A^{D1}$-$A^{D2}$- include ligands represented by the following formulas:

[Chemical Formula 43]

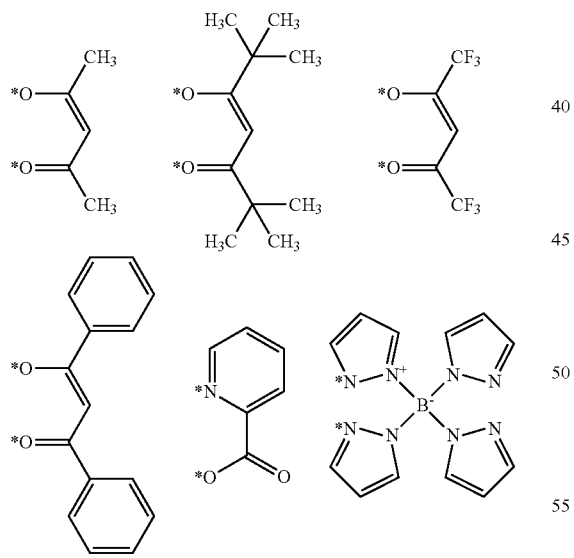

in the formulas, * represents a site bonded to Ir.

The metal complex represented by the formula Ir-1 is preferably metal complexes represented by the formulas Ir-11 to Ir-13. The metal complex represented by the formula Ir-2 is preferably a metal complex represented by the formula Ir-21. The metal complex represented by the formula Ir-3 is preferably metal complexes represented by the formulas Ir-31 to Ir-33. The metal complex represented by the formula Ir-4 is preferably metal complexes represented by the formulas Ir-41 to Ir-43. The metal complex represented by the formula Ir-5 is preferably metal complexes represented by the formulas Ir-51 to Ir-53.

[Chemical Formula 44]

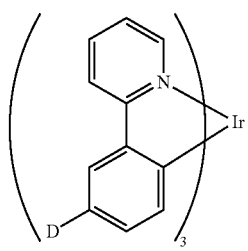
Ir-11

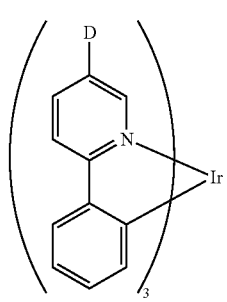
Ir-12

Ir-13

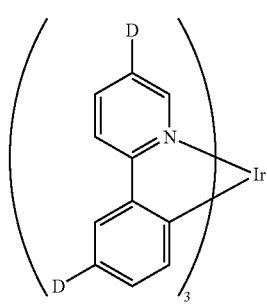
Ir-21

[Chemical Formula 45]

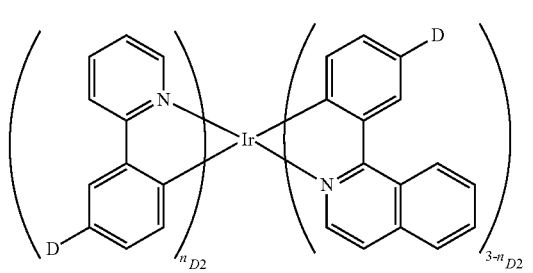
Ir-31

Ir-32

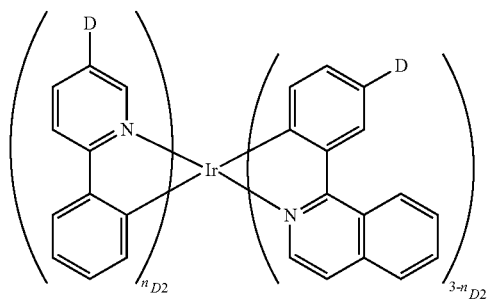

[Chemical Formula 46]

Ir-33

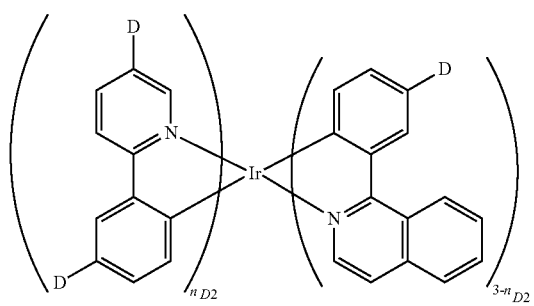

[Chemical Formula 47]

Ir-41

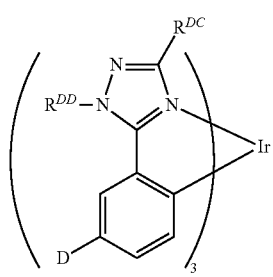

Ir-42

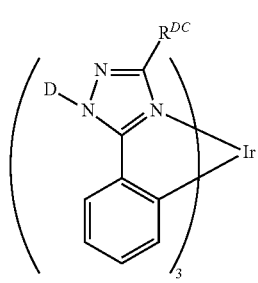

Ir-43

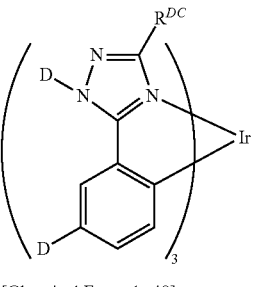

[Chemical Formula 48]

Ir-51

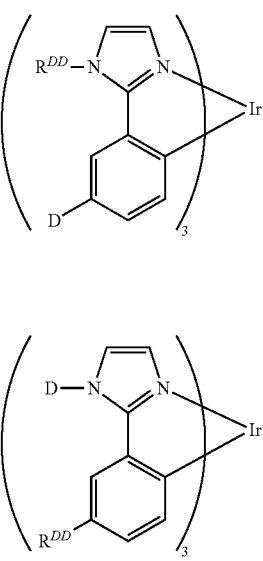

Ir-52

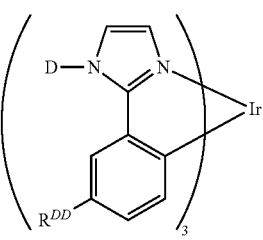

Ir-53

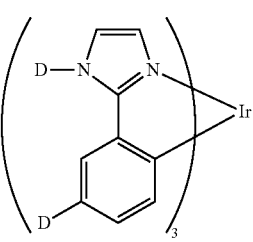

nD2 represents 1 or 2.

D represents a group represented by the formula (D-A). A plurality of D present are the same or different.

$R^{DC}$ represents a hydrogen atom, an alkyl group, a cycloalkyl group, an aryl group or a monovalent heterocyclic group, and a portion or the whole of hydrogen atoms in these groups is optionally replaced with a substituent. A plurality of $R^{DC}$ present are the same or different.

$R^{DD}$ represents an alkyl group, a cycloalkyl group, an aryl group or a monovalent heterocyclic group, and a portion or the whole of hydrogen atoms in these groups is optionally replaced with a substituent. A plurality of $R^{DD}$ present are the same or different.

Examples of the triplet light-emitting complex include metal complexes shown below.

[Chemical Formula 49]
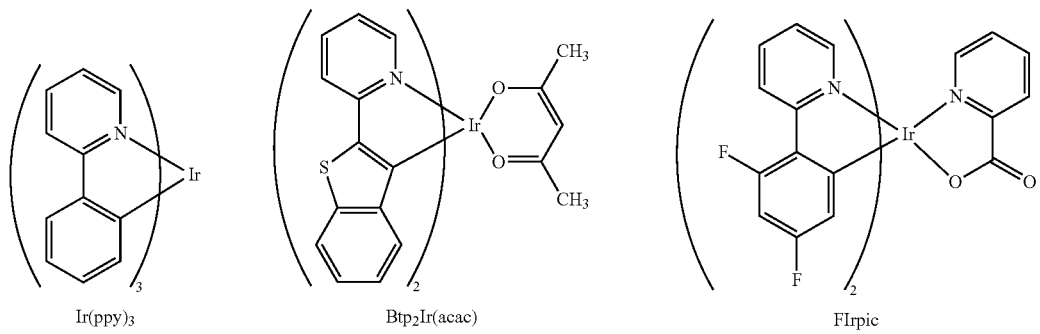
Ir(ppy)₃  Btp₂Ir(acac)  FIrpic
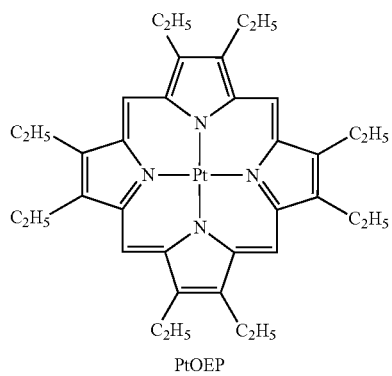
PtOEP
[Chemical Formula 50]
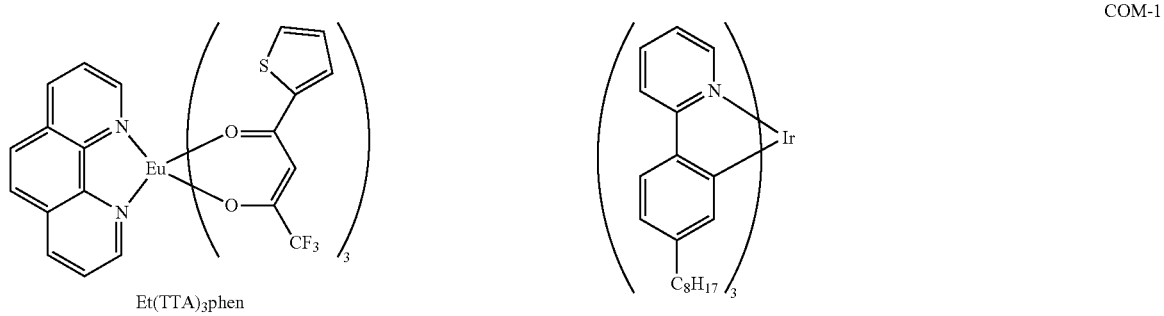
Et(TTA)₃phen  COM-1
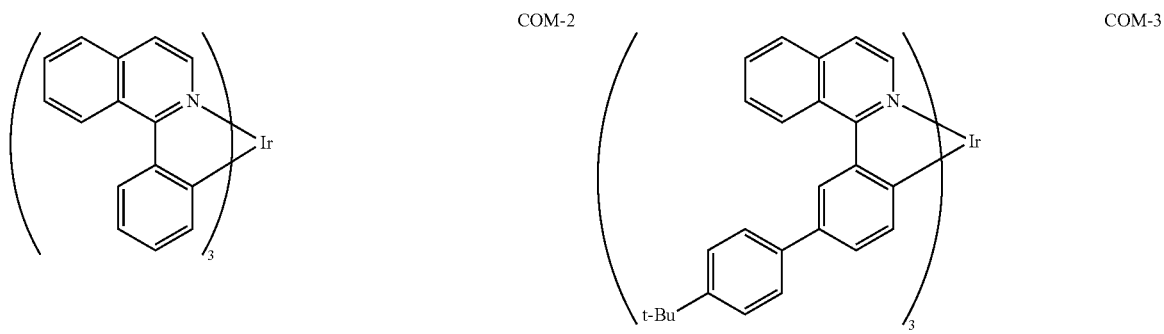
COM-2  COM-3

[Chemical Formula 51]
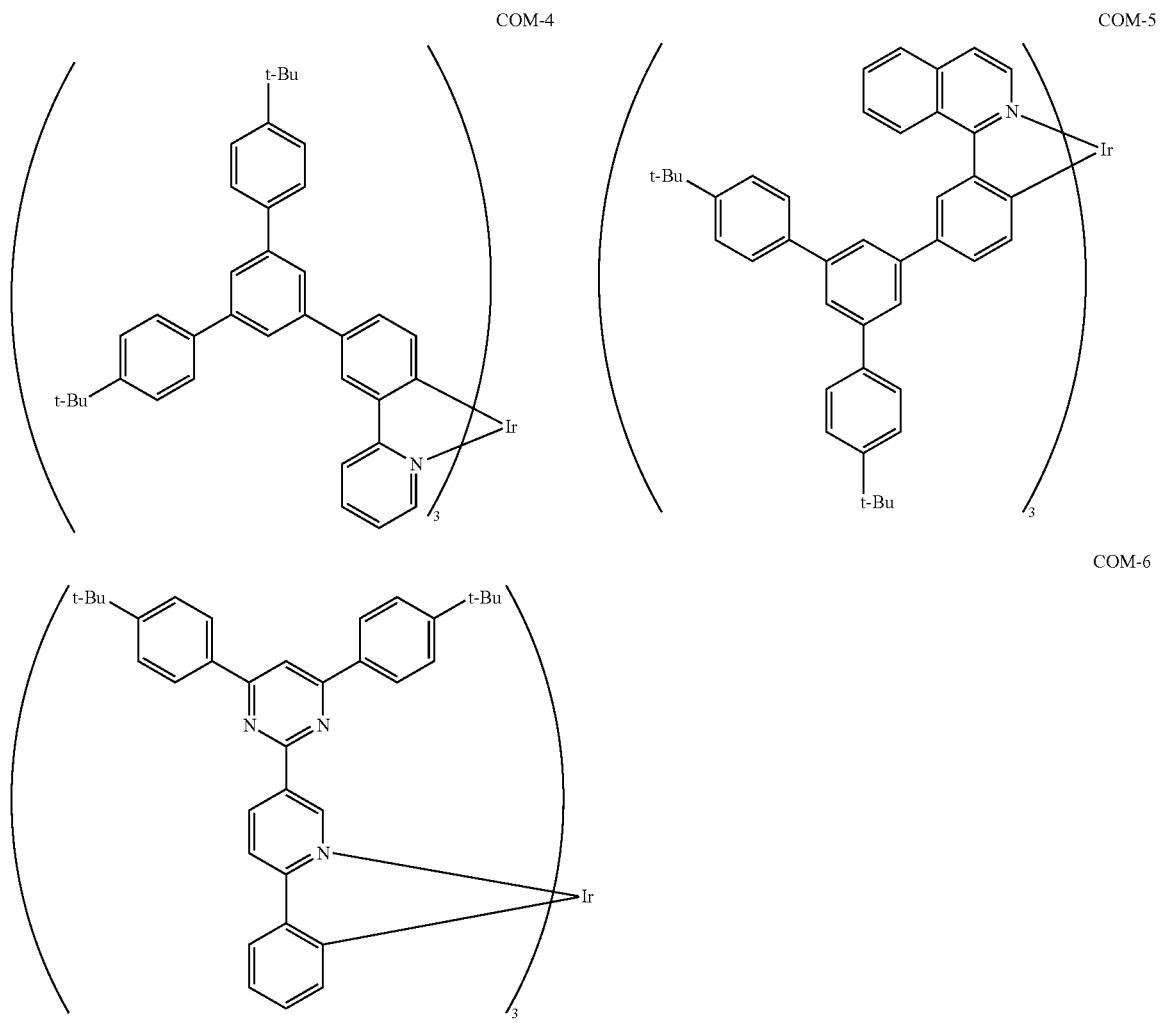
COM-4, COM-5, COM-6
[Chemical Formula 52]
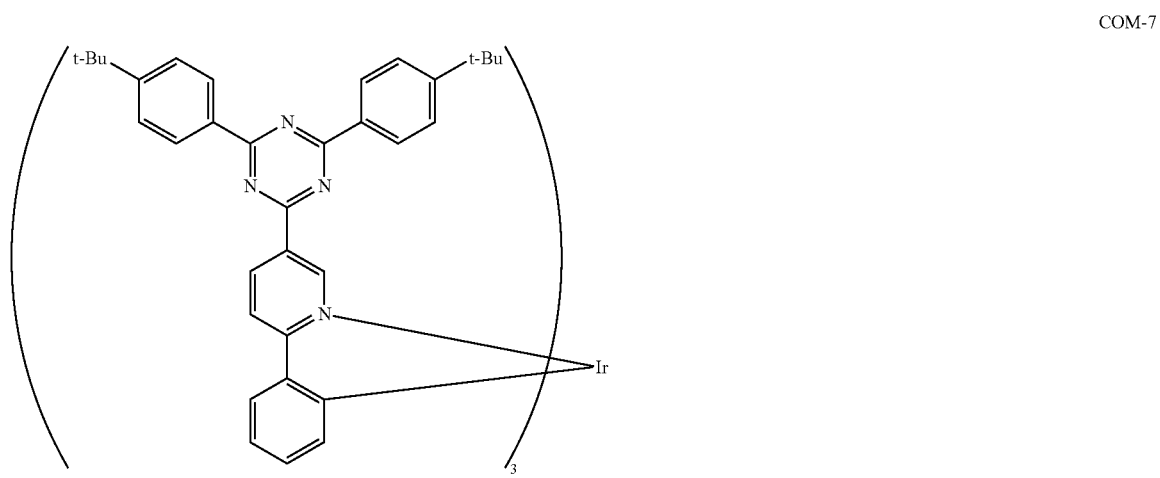
COM-7

COM-8
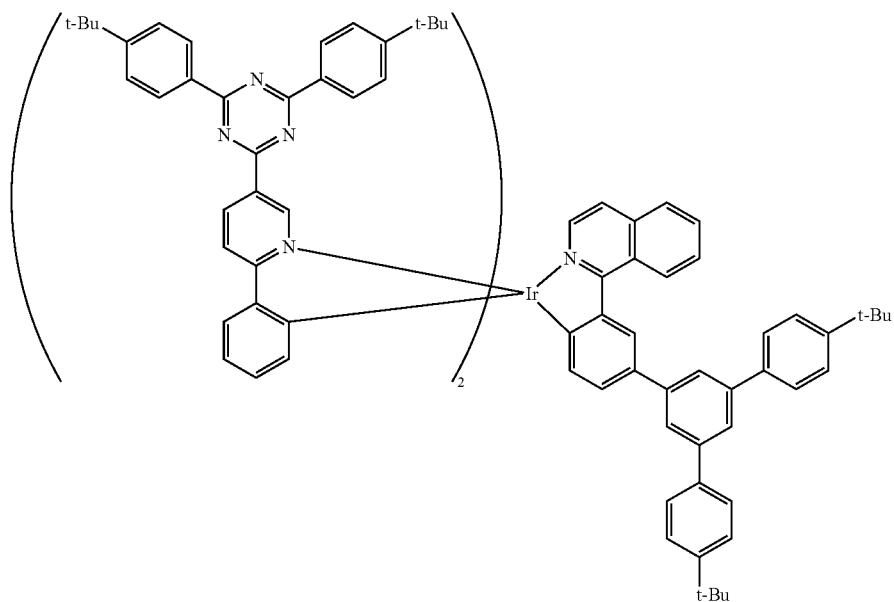
[Chemical Formula 53]
COM-9
COM-10
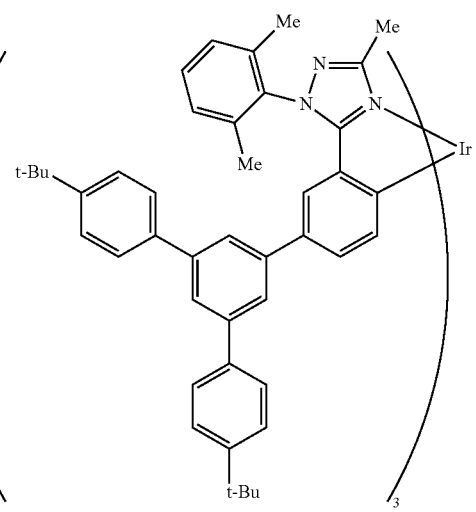
COM-11
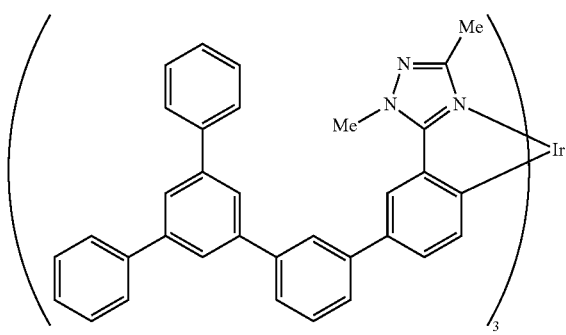

-continued
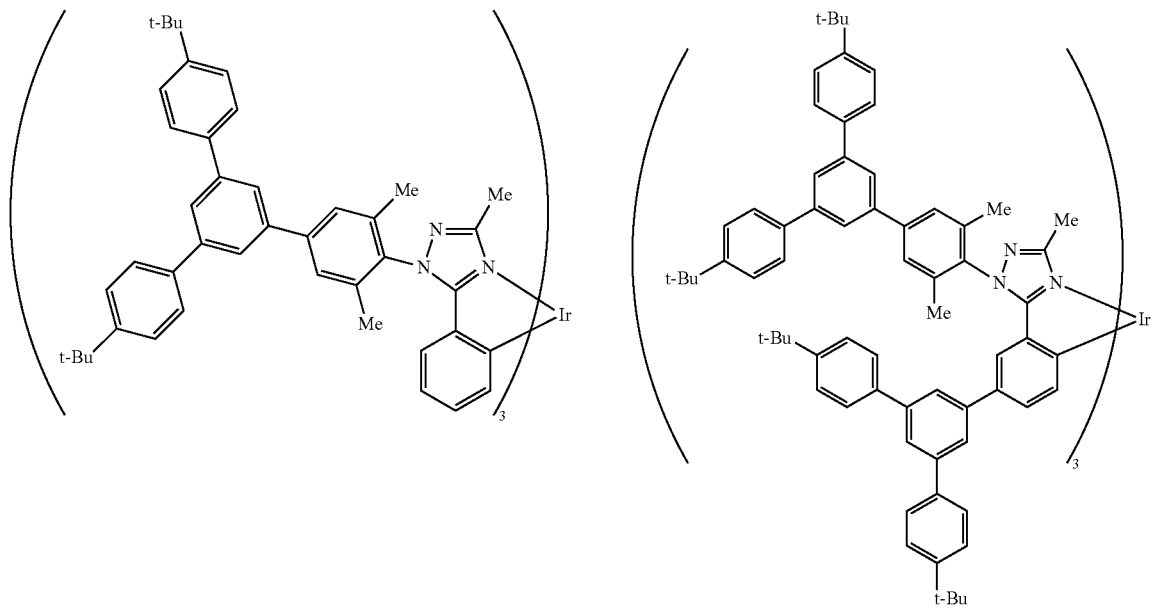
COM-12
COM-13
[Chemical Formula 54]
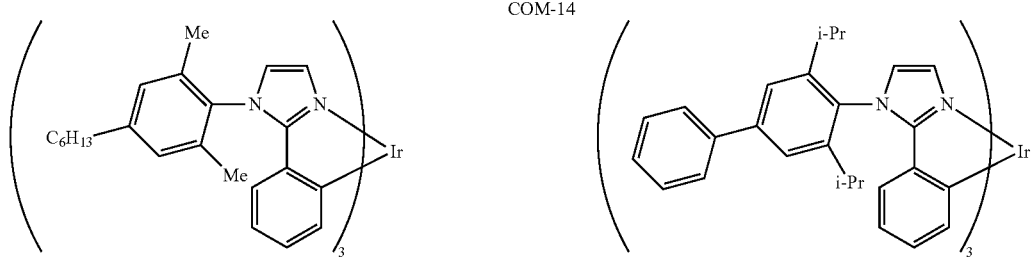
COM-14
COM-15
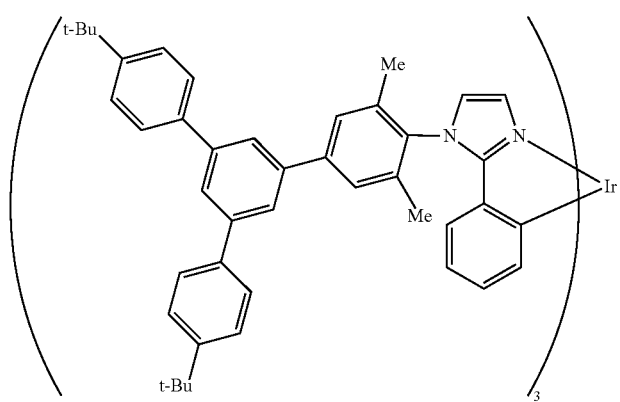
COM-16

COM-17
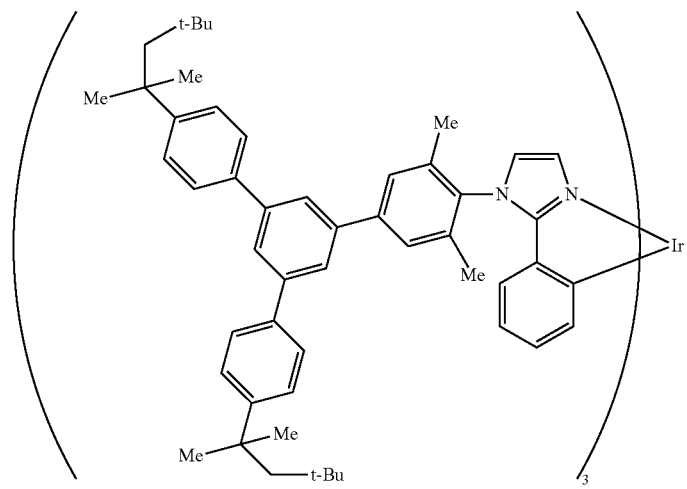
COM-18
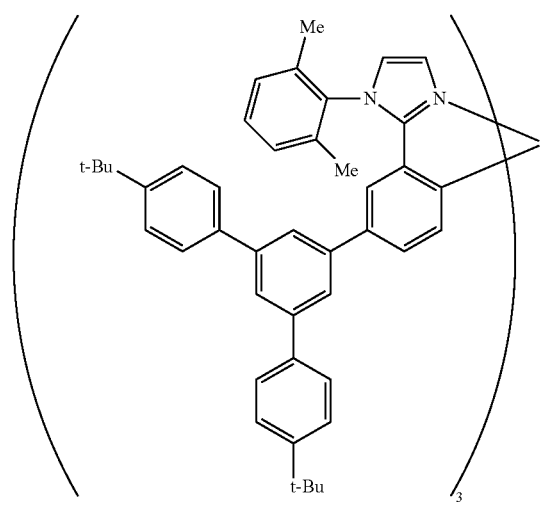
COM-19
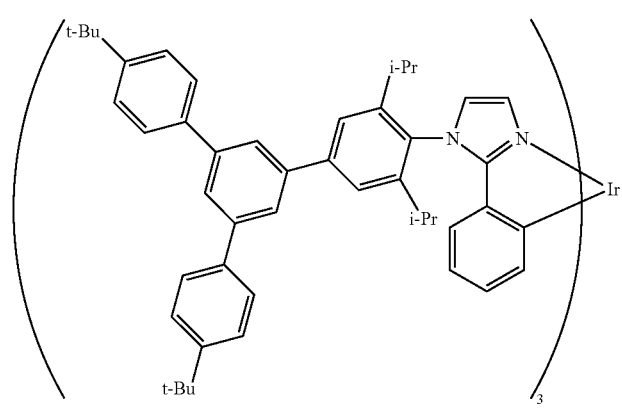

COM-20

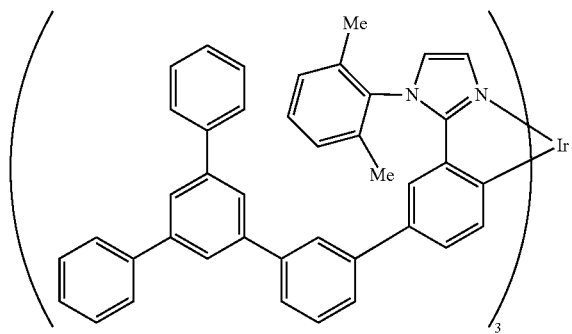

COM-21

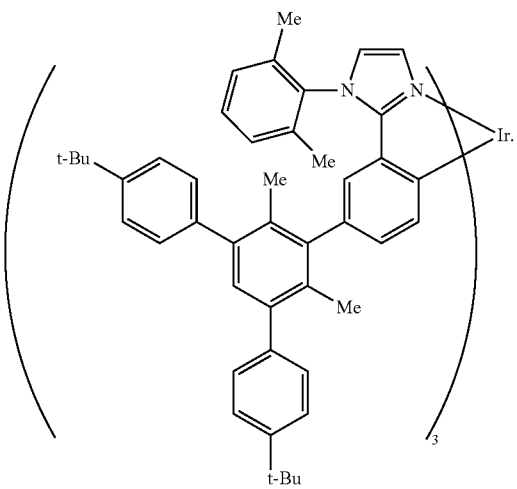

In the present embodiment, it is preferable that the light-emitting layer should contain a host material together with the light-emitting material. The host material is classified into a low-molecular compound and a polymer compound. The host material may be a polymer compound or may be a low-molecular compound.

Examples of the low-molecular compound that is used as the host material include compounds having a carbazole skeleton, compounds having a triarylamine skeleton, compounds having a phenanthroline skeleton, compounds having a triaryltriazine skeleton, compounds having an azole skeleton, compounds having a benzothiophene skeleton, compounds having a benzofuran skeleton, compounds having a fluorene skeleton, and compounds having a spirofluorene skeleton, and one example thereof is compounds represented by the following formulas:

[Chemical Formula55]

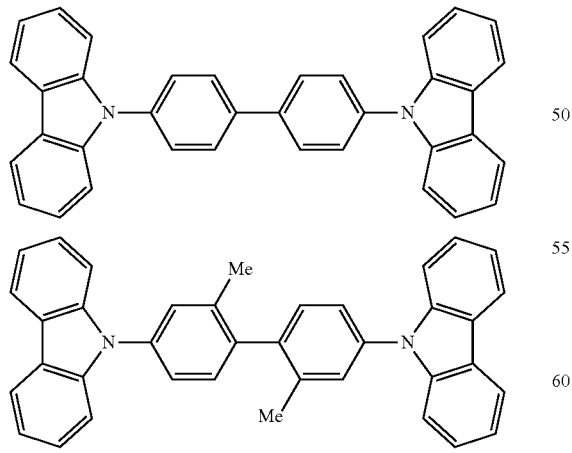

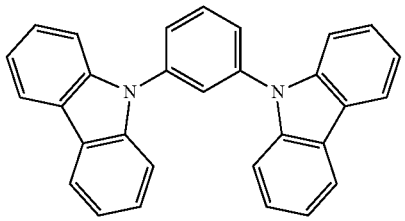

[Chemical Formula 56]

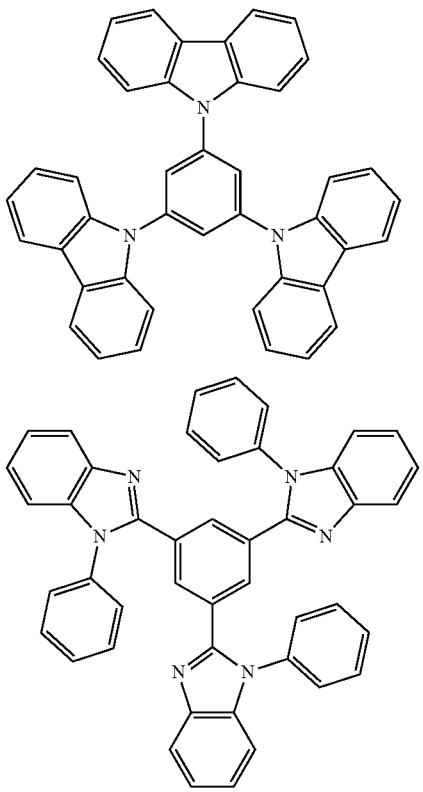

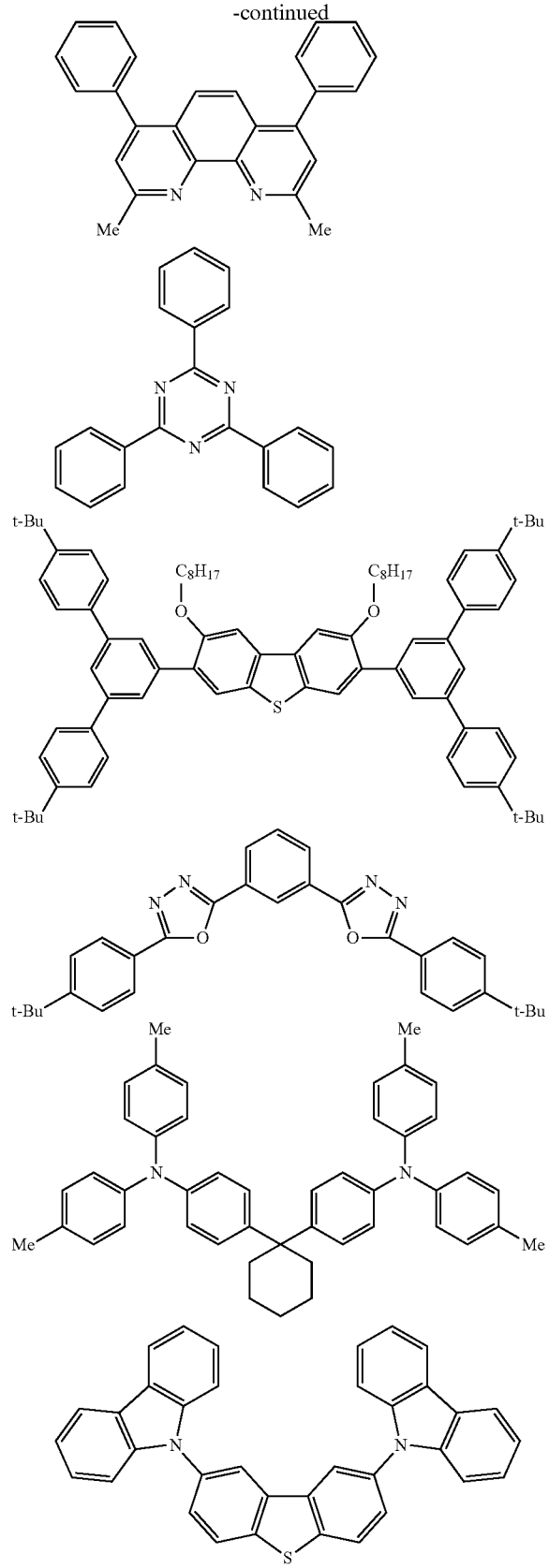

ably a polymer compound comprising a constitutional unit represented by the formula (Y).

[Chemical Formula 57]

$$-\!\!\!+\!\!Ar^{Y1}\!\!+\!\!\!-\qquad\qquad(Y)$$

In the formula, $Ar^{Y1}$ represents an arylene group, a divalent heterocyclic group, or a divalent group in which at least one arylene group and at least one divalent heterocyclic group are directly bonded, and a portion or the whole of hydrogen atoms in these groups is optionally replaced with a substituent.

The arylene group represented by $Ar^{Y1}$ is more preferably groups represented by the formula (A-1), the formula (A-2), the formulas (A-6) to (A-10), the formula (A-19) or the formula (A-20), further preferably a group represented by the formula (A-1), the formula (A-2), the formula (A-7), the formula (A-9) or the formula (A-19), and a portion or the whole of hydrogen atoms in these groups is optionally replaced with a substituent.

The divalent heterocyclic group represented by $Ar^{Y1}$ is more preferably groups represented by the formulas (AA-1) to (AA-4), the formulas (AA-10) to (AA-15), the formulas (AA-18) to (AA-21), the formula (AA-33) or the formula (AA-34), further preferably a group represented by the formula (AA-4), the formula (AA-10), the formula (AA-12), the formula (AA-14) or the formula (AA-33), and a portion or the whole of hydrogen atoms in these groups is optionally replaced with a substituent.

More preferable ranges and further preferable ranges of the arylene group and the divalent heterocyclic group in the divalent group in which at least one arylene group and at least one divalent heterocyclic group are directly bonded, represented by $Ar^{Y1}$ are similar to the more preferable ranges and the further preferable ranges of the arylene group and a divalent heterocyclic group, respectively, represented by $Ar^{Y1}$ mentioned above.

Examples of the "divalent group in which at least one arylene group and at least one divalent heterocyclic group are directly bonded" include groups represented by the following formulas, and a portion or the whole of hydrogen atoms in these groups is optionally replaced with a substituent.

[Chemical Formula 58]

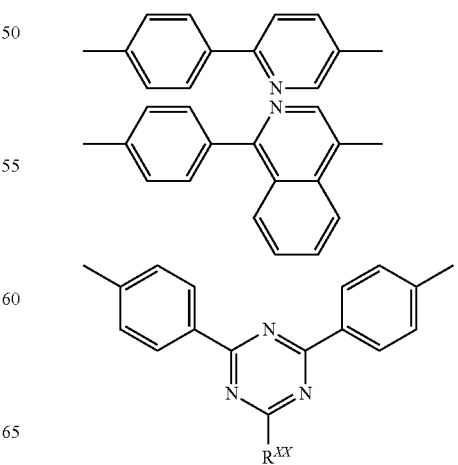

The polymer compound that is used as the host material (hereinafter, also referred to as a "polymer host") is prefer-

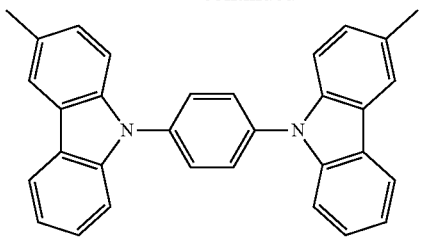

In the formulas, $R^{XX}$ represents a hydrogen atom, an alkyl group, a cycloalkyl group, an aryl group or a monovalent heterocyclic group, and a portion or the whole of hydrogen atoms in these groups is optionally replaced with a substituent.

$R^{XX}$ is preferably an alkyl group, a cycloalkyl group or an aryl group, and a portion or the whole of hydrogen atoms in these groups is optionally replaced with a substituent.

The substituent optionally carried by the group represented by $Ar^{Y1}$ is preferably an alkyl group, a cycloalkyl group or an aryl group, and a portion or the whole of hydrogen atoms in these groups is optionally further replaced with a substituent.

Examples of the constitutional unit represented by the formula (Y) include constitutional units represented by the formulas (Y-1) to (Y-10). The constitutional unit represented by the formula (Y) is preferably constitutional units represented by the formulas (Y-1) to (Y-3) from the viewpoint that the luminance lifetime of the light-emitting device improves, preferably constitutional units represented by the formulas (Y-4) to (Y-7) from the viewpoint that an electron-transporting function improves, and preferably constitutional units represented by the formulas (Y-8) to (Y-10) from the viewpoint that a hole-transporting function improves.

[Chemical Formula 59]

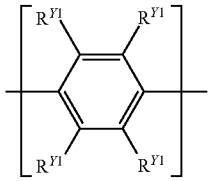

(Y-1)

In the formula, $R^{Y1}$ represents a hydrogen atom, an alkyl group, a cycloalkyl group, an alkoxy group, a cycloalkoxy group, an aryl group or a monovalent heterocyclic group, and a portion or the whole of hydrogen atoms in these groups is optionally replaced with a substituent. A plurality of $R^{Y1}$ present are the same or different and, and adjacent $R^{Y1}$ are optionally bonded to each other to form a ring together with the carbon atoms to which they are attached.

$R^{Y1}$ is preferably a hydrogen atom, an alkyl group, a cycloalkyl group or an aryl group, and a portion or the whole of hydrogen atoms in these groups is optionally replaced with a substituent.

The constitutional unit represented by the formula (Y-1) is preferably a constitutional unit represented by the formula (Y-11.

[Chemical Formula 60]

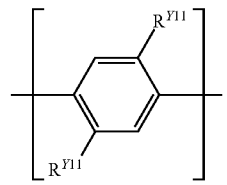

(Y-1')

In the formula, $R^{Y11}$ represents an alkyl group, a cycloalkyl group, an alkoxy group, a cycloalkoxy group, an aryl group or a monovalent heterocyclic group, and a portion or the whole of hydrogen atoms in these groups is optionally replaced with a substituent. A plurality of $R^{Y11}$ present are the same or different.

$R^{Y11}$ is preferably an alkyl group, a cycloalkyl group or an aryl group, more preferably an alkyl group or a cycloalkyl group, and a portion or the whole of hydrogen atoms in these groups is optionally replaced with a substituent.

[Chemical Formula 61]

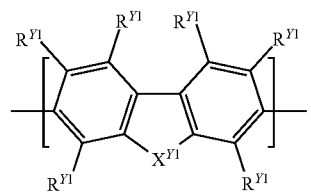

(Y-2)

$R^{Y1}$ represents the same meaning as above.
$X^{Y1}$ represents a group represented by —C($R^{Y2}$)$_2$—, —C($R^{Y2}$)=C($R^{Y2}$)— or —C($R^{Y2}$)$_2$—C($R^{Y2}$)$_2$—.
$R^{Y2}$ represents a hydrogen atom, an alkyl group, a cycloalkyl group, an alkoxy group, a cycloalkoxy group, an aryl group or a. monovalent heterocyclic group, and a portion or the whole of hydrogen atoms in these groups is optionally replaced with a substituent. A plurality of $R^{Y2}$ present are the same or different, and $R^{Y2}$ are optionally bonded to each other to form a ring together with the carbon atoms to which they are attached.

$R^{Y2}$ is preferably an alkyl group, a cycloalkyl group, an aryl group or a monovalent heterocyclic group, more preferably an alkyl group, a cycloalkyl group or an aryl group, and a portion or the whole of hydrogen atoms in these groups is optionally replaced with a substituent.

In $X^{Y1}$, the combination of two $R^{Y2}$ in the group represented by —C($R^{Y2}$)$_2$— is preferably alkyl groups or cycloalkyl groups for both, aryl groups for both, monovalent heterocyclic groups for both, or an alkyl group or a cycloalkyl group for one of them and an acyl group or a monovalent heterocyclic group for the other, more preferably an alkyl group or a cycloalkyl group for one of them and an aryl group for the other, and a portion or the whole of hydrogen atoms in these groups is optionally replaced with a substituent.

Two $R^{Y2}$ present are optionally bonded to each other to form a ring together with the atoms to which they are attached, and in the case where $R^{Y2}$ forms a ring, the group represented by —C($R^{Y2}$)$_2$— is preferably groups represented by the formulas (Y-A1) to (Y-A5), more preferably a group represented by the formula (Y-A4), and a portion or the whole of hydrogen atoms in these groups is optionally replaced with a substituent.

[Chemical Formula 62]

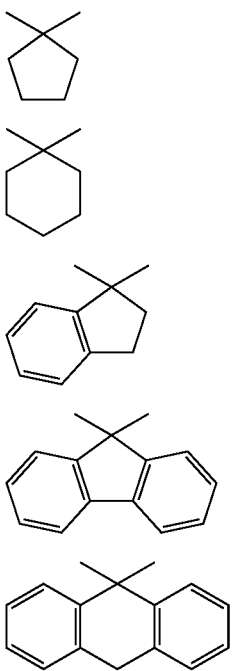

(Y-A1)

(Y-A2)

(Y-A3)

(Y-A4)

(Y-A5)

In $X^{Y1}$, the combination of two $R^{Y2}$ in the group represented by —C($R^{Y2}$)=C($R^{Y2}$)— is preferably alkyl groups or cycloalkyl groups for both, or an alkyl group or a cycloalkyl group for one of them and an aryl group for the other, and a portion or the whole of hydrogen atoms in these groups is optionally replaced with a substituent.

In $X^{Y1}$, each of four $R^{Y2}$ in the group represented by —C($R^{Y2}$)$_2$—C($R^{Y2}$)$_2$— is preferably an alkyl group optionally having a substituent or a cycloalkyl group optionally having a substituent. A plurality of $R^{Y2}$ are optionally bonded to each other to form a ring together with the atoms to which they are attached, and in the case where $R^{Y2}$ forms a ring, the group represented by —C($R^{Y2}$)$_2$—C($R^{Y2}$)$_2$— is preferably groups represented by the formulas (Y-B1) to (Y-B5), more preferably a group represented by the formula (Y-B3), and a portion or the whole of hydrogen atoms in these groups is optionally replaced with a substituent.

[Chemical Formula 63]

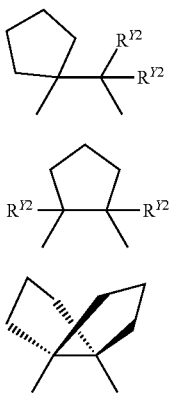

(Y-B1)

(Y-B2)

(Y-B3)

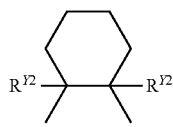

(Y-A1)

(Y-B4)

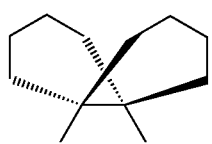

(Y-B5)

In the formulas, $R^{Y2}$ represents the same meaning as above.

It is preferable that the constitutional unit represented by the formula (Y-2) should be a constitutional unit represented by the formula (Y-2').

[Chemical Formula 64]

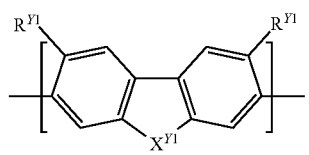

(Y-2')

In the formula, $R^{Y1}$ and $X^{Y1}$ represent the same meanings as above.

[Chemical Formula 65]

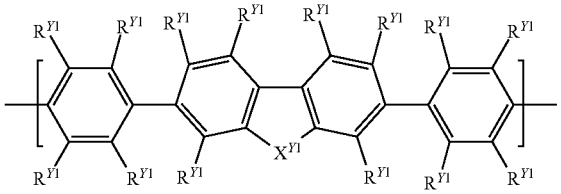

(Y-3)

in the formula, $R^{Y1}$ and $X^{Y1}$ represent the same meanings as above.

It is preferable that the constitutional unit represented by the formula (Y-3) should be a constitutional unit represented by the formula (Y-3').

[Chemical Formula 66]

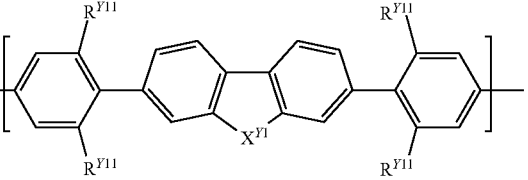

(Y-3')

In the formula, $R^{Y11}$ and $X^{Y1}$ represent the same meanings as above.

[Chemical Formula 67]

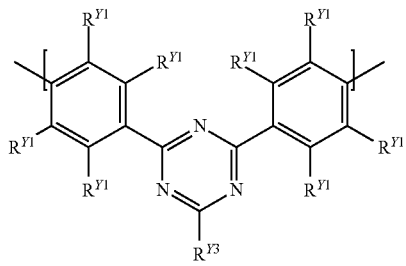
(Y-4)

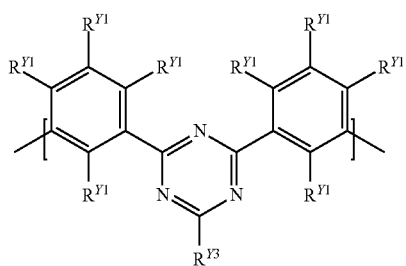
(Y-5)

[Chemical Formula 68]

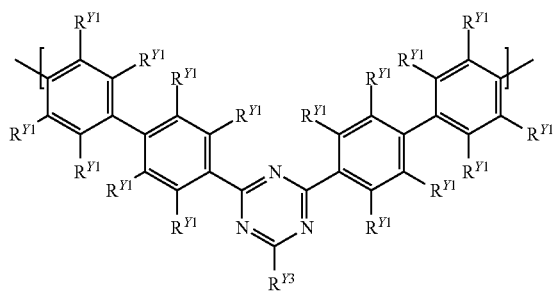
(Y-6)

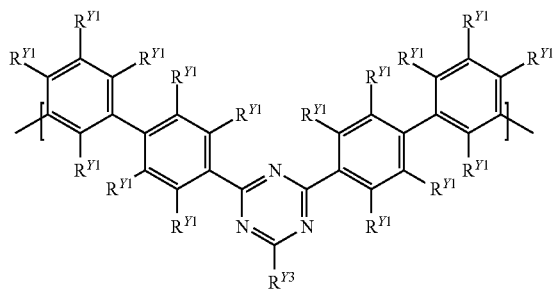
(Y-7)

In the formulas, $R^{Y1}$ represents the same meaning as above.

$R^{Y3}$ represents a hydrogen atom, an alkyl group, a cycloalkyl group, an alkoxy group, a cycloalkoxy group, an aryl group or a monovalent heterocyclic group, and a portion or the whole of hydrogen atoms in these groups is optionally replaced with a substituent.

$R^{Y3}$ is preferably an alkyl group, a cycloalkyl group, an alkoxy group, a cycloalkoxy group, an aryl group or a monovalent heterocyclic group, more preferably an aryl group, and a portion or the whole of hydrogen atoms in these groups is optionally replaced with a substituent.

It is preferable that the constitutional unit represented by the formula (Y-4) should be a constitutional unit represented by the formula (Y-4'), and it is preferable that the constitutional unit represented by the formula (Y-6) should be a constitutional unit represented by the formula (Y-6').

[Chemical Formula 69]

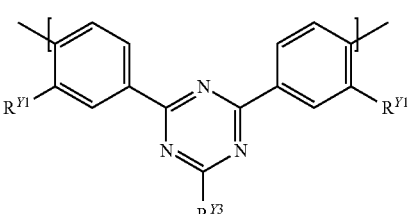
(Y-4')

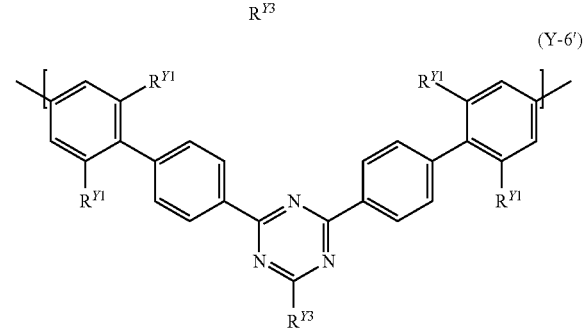
(Y-6')

In the formulas, $R^{Y1}$ and $R^{Y3}$ represent the same meanings as above.

[Chemical Formula 70]

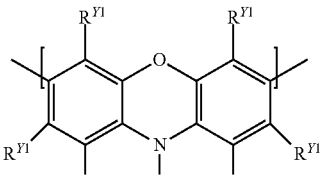
(Y-8)

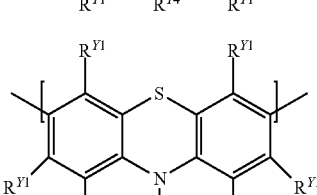
(Y-9)

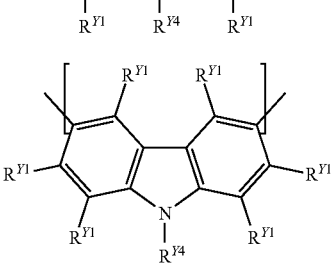
(Y-10)

In the formulas, $R^{Y1}$ represents the same meaning as above.

$R^{Y4}$ represents a hydrogen atom, an alkyl group, a cycloalkyl group, an alkoxy group, a cycloalkoxy group, an aryl group or a monovalent heterocyclic group, and a portion or the whole of hydrogen atoms in these groups is optionally replaced with a substituent.

$R^{Y4}$ is preferably an alkyl group, a cycloalkyl group, an alkoxy group, a cycloalkoxy group, an aryl group or a monovalent heterocyclic. group, more preferably an aryl group, and a portion or the whole of hydrogen atoms in these groups is optionally replaced with a substituent.

Examples of the constitutional unit represented by the formula (Y) include constitutional units consisting of arylene groups represented by the formulas (Y-101) to (Y-121), constitutional units consisting of divalent heterocyclic groups represented by the formulas (Y-201) to (Y-206), constitutional units consisting of divalent groups in which at least one arylene group and at least one divalent heterocyclic group are directly bonded, represented by the formulas (Y-301) to (Y-304).

[Chemical Formula 71]

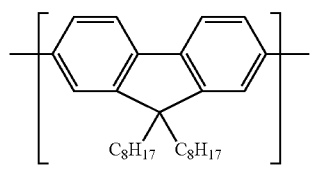
(Y-101)

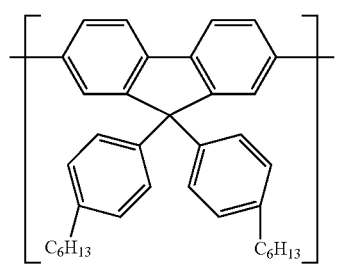
(Y-102)

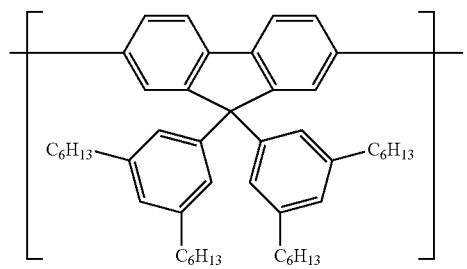
(Y-103)

[Chemical Formula 72]

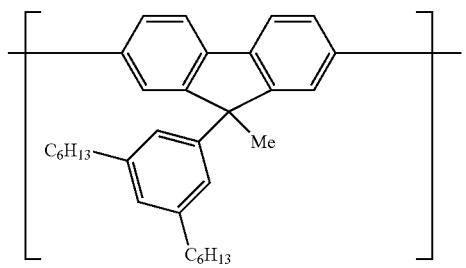
(Y-104)

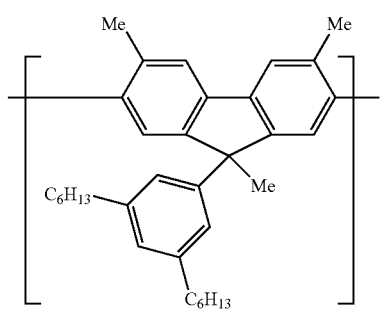
(Y-105)

[Chemical Formula 73]

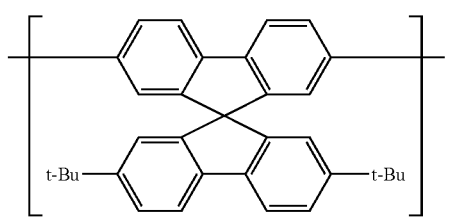
(Y-106)

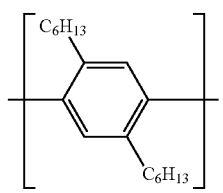
(Y-107)

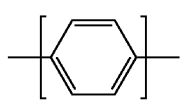
(Y-108)

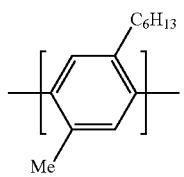
(Y-109)

[Chemical Formula 74]

(Y-110)

(Y-111) 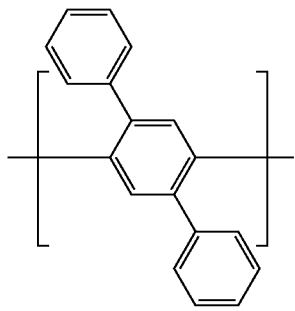
(Y-112) 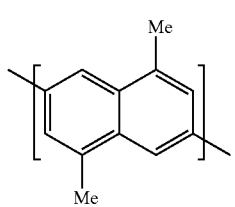
(Y-113) 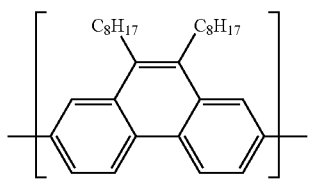
(Y-114) 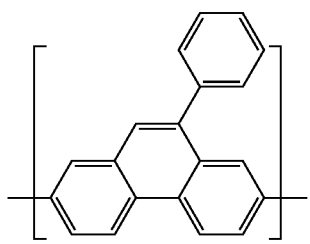
[Chemical Formula 75]
(Y-115) 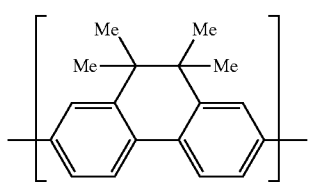
(Y-116)
(Y-117)
(Y-118)
[Chemical Formula 76]
(Y-119) 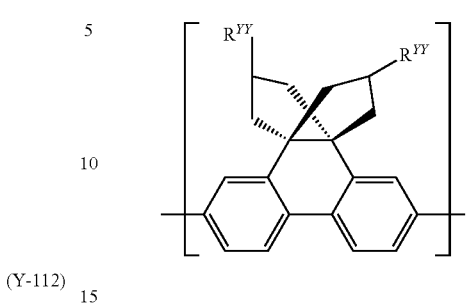
$R^{YY}$ = 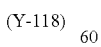
(Y-120) 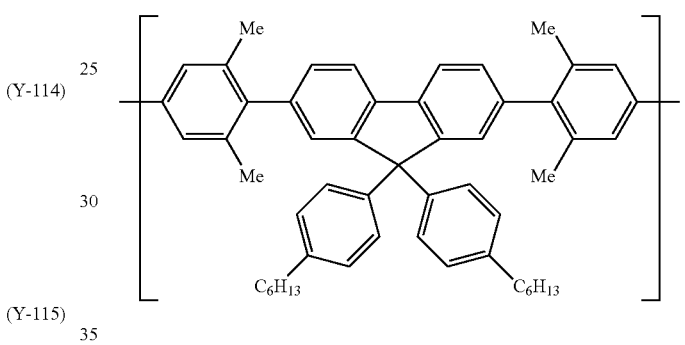
(Y-121) 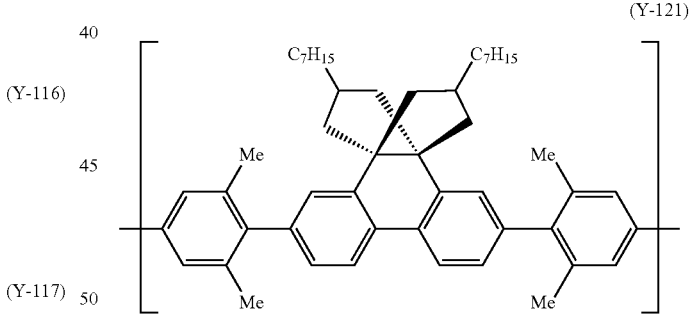
[Chemical Formula 77]
(Y-201) 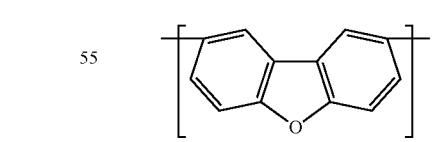
(Y-202) 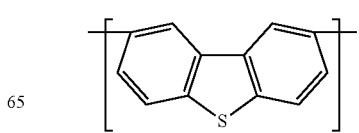

(Y-203) 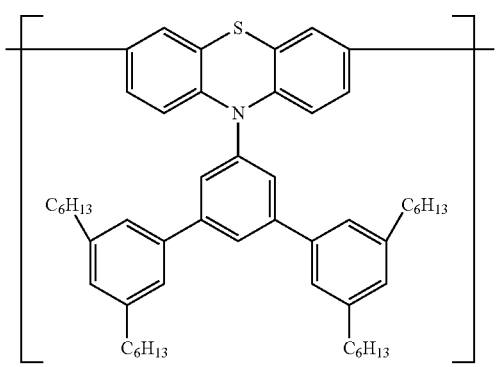
(Y-204) 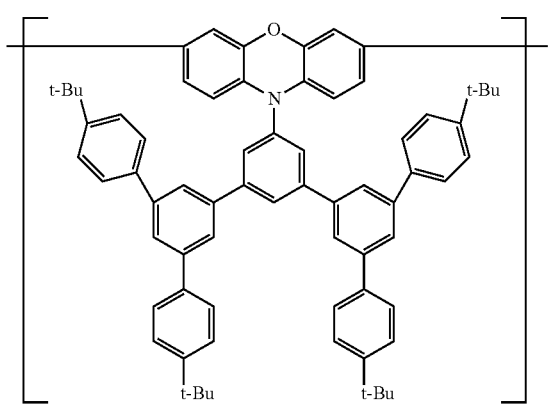
[Chemical Formula 78]
(Y-205) 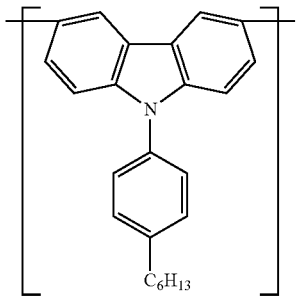
(Y-206) 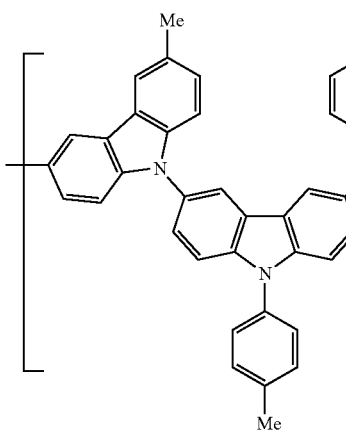
(Y-301) 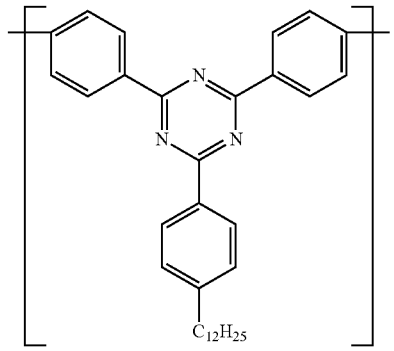
[Chemical Formula 79]
(Y-302) 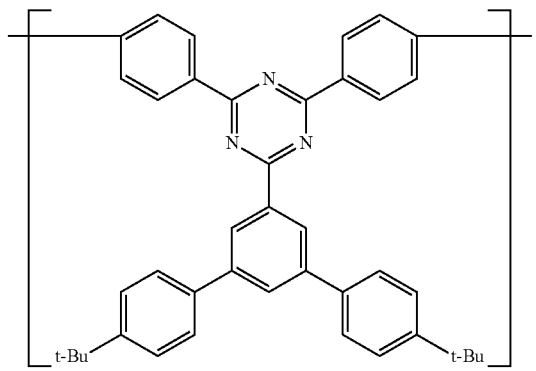
(Y-303) 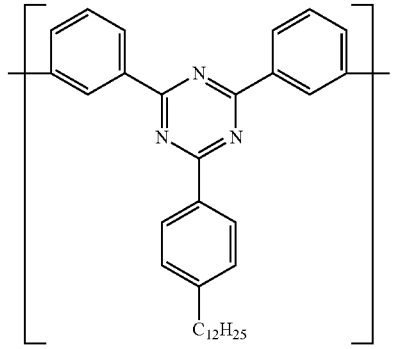
(Y-304) 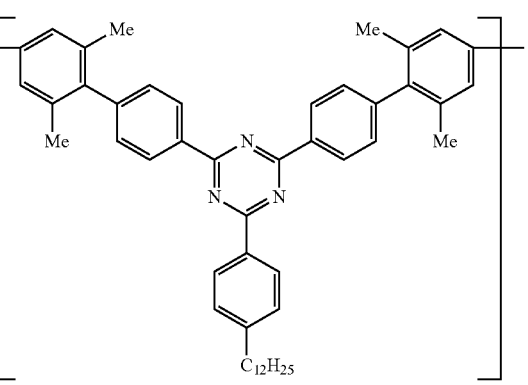
The constitutional unit which is a constitutional unit represented by the formula (Y) wherein $Ar^{Y1}$ is an arylene group is preferably 0.5 to 80% by mol, more preferably 30 to 60% by mol with respect to the total amount of constitutional units contained in the polymer compound, because the luminance lifetime of the light-emitting device is excellent.

The constitutional unit which is a constitutional unit represented by the formula (Y) wherein $Ar^{Y1}$ is a divalent heterocyclic group, or a divalent group in which at least one arylene group and at least one divalent heterocyclic group are directly bonded is preferably 0.5 to 30% by mol, more preferably 3 to 20% by mol with respect to the total amount of constitutional units contained in the polymer compound, because the charge-transporting function of the light-emitting device is excellent.

Only one constitutional unit represented by the formula (Y) may be contained in the polymer host, or two or more may be contained.

It is preferable that the polymer host should further comprise a constitutional unit represented by the formula (X), because the hole-transporting function is excellent.

[Chemical Formula 80]

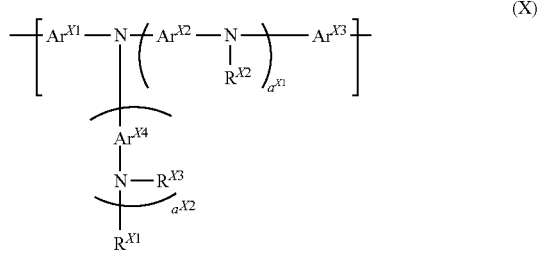

(X)

In the formula, $a^{X1}$ and $a^{X2}$ each independently represent an integer of 0 or larger.

$Ar^{X1}$ and $Ar^{X3}$ each independently represent an arylene group or a divalent heterocyclic group, and a portion or the whole of hydrogen atoms in these groups is optionally replaced with a substituent.

$Ar^{X2}$ and $Ar^{X4}$ each independently represent an arylene group, a divalent heterocyclic group, or a divalent group in which at least one arylene group and at least one divalent heterocyclic group are directly bonded, and a portion or the whole of hydrogen atoms in these groups is optionally replaced with a substituent. In the case where pluralities of $Ar^{X2}$ and $Ar^{X4}$ are present, they are the same or different.

$R^{X1}$, $R^{X2}$ and $R^{X3}$ each independently represent a hydrogen atom, an alkyl group, a cycloalkyl group, an aryl group or a monovalent heterocyclic group, and a portion or the whole of hydrogen atoms in these groups is optionally replaced with a substituent. In the case where pluralities of $R^{X2}$ and $R^{X3}$ are present, they are the same or different.

$a^{X1}$ is preferably 2 or smaller, more preferably 1, because the luminance lifetime of the light-emitting device is excellent.

$a^{X2}$ is preferably 2 or smaller, more preferably 0, because the luminance lifetime of the light-emitting device is excellent.

Each of $R^{X1}$, $R^{X2}$ and $R^{X3}$ is preferably an alkyl group, a cycloalkyl group, an aryl group or a monovalent heterocyclic group, more preferably an aryl group, and a portion or the whole of hydrogen atoms in these groups is optionally replaced with a substituent.

The arylene group represented by $Ar^{X1}$ and $Ar^{X3}$ is more preferably a group represented by the formula (A-1) or the formula (A-9), further preferably a group represented by the formula (A-1), and a portion or the whole of hydrogen atoms in these groups is optionally replaced with a substituent.

The divalent heterocyclic group represented by $Ar^{X1}$ and $A^{X3}$ is more preferably groups represented by the formula (AA-1), the formula (AA-2) or the formulas (AA-7) to (AA-26), and a portion or the whole of hydrogen atoms in these groups is optionally replaced with a substituent.

Each of $Ar^{X1}$ and $Ar^{X3}$ is preferably an arylene group optionally having a substituent.

The arylene group represented by $Ar^{X2}$ and $Ar^{X4}$ is more preferably groups represented by the formula (A-1), the formula (A-6), the formula (A-7), the formulas (A-9) to (A-11) or the formula (A-19), and a portion or the whole of hydrogen atoms in these groups is optionally replaced with a substituent.

A more preferable range of the divalent heterocyclic group represented by $Ar^{X2}$ and $Ar^{X4}$ is the same as the more preferable range of the divalent heterocyclic group represented by $Ar^{X1}$ and $Ar^{X3}$.

More preferable ranges and further preferable ranges of the arylene group and the divalent heterocyclic group in the divalent group in which at least one arylene group and at least one divalent heterocyclic group are directly bonded, represented by $Ar^{X2}$ and $Ar^{X4}$ are the same as the more preferable ranges and the further preferable ranges of the arylene group and the divalent heterocyclic group, respectively, represented by $Ar^{X1}$ and $Ar^{X3}$.

Examples of the divalent group in which at least one arylene group and at least one divalent heterocyclic group are directly bonded, represented by $Ar^{X2}$ and $Ar^{X4}$, include those similar to the divalent group in which at least one arylene group and at least one divalent heterocyclic group are directly bonded, represented by $Ar^{Y1}$, in the formula (Y).

Each of $Ar^{X2}$ and $Ar^{X4}$ is preferably an arylene group optionally having a substituent.

The substituent optionally carried by the group represented by $Ar^{X1}$ to $Ar^{X4}$ and $R^{X1}$ to $R^{X3}$ is preferably an alkyl group, a cycloalkyl group or an aryl group, and a portion or the whole of hydrogen atoms in these groups is optionally further replaced with a substituent.

The constitutional unit represented by the formula (X) is preferably constitutional units represented by the formulas (X-1) to (X-7), more preferably constitutional units represented by the formulas (X-1) to (X-6), further preferably constitutional units represented by the formulas (X-3) to (X-6).

[Chemical Formula 81]

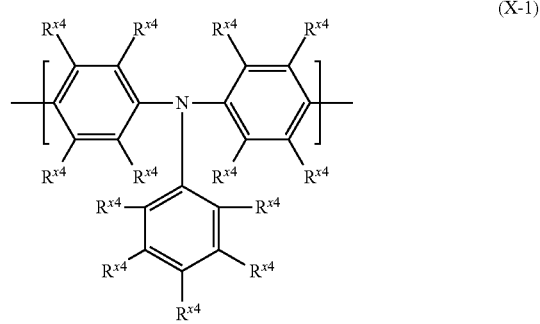

(X-1)

(X-2)

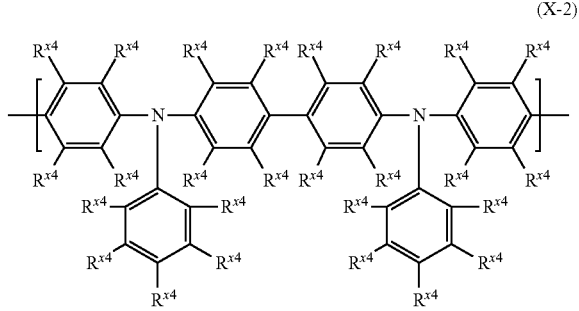

[Chemical Formula 82]

(X-3)

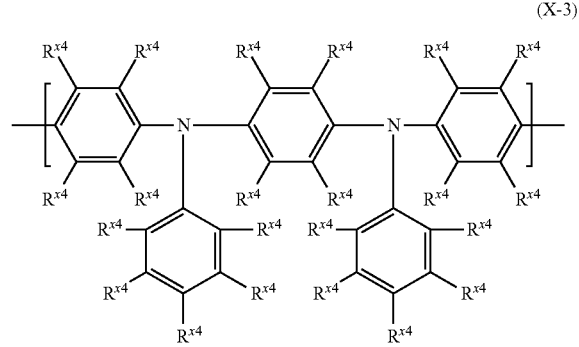

[Chemical Formula 83]

(X-4)

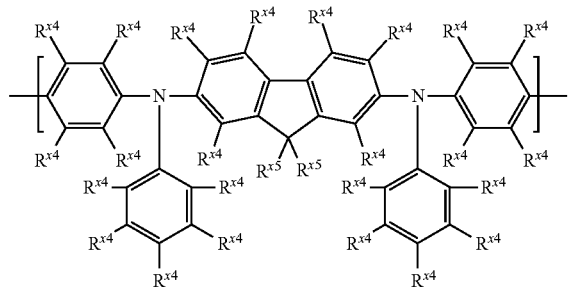

(X-5)

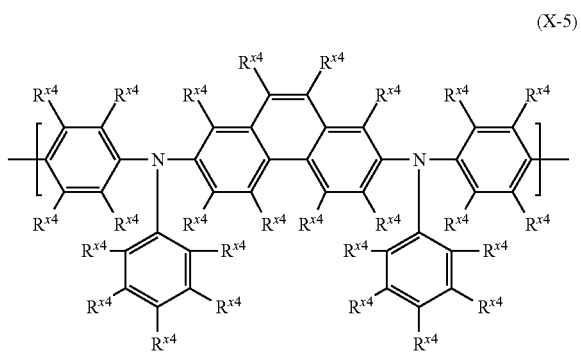

[Chemical Formula 84]

(X-6)

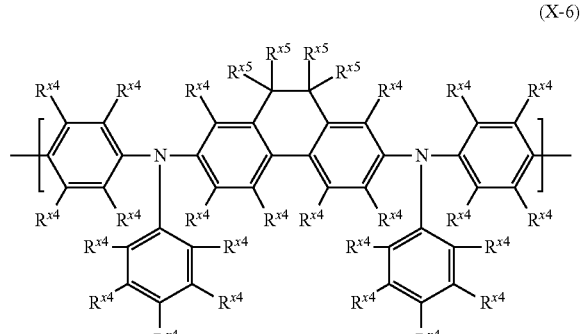

(X-7)

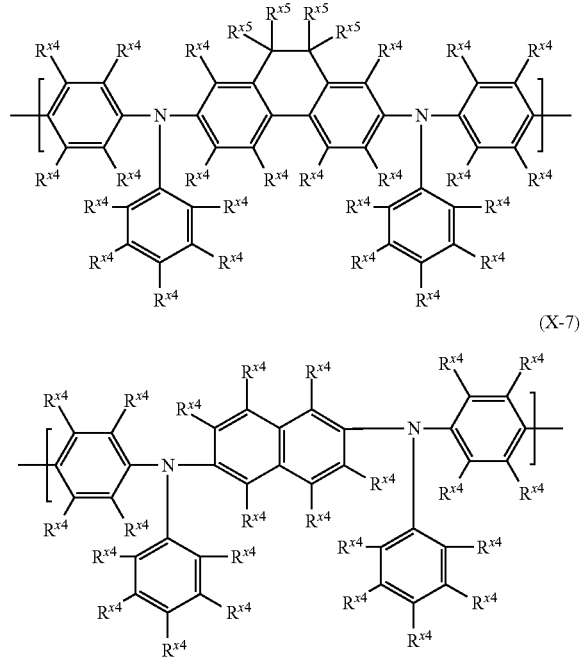

In the formulas, $R^{X4}$ and $R^{X5}$ each independently represent a hydrogen atom, an alkyl group, a cycloalkyl group, an alkoxy group, a cycloalkoxy group, an aryl group, an aryloxy group, a halogen atom, a monovalent heterocyclic group or a cyano group, and a portion or the whole of hydrogen atoms in these groups is optionally replaced with a substituent. A plurality of $R^{X4}$ present are the same or different. A plurality of $R^{X5}$ present are the same or different, and adjacent $R^{X5}$ are optionally bonded to each other to form a ring together with the carbon atoms to which they are attached.

The constitutional unit represented by the formula (X) is preferably 0.1 to 50% by mol, more preferably 1 to 40% by mol, further preferably 5 to 30% by mol, with respect to the total amount of constitutional units contained in the polymer host, because the hole-transporting function is excellent.

Examples of the constitutional unit represented by the formula (X) include constitutional units represented by the formulas (X1-1) to (X1-11), preferably constitutional units represented by the formulas (X1-3) to (X1-10).

[Chemical Formula 85]

(X1-1)

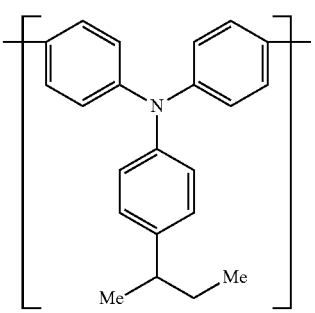

-continued
(X1-2)
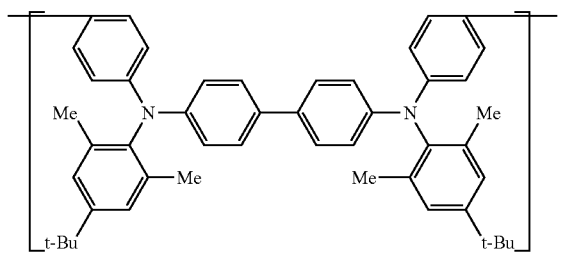
(X1-6)
[Chemical Formula 87]
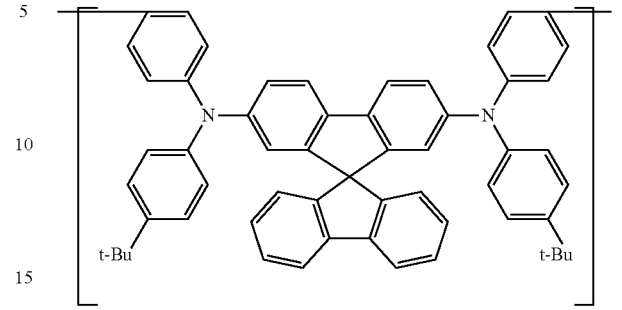
(X1-3)
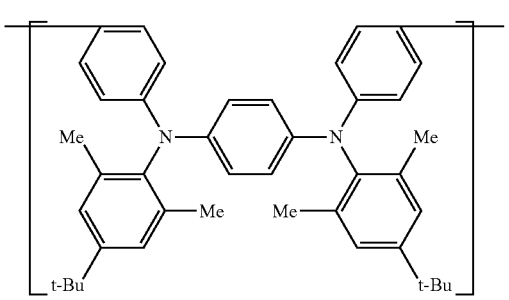
(X1-7)
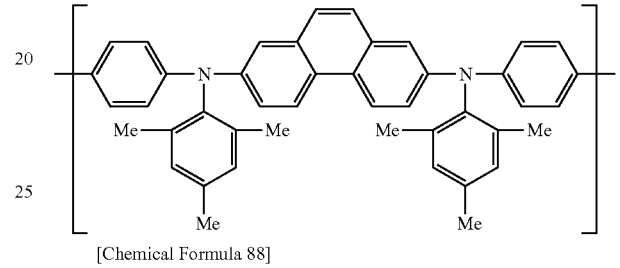
[Chemical Formula 88]
[Chemical Formula 86]
(X1-4)
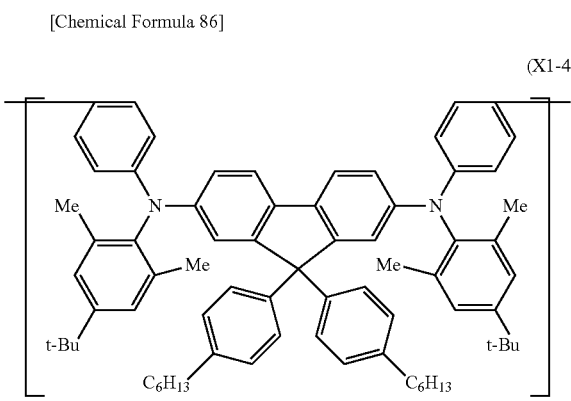
(X1-8)
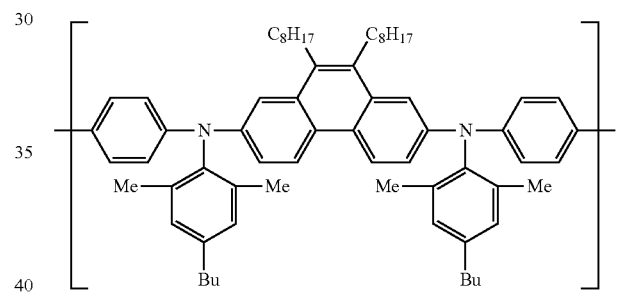
(X1-9)
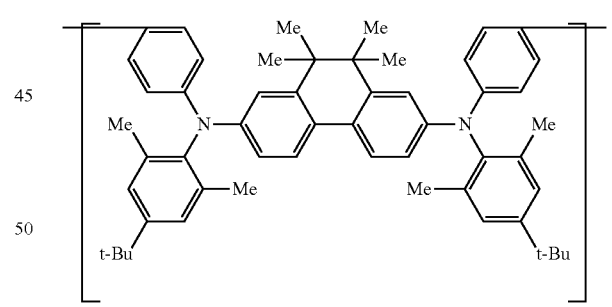
[Chemical Formula 89]
(X1-5)
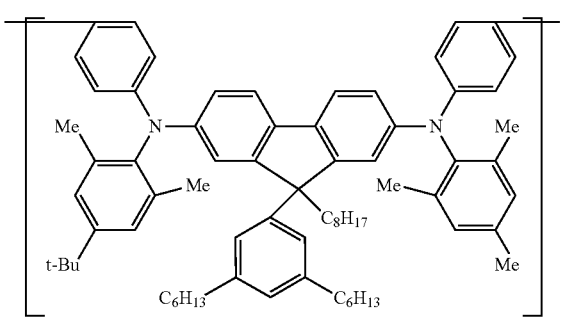
(X1-10)
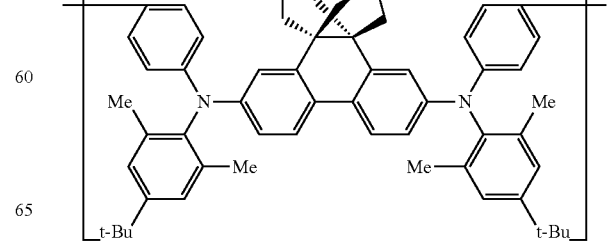

-continued (X1-11)

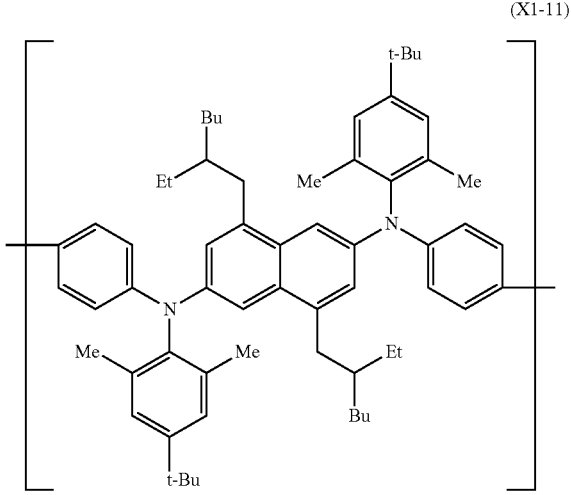

In the polymer host, only one constitutional unit represented by the formula (X) may be contained, or two or more may be contained.

Examples of the polymer host include polymer compounds (P-1) to (P-6) shown in Table 4. In this context, "Others" means a 1.0 constitutional unit other than the constitutional unit represented by the formula (Y), and the constitutional unit represented by the formula (X).

TABLE 4

| Polymer compound | Constitutional unit and molar ratio thereof ||||| |
|---|---|---|---|---|---|
| | Formula (Y) ||| Formula (X) | Others |
| | (Y-1)-(Y-3) p | (Y-4)-(Y-7) q | (Y-8)-(Y-10) r | (X-1)-(X-7) s | t |
| (P-1) | 0.1-99.9 | 0.1-99.9 | 0 | 0 | 0-30 |
| (P-2) | 0.1-99.9 | 0 | 0.1-99.9 | 0 | 0-30 |
| (P-3) | 0.1-99.8 | 0.1-99.8 | 0 | 0.1-99.8 | 0-30 |
| (P-4) | 0.1-99.8 | 0.1-99.8 | 0.1-99.8 | 0 | 0-30 |
| (P-5) | 0.1-99.8 | 0 | 0.1-99.8 | 0.1-99.8 | 0-30 |
| (P-6) | 0.1-99.7 | 0.1-99.7 | 0.1-99.7 | 0.1-99.7 | 0-30 |

In the Table, p, q, r, s and t represent the molar ratio of each constitutional unit. p+q+r+s+t=100, and 100≥p+q+r+s≥70.]

The polymer host may be any of a block copolymer, a random copolymer, an alternate copolymer, and a graft copolymer, or may be in other forms, and it is preferable to be a copolymer prepared by copolymerizing a plurality of raw material monomers.

The polymer host can be produced using a publicly known polymerization method described in Chem. Rev., Vol. 109, p. 8974091 (2009), etc. Examples of the method for producing the polymer host include a method of performing polymerization through coupling reaction using a transition metal catalyst, such as Suzuki reaction, Yamamoto reaction, Buchwald reaction, Stille reaction, Negishi reaction and Kumada reaction.

In the polymerization method, examples of a method for adding monomers include a method of adding the whole amount of the monomers in one portion to a reaction system, a method of adding a portion of the monomers, reacting them, and then adding the remaining monomers in one portion, continuously or in divided portions, and a method of adding the monomers continuously or in divided portions.

Examples of the transition metal catalyst include palladium catalysts and nickel catalysts.

The aftertreatment of the polymerization reaction may be performed, alone or in combination, publicly known methods, for example, a method of removing water-soluble impurities by solution separation, and a method of adding the reaction solution after the polymerization reaction to a lower alcohol such as methanol, and filtering deposited precipitates, followed by drying. In the case where the purity of the polymer host is low, it can be purified by a usual method, for example, crystallization, reprecipitation, continuous extraction with a Soxhlet extractor, or column chromatography.

<Electrode>

The light-emitting device according to the present embodiment has an anode and a cathode.

Examples of the material of the anode include conductive metal oxides and semitransparent metals, preferably indium oxide, zinc oxide, and tin oxide; conductive compounds such as indium tin oxide (ITO) and indium zinc oxide; a complex of silver, palladium, and copper (APC); and NESA, gold, platinum, silver, and copper.

Examples of the material of the cathode include: metals such as lithium, sodium, potassium, rubidium, cesium, beryllium, magnesium, calcium, strontium, barium, aluminum, silver, zinc, and indium; alloys of two or more thereof; alloys of one or more thereof and one or more of silver, copper, manganese, titanium, cobalt, nickel, tungsten, and tin; graphite and graphite intercalation compounds; and metal nanoparticles, metal nanowires, and nanoparticles of conductive metal oxides. Examples of the alloys include a magnesium-silver alloy, a magnesium-indium alloy, a magnesium-aluminum alloy, an indium-silver alloy, a lithium-aluminum alloy, a lithium-magnesium alloy, a lithium-indium alloy, and a calcium-aluminum alloy.

The anode and the cathode may each have a layered structure of two or more layers and may have a structure patterned in a mesh shape.

A publicly known method can be used as a method for preparing the electrodes, and examples include a vacuum deposition method, a sputtering method, an ion plating method, and a method by film formation from a solution (which may employ a mixed solution with a polymer binder). In the case of forming the light-emitting device by a roll-to-roll method, it is preferable to use a method by film formation from a solution.

The light-emitting device according to the present embodiment can be formed on a substrate. The substrate can form an electrode (anode or cathode) on its one surface, and can be a substrate that does not chemically change in forming the organic layers (light-emitting layer and electron-transporting layer). The substrate can be, for example, a substrate made of a material such as glass, plastic, or silicon. The substrate may be transparent, may be semitransparent, or may be opaque, and in the case where the substrate is opaque, it is preferable that an electrode most distant from the substrate should be transparent or semitransparent. In the case of preparing the light-emitting device by a roll-to-roll method, a substrate made of a plastic material is preferable because flexibility is excellent. Examples of the plastic material include polyethylene naphthalate (PEN), polyethersulfone (PES), polyethylene terephthalate (PET), and polycarbonate (PC), and a substrate made of a material of PEN is preferable because heat resistance, a coefficient of thermal expansion, and a water absorption rate are excellent.

The light-emitting device according to the present embodiment may further have a layer other than those described above. For example, the light-emitting device may further have a hole-injecting layer, a hole-transporting layer, and the like.

<Hole-Injecting Layer>

The hole-injecting layer is a layer adjacent to the anode, is a layer having a function of receiving a hole from the anode, and refers to a layer further having, if necessary, any of a function of transporting a hole, a function of supplying a hole to the light-emitting layer, and a function of blocking an electron injected from the cathode. The hole-transporting layer is a layer mainly having a function of transporting a hole and refers to a layer further having, if necessary, any of a function of receiving a hole from the anode, a function of supplying a hole to the light-emitting layer, and a function of blocking an electron injected from the cathode.

In the light-emitting device according to the present embodiment, carbazole derivatives, triazole derivatives, oxazole derivatives, oxadiazole derivatives, imidazole derivatives, fluorene derivatives, polyarylalkane derivatives, pyrazoline derivatives, pyrazol one derivatives, phenylenediamine derivatives, arylamine derivatives, starburst-type amines, phthalocyanine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidine-based compounds, porphyrin-based compounds, polysilane-based compounds, poly(N-vinylcarbazole) derivatives, organosilane derivatives, and polymers containing these; conductive metal oxides such as vanadium oxide, tantalum oxide, tungsten oxide, molybdenum oxide, ruthenium oxide, and aluminum oxide; conductive polymers and oligomers such as polyaniline, aniline-based copolymers, thiophene oligomers, and polythiophene; organic conductive materials such as poly(3,4-ethylenedioxythiophene)-polystyrenesulfonic acid, and polypyrrole and polymers containing these; amorphous carbon; acceptor organic compounds such as tetracyanoquinodimethane derivatives (e.g., 2,3,5,6-tetrafluoro-7,7,8,8-tetracyanoquinodimethane), 1,4-naphthoquinone derivatives, diphenoquinone derivatives, and polynitro compounds; and silane coupling agents such as octadecyltrimethoxysilane can be suitably used as a material forming the hole-injecting layer. These materials may be used as a single component or may be used as a composition consisting of a plurality of components. The hole-injecting layer may have a single-layer structure consisting only of these materials or may have a multilayer structure consisting of a plurality of layers of the same composition or heterogeneous composition. Also, materials listed as a material that can be used in a hole-transporting layer mentioned later can be used in the hole-injecting layer.

In the case of forming the organic compound layers such as the hole-transporting layer and the light-emitting layer following the hole-injecting layer, particularly, in the case of forming both the layers by a coating method, the layer first applied may be dissolved in a solvent contained in a solution of the layer applied later to result in an inability to prepare a layered structure. In this case, a method for insolubilizing the lower layer in a solvent can be used. Examples of the method for performing insolubilization in a solvent include a method of attaching a cross-linking group to the polymer compound and cross-linking it for insolubilization, a method of mixing a low-molecular compound having a cross-linking group having an aromatic ring, typified by aromatic bisazide, as a cross-linking agent, and cross-linking it for insolubilization, a method of mixing a low-molecular compound having a cross-linking group lacking an aromatic ring, typified by an acrylate group, as a cross-linking agent, and cross-linking it for insolubilization, a method of cross-linking the lower layer by photosensitization with ultraviolet light to insolubilize it in an organic solvent that is used in the production of the upper layer, and a method of cross-linking the lower layer by heating to insolubilize it in an organic solvent that is used in the production of the upper layer. The temperature of heating in the case of heating the lower layer is usually 100° C. to 300° C., and the time is usually 1 minute to 1 hour. As other methods, other than cross-linking, for laminating the lower layer without being dissolved, there exists a method using solutions of different polarities in the production of adjacent layers, and, for example, there exists a method using a water-soluble polymer compound in the lower layer and using an oil-soluble polymer compound in the upper layer so that the lower layer becomes no longer soluble even by coating.

Although the optimum value differs depending on the material used and the film thickness of the hole-injecting layer can be selected such that drive voltage and luminous efficiency become moderate values, a thickness at which a pinhole does not occur is necessary, and too large a thickness is not preferable because the drive voltage of the device becomes high. Thus, the film thickness of the hole-injecting layer is usually 1 nm to 1 μm, preferably 2 nm to 500 nm, more preferably 10 nm to 100 nm <Hole-Transporting Layer>

In the light-emitting device according to the present embodiment, examples of the material constituting the hole-transporting layer include: carbazole derivatives, triazole derivatives, oxazole derivatives, oxadiazole derivatives, imidazole derivatives, fluorene derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidine-based compounds, porphyrin-based compounds, polysilane-based compounds, poly(N-vinylcarbazole) derivatives, organosilane derivatives, and polymers containing these structures; conductive polymers and oligomers such as aniline-based copolymers, thiophene oligomers, and polythiophene; and organic conductive materials such as polypyrrole. These materials may be a single component or may be a polymer compound consisting of a plurality of components. The hole-transporting layer may have a single-layer structure consisting only of these materials or may have a multilayer structure consisting of a plurality of layers of the same composition or heterogeneous composition. Also, the materials listed as the material that can be used in the hole-injecting layer can be used in the hole-transporting layer.

In the case where the lower layer is dissolved in a solvent contained in a solution of the layer applied later in forming the organic layers such as the light-emitting layer following the hole-transporting layer by a coating method, the lower layer can be solvent-insoluble by a similar method as in the examples for the film formation method of the hole-injecting layer.

Although the film thickness of the hole-transporting layer differs in optimum value depending on the material used and can be selected such that drive voltage and luminous efficiency become moderate values, a thickness at which a pinhole does not occur is necessary, and too large a thickness is not preferable because the drive voltage of the device becomes high. Thus, the film thickness of the hole-transporting layer is usually 1 nm to 1 µm, preferably 2 nm to 500 nm, more preferably 5 nm to 100 nm.

The material that is used in the hole-transporting layer may employ the light-emitting material listed in the light-emitting layer or a material with a cross-linking group attached to the light-emitting material.

Preferable examples of the layer configuration of the light-emitting device according to the present embodiment include the following configurations:
(a) anode-light-emitting layer-electron-transporting layer-cathode;
(b) anode-hole-injecting layer-light-emitting layer-electron-transporting layer-cathode; and
(c) anode-hole-injecting layer-hole-transporting layer-light-emitting layer-electron-transporting layer-cathode.

Although the light-emitting device according to the present embodiment may be provided with an insulating layer adjacently to an electrode for improvement in close contact with the electrode or improvement in charge injection from the electrode, it is preferable that the electron-transporting layer and the cathode should be adjacent. Also, a thin buffer layer may be inserted to the interface of the hole-transporting layer, the electron-transporting layer or the light-emitting layer for improvement in the close contact of the interface, the prevention of mixing, etc. The order and number of layers to be laminated and the thickness of each layer can be adjusted in light of luminous efficiency and device lifetime.

The light-emitting device according to the present embodiment can be produced, for example, by sequentially laminating each layer on the substrate. Specifically, the light-emitting device can be produced, for example, by disposing the anode on the substrate, disposing layers such as the hole-injecting layer and the hole-transporting layer thereon, disposing the light-emitting layer thereon, disposing a layer of the electron-transporting layer thereon, and further laminating the cathode thereon.

As another production method, the light-emitting device can be produced by disposing the cathode on the substrate, disposing layers such as the electron-transporting layer, the light-emitting layer, the hole-transporting layer, and the hole-injecting layer thereon, and further laminating the anode thereon.

As a further alternative production method, it can be produced by joining the anode or an anode-side base material with each layer laminated on the anode, and the cathode or a cathode-side base material with each layer laminated on the cathode in an opposed manner.

Any of a vacuum deposition method and a coating method may be used in the lamination of each layer.

In the present embodiment, it is preferable to form at least the electron-transporting layer by a coating method. More specifically, it is preferable to provide a composition containing the electron-transporting material and the dopant material, and form a film of the composition by a coating method to form the electron-transporting layer.

The solvent that is used in the coating method can be a solvent that can dissolve or uniformly disperse a material that is used in the formation of a layer. Examples of the solvent include: chlorine-based solvents such as 1,2-dichloroethane, 1,1,2-trichloroethane, chlorobenzene, and o-dichlorobenzene; ether-based solvents such as THF, dioxane, anisole, and 4-methylanisole; aromatic hydrocarbon-based solvents such as toluene, xylene, mesitylene, ethylbenzene, pentylbenzene, hexylbenzene, heptylbenzene, octylbenzene, nonylbenzene, decylbenzene, undecylbenzene, dodecylbenzene cyclohexylbenzene, trimethylbenzene, and 3-phenoxytoluene; aliphatic hydrocarbon-based solvents such as cyclohexane, methylcyclohexane, n-pentane, n-hexane, n-heptane, n-octane, n-nonane, n-decane, n-dodecane, and bicyclohexyl; ketone-based solvents such as acetone, methyl ethyl ketone, cyclohexanone, and acetophenone; ester-based solvents such as ethyl acetate, butyl acetate, ethylcellosolve acetate, methyl benzoate, and phenyl acetate; polyhydric alcohol-based solvents such as ethylene glycol, glycerin, and 1,2-hexanediol; alcohol-based solvents such as methanol, ethanol, isopropyl alcohol, 1-butanol, tert-butyl alcohol, and cyclohexanol; sulfoxide-based solvents such as dimethyl sulfoxide; amide-based solvents such as N-methyl-2-pyrrolidone and N,N-dimethylformamide; fluorinated alcohol solvents such as 2,2,3,3-tetrafluoropropanol, 1,1,1-trifluoro-2-propanol, 1,1,1,3,3,3-hexafluoro-2-propanol, 2,2,3,3,4,4-hexafluorobutanol, 2,2,3,3,4,4,4-heptafluoro-1-butanol, 2,2,3,3,3-pentafluoro-1-propanol, 3,3,4,4,5,5,5-heptafluoro-2-pentanol, 2,2,3,3,4,4,5,5-octafluoro-1-pentanol, 3,3,4,4,5,5,6,6,6-nonafluoro-1-hexanol, and 2,2,3,3,4,4,5,5,6,6,7,7-dodecafluoroheptanol; and water. One solvent may be used alone, or two or more may be used in combination.

Examples of the film formation method include coating methods such as a spin coating method, a casting method, a micro-gravure printing method, a gravure printing method, a bar coating method, a roll coating method, a wire bar coating method, a dip coating method, a slit coating method, a cap coating method, a spray coating method, a screen printing method, a flexographic printing method, an offset printing method, an inkjet printing method, and a nozzle coating method, and it is preferable to use a slit coating method or an inkjet printing method.

In the coating method, film formation is performed using a coating solution containing the electron-transporting material, the dopant material and the solvent. The viscosity of the coating solution can be adjusted by the type of the printing method, but is preferably 1 to 30 mPa·s, more preferably 3 to 25 mPa·s, at 25° C. in the case of being applied to a printing method in which the coating solution passes through a discharge apparatus, such as an inkjet printing method, because clogging or curved flight at the time of discharge is less likely to occur.

The content of the solvent in the coating solution is usually 1000 to 100000 parts by mass, preferably 2000 to 20000 parts by mass, with respect to 100 parts by mass of the material that is used in the formation of the layer.

A method for forming a layer other than the electron-transporting layer is not particularly limited and can be a publicly known method. In the case where the material that is used in the formation of each layer is a low-molecular compound, it can be formed by, for example, a vacuum deposition method from a powder or a method by film formation from a solution or a melted state. In the case where the material that is used in the formation of each layer is a polymer compound, it can be formed by, for example, a method by film formation from a solution or a melted state.

The order, number, and thicknesses of layers to be laminated can be adjusted in light of luminous efficiency and device lifetime.

In order to obtain planar light emission using the light-emitting device, a planar anode and cathode can be arranged so as to overlap. In order to obtain patterned light emission, there is a method of establishing a mask provided with a patterned window on the surface of a planar light-emitting device, a method of forming a layer desired to be a non-light-emitting part as an exceedingly thick film to render the layer substantially non-light-emitting, or a method of forming an anode or a cathode, or both the electrodes in a patterned form. A segment-type display device that can display numbers, characters, etc. is obtained by forming a pattern by any of these methods and arranging some electrodes so as to independently switch ON and OFF. In order to prepare a dot matrix display device, the anode and the cathode can both be formed in a stripe state and orthogonally arranged. Partial color display or multicolor display becomes possible by a method of distinctively applying a plurality of types of polymer compounds differing in emitted light color, or a method using a color filter or a fluorescence conversion filter. The dot matrix display device may be passively driven and may be actively driven in combination with TFT or the like. These display devices can be used in display screens of computers, televisions, portable terminals, etc. The planar light-emitting device can be suitably used as a planar light source for a backlight of a liquid-crystal display device, or a planar light source for illumination. It can also be used as a curved light source, and display device as long as a flexible substrate is used.

Although the preferable embodiments relating to the light-emitting device of the present invention are described above, the present invention is not limited by the embodiments described above.

One aspect of the present invention relates to a method for producing an electron-transporting layer, comprising a step of doping the electron-transporting material with the heterocyclic compound.

One aspect of the present invention also relates to a method for producing a light-emitting device having an anode, a light-emitting layer, an electron-transporting layer and a cathode, comprising: a step of providing a composition containing the electron-transporting material and the dopant material; and a step of forming a film of the composition by a coating method to form the electron-transporting layer.

EXAMPLES

Although the present invention will be described below in detail with reference to Examples, the present invention is not limited by these Examples.

<Measurement of NMR>

The measurement of NMR was performed by the following method.

Approximately 10 mg of a measurement sample was dissolved in approximately 0.7 mL of a deuterated solvent and subjected to measurement using a NMR apparatus (manufactured by Agilent Technologies, Inc., trade name: INOVA 300 or MERCURY 400VX).

<TLC-MS>

The measurement of TLC-MS was performed by the following method.

A measurement sample was dissolved at an arbitrary concentration in toluene, tetrahydrofuran or chloroform, applied onto a TLC plate for DART (manufactured by Techno Applications Co., Ltd., trade name: YSK5-100), and subjected to measurement using TLC-MS (manufactured by JEOL Ltd., trade name: JMS-T100TD (The AccuTOF TLC)). The helium gas temperature at the time of measurement was adjusted in the range of 200 to 400° C.

<Analysis by HPLC>

A value of high-performance liquid chromatography (HPLC) area percentage was used as an index for the purity of a compound. This value is a value at 254 nm in HPLC (manufactured by Shimadzu Corp., trade name: LC-20A) unless otherwise specified. In this respect, the compound to be measured was dissolved in tetrahydrofuran or chloroform so as to attain a concentration of 0.01 to 0.2% by weight, and 1 to 10 μL was injected to HPLC according to the concentration. Acetonitrile and tetrahydrofuran were used in a mobile phase of HPLC and injected at a flow rate of 1 mL/min in the gradient analysis of acetonitrile/tetrahydrofuran=100/0 to 0/100 (volume ratio). The column employed SUMIPAX ODS Z-CLUE (manufactured by Sumika Chemical Analysis Service, Ltd.) or an ODS column having equivalent performance. A photodiode array detector (manufactured by Shimadzu Corp., trade name: SPD-M20A) was used as a detector.

<Liquid Chromatography-Mass Spectrometry>

Liquid chromatography-mass spectrometry (LC-MS) was performed by the following method.

A measurement sample was dissolved in chloroform or THF so as to attain a concentration of approximately 2 mg/mL, and approximately 1 μL was injected to LC-MS (manufactured by Agilent Technologies, Inc., trade name: 1100LCMSD). Acetonitrile and THF were used at varying ratios in a mobile phase of LC-MS, and injected at a flow rate of 0.2 mL/min. The column employed SUMIPAX ODS Z-CLUE (φ4.6×250 mm, 3 μm, manufactured by Sumika Chemical Analysis Service, Ltd.).

<Obtainment of Compound>

TAZ (3-(biphenyl-4-yl)-5-(4-tert-butylphenyl)-4-phenyl-4H-1,2,4-triazole) was used as the electron-transporting material. TAZ employed one purchased from Sigma-Aldrich Co. LLC. The LUMO level of the electron-transporting material TAZ was −2.0 eV.

Synthesis Example 1

Compound A-1 represented by the formula (A-1) was synthesized by the following methods of (i) to (iv).

[Chemical Formula 90]

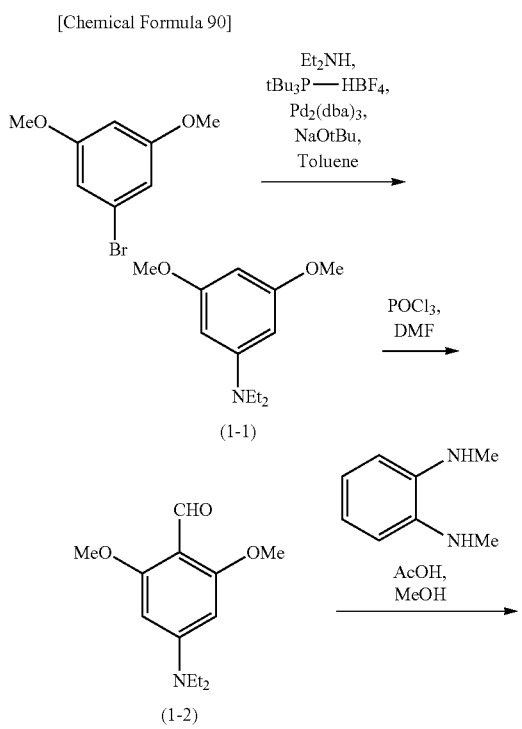

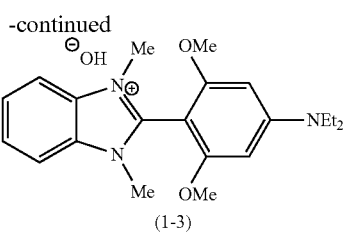

(1-3)

[Chemical Formula 91]

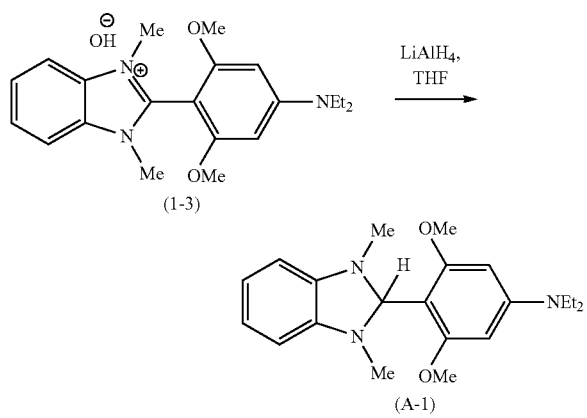

(i) Compound (1-1)

20.14 g of 3,5-dimethoxy-1-bromobenzene, 1.68 g of Pd$_2$(dba)$_3$, 238 g of tBu$_3$P—HBF$_4$, and 13.28 g of NaOtBu were taken into a flask, and the atmosphere within the flask was purged with nitrogen. 200 ml of toluene (dehydrated) was added thereto and heated to 80° C. in an oil bath. 14.4 ml of diethylamine was added dropwise thereto, incubated for 2 hours, and stirred. The resultant was cooled to 0° C., and 100 ml of water was added dropwise thereto for solution separation and extracted with 100 ml of toluene twice. The organic phases were combined and dried over magnesium sulfate, and as a result of distilling off the solvent, 24.07 g of a crude product was obtained. 15.98 g of compound (1-1) was obtained by purification (developing solvent: hexane:ethyl acetate) using silica gel column chromatography.

Analysis results about the obtained compound (1-1) were as follows.

$^1$H NMR. (CDCl$_3$) δ 1.15 (6H, t), 3.31 (4H, q), 3.77 (6H, s), 5.84-5.87 (3H, m)

TLC-MS (DART) 210.12 ([M+H]$^+$, Exact Mass: 209.14)

(ii) Synthesis of Compound (1-2)

The atmosphere within a flask was purged with nitrogen, and 18 ml of dehydrated DMF was added thereto. 4.8 ml of phosphorus oxychloride was added dropwise thereto while the internal temperature was kept at 10° C. or lower by cooling in an ice bath. After incubation for 30 minutes, a solution of 10.00 g of compound (1-1) dissolved in 6.0 ml of DMF was added dropwise thereto while the internal temperature was kept at 10° C. or lower. After stirring for 2.5 hours, the reaction product was added dropwise to a beaker supplemented with 42 g of ice water, and stirred for 2 hours. The aqueous phase was extracted with 125 ml of chloroform three times, and the organic phases were combined and washed with 100 ml of water and 100 ml of saturated saline. After drying over magnesium sulfate, the solvent was distilled off to obtain 27.85 g of a crude product.

12.13 g of compound (1-2) was obtained by purification (developing solvent: hexane:ethyl acetate) using silica gel column chromatography.

Analysis results about the obtained compound (1-2) were as follows.

$^1$H-NMR (CDCl$_3$) δ 1.24 (6H, t), 3.42 (4H, q), 3.87 (6H, s), 5.73 (2H, s), 10.23 (1H, s)

TLC-ms (DART) 238.14 ([M+H]$^+$, Exact Mass: 237.14)

(iii) Synthesis of Compound (1-3)

3.01 g of N,N'-dimethyl-o-phenylenediamine and 5.00 g of compound (1-2) were taken into a flask, and 42 ml of methanol was added thereto and stirred. 625 mg of acetic acid was added dropwise thereto and then heated at 70° C. for 14 hours in an air atmosphere. The reaction product was concentrated, supplemented with 10 ml of water, and washed three times with 50 ml of toluene. The aqueous phase was concentrated, then dissolved in 150 ml of chloroform, dried over magnesium sulfate, and filtered, then the solvent was distilled off, and as a result of drying in a vacuum dryer, 6.16 g of compound (1-3) was obtained.

Analysis results about the obtained compound (1-3) were as follows.

$^1$H-NMR (CDCl$_3$) δ 1.29 (6H, t), 3.48 (4H, q), 3.83 (6H, s), 3.88 (6H, s), 5.91 (2H, s), 7.64-7.67 (2H, m), 7.88-7.92 (2H, m)

(iv) Synthesis of Compound A-1

5.45 g of compound (1-3) was taken into a flask, and after the atmosphere within the flask was purged with nitrogen, 109 ml of dehydrated THF was added thereto. 571 mg of lithium aluminum hydride was added thereto in small portions while the internal temperature was kept at 30° C. or lower in a water bath, and stirred for 3 hours. 750 g of ice water was taken, and the reaction solution was added dropwise thereto. Extraction was performed with 750 ml of toluene three times, the organic phases were combined, dried over sodium sulfate, and then filtered, and as a result of distilling off the solvent, 2.91 g of compound A-1 was obtained.

Analysis results about the obtained compound A-1 were as follows.

$^1$H-NMR (CDCl$_3$) δ 1.20 (6H, t), 2.55 (6H, s), 3.36 (4H, q), 3.67 (6H, brs), 5.86 (2H, s), 6.07 (1H, s), 6.20-6.23 (2H, m), 6.53-6.56 (2H, m)

TLC-MS (DART) 355.24 ([M]$^+$, Exact Mass: 355.23)

<Synthesis Example 2> Synthesis of Monomers CM1 to CM9

Monomers CM1 to CM9 were synthesized according to the methods described in the literatures described below, and those that exhibited a HPLC area percentage value of 99.5% or more were used.

The monomer. CM1 was synthesized according to the description of Macromolecules 2005, 38, 5416-5424.

The monomer CM2 was synthesized according to the method described in Japanese Unexamined Patent Publication No. 2010-189630.

The monomer CM3 was synthesized according to the method described in International Publication No. WO 2013/191088.

The monomer CM4 was synthesized according to the method described in International Publication No. WO 2012/086671.

The monomer CM5 was synthesized according to the method described in Japanese Unexamined Patent Publication No. 2011-174061.

The monomer CM6 was synthesized according to the method described in International Publication No. WO 2002/045184.

The monomer CM7 was synthesized according to the method described in Japanese Unexamined Patent Publication No. 2008-106241.

The monomer CM8 was synthesized according to the method described in Japanese Unexamined Patent Publication No. 2003-226744.

The monomer CM9 was synthesized according to the method described in Japanese Unexamined Patent Publication No. 2010-189630.

[Chemical Formula 92]

CM1

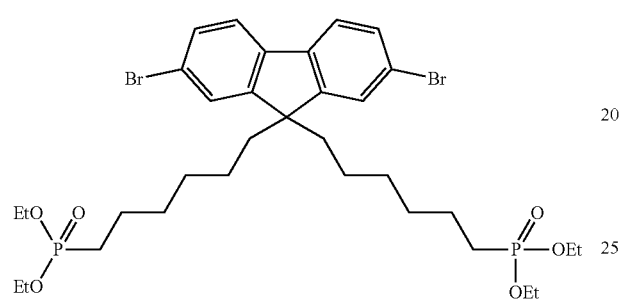

[Chemical Formula 93]

CM2

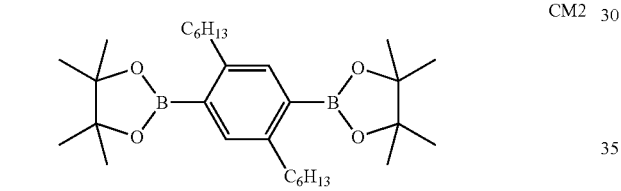

[Chemical Formula 94]

CM3

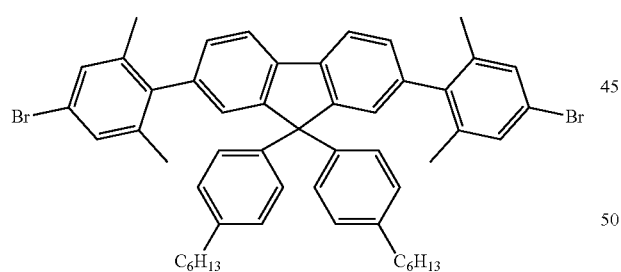

CM4

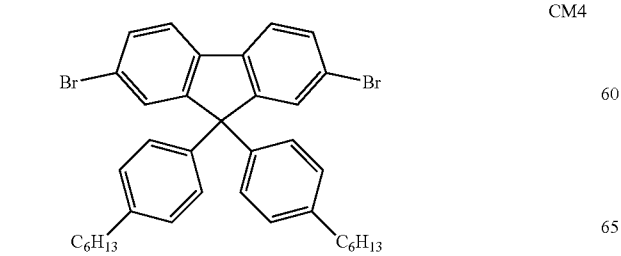

CM5

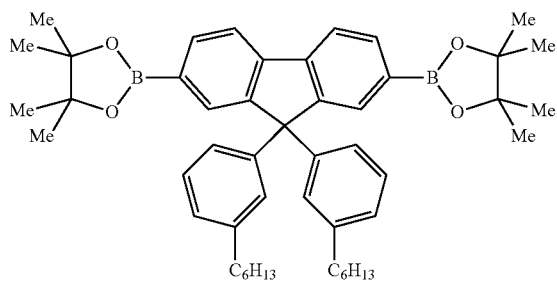

[Chemical Formula 95]

CM6

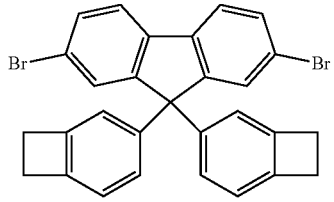

CM7

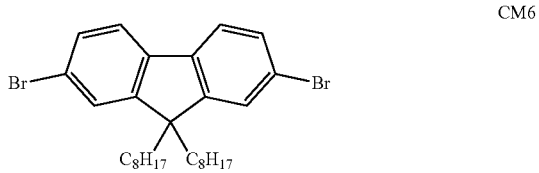

[Chemical Formula 96]

CM8

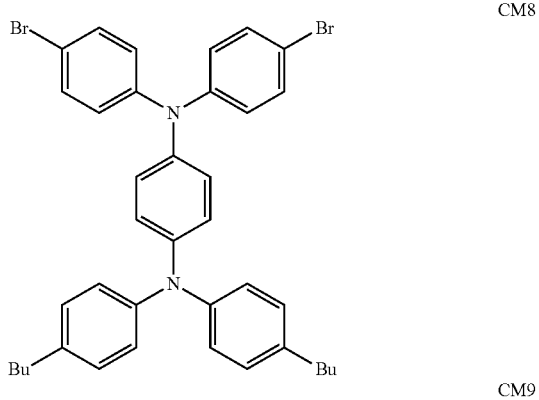

CM9

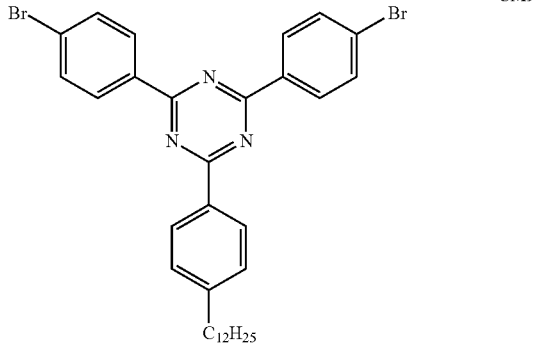

<Synthesis Example 3> Synthesis of Phosphorescent Compounds MC1 and MC2

Phosphorescent compounds MC1 and MC2 were synthesized according to the methods described in the literatures described below, and those that exhibited a HPLC area percentage value of 99.5% or more were used.

The phosphorescent compound MC1 was synthesized according to the method described in International Publication No. WO 2009/131255. The electron affinity of the phosphorescent compound MC1 is 2.8 eV.

The phosphorescent compound MC2 was synthesized according to the method described in Japanese Unexamined Patent Publication No. 2013-147551. The electron affinity of the phosphorescent compound MC2 is 2.4 eV.

[Chemical Formula 97]

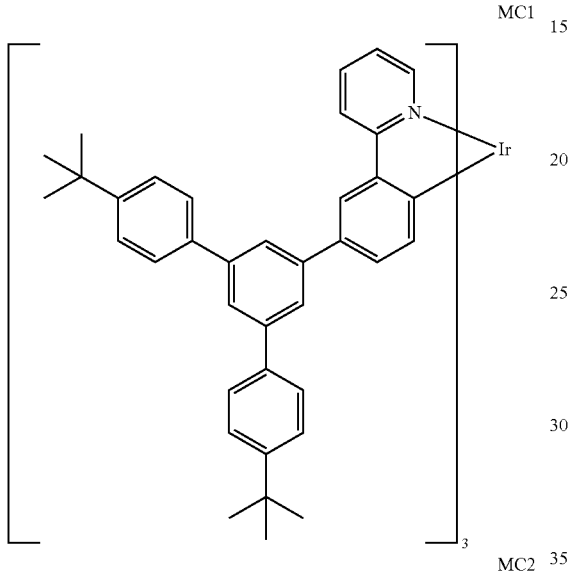

MC1

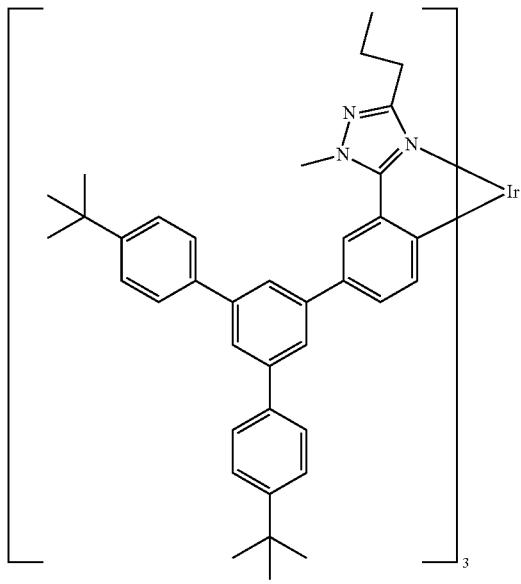

MC2

<Synthesis Example 4> Synthesis of Polymer Compound HT1

Polymer compound was synthesized by the following steps 1 and 2.

(Step 1) After an inert gas atmosphere was created within a reaction container, monomer CM5 (185 g), monomer CM6 (35.9 g), monomer CM7 (20.1 g), monomer CM8 (104 g), dichlorobis(triphenylphosphine)palladium (177 mg) and toluene (4.3 kg) were added and heated to 100° C. An aqueous solution containing 20% by weight of tetraethylammonium hydroxide (873 g) was added thereto and then stirred at 100° C. for 5 hours. Phenylboronic acid (3.08 g) and toluene (120 g) were added thereto and stirred at 100° C. for 14 hours.

(Step 2) After the aqueous phase was removed from the reaction solution, an aqueous sodium diethyldithiacarbamate solution and toluene were added thereto and stirred at 40° C. for 3 hours. Then, after cooling to room temperature, the aqueous phase was removed to thereby obtain an organic phase. The obtained organic phase was washed twice with 10% by weight of hydrochloric acid, twice with an aqueous solution containing 3% by weight of ammonia and twice with ion-exchange water. The washed organic phase was purified by passing through an alumina column and a silica gel column in order. Since the obtained purified solution was added dropwise to methanol and as a result of stirring, precipitates were formed, the precipitates were taken by filtration and dried to thereby obtain polymer compound HT1 (204 g). Mn of the polymer compound HT1 was $6.7 \times 1.0^4$, and Mw was $2.3 \times 10^5$.

The polymer compound HT1 is a copolymer in which a constitutional unit derived from monomer CM5, a constitutional unit derived from monomer CM6, a constitutional unit derived from monomer CM7, and a constitutional unit derived from monomer CM8 are constituted at a molar ratio of 50:12.5:7.5:30, in terms of a theoretical value determined from the amounts of the added raw materials.

<Synthesis Example 5> Synthesis of Polymer Compound HP1

In an inert gas atmosphere, monomer CM2 (2,5-bis(4,4,5,5-tetramethyl-1,3,2-dioxaborolan-2-yl)-1,4-dihexylbenzene) (8.182 g), monomer CM4 (9,9-bis(4-n-hexylphenyl)-2,7-dibromofluorene) (8.508 g), monomer CM9 (2,4-bis(4-bromophenyl)-6-(4-n-dodecylphenyl)-1,3,5-triazine) (2.097 g), and toluene (250 mL) were mixed, and stirred while heated. Palladium acetate (3.7 mg) and tris(2-methoxyphenyl)phosphine (23.2 mg) were added thereto and heated to 100° C. An aqueous solution containing 20% by weight of tetraethylammonium hydroxide (61.3 g) was added dropwise to the obtained solution and heated to reflux for 8 hours.

Next, phenylboric acid (0.20 g), palladium acetate (3.7 mg), tris(2-methoxyphenyl)phosphine (23.3 mg), and an aqueous solution containing 20% by weight of tetraethylammonium hydroxide (58.3 g) were added thereto and heated to reflux for 15 hours.

After the aqueous phase was removed, sodium N,N-diethyldithiocarbamate trihydrate (9.31 g) and ion-exchange water (60 mL) were added thereto and stirred at 40° C. for 3 hours. After the organic phase was separated from the aqueous phase, the organic phase was washed in the order of once with ion-exchange water, twice with 10% by weight of hydrochloric acid, twice with an aqueous solution containing 3% by weight of ammonia and twice with ion-exchange water. The solution of the organic phase was passed through a column packed with silica gel and alumina through which toluene passed in advance, and the passed-through solution was added dropwise to methanol to deposit precipitates. The precipitates were taken by filtration and then dried to obtain 9.80 g of polymer compound HP1. Mn of the polymer compound HP1 was $9.2 \times 10^4$, and Mw was $2.3 \times 10^5$.

The polymer compound HP1 is a copolymer in which a constitutional unit derived from monomer CM2, a constitutional unit derived from monomer CM4, and a constitutional unit derived from monomer CM9 are constituted at a molar ratio of 50:40:10, in terms of a theoretical value determined from the amounts of the added raw materials.

<Synthesis Example 6> Synthesis of Polymer Compound HP2

Polymer compound HP2 was synthesized by the following steps 1 to 4.
(Step 1) After an inert gas atmosphere was created within a reaction container, monomer CM2 (2.2 g), monomer CM3 (1.3 g), dichlorobis(tris-o-methoxyphenylphosphine)palladium (2.3 mg) and toluene (55 mL) were added and heated to 105° C.
(Step 2) Then, an aqueous solution containing 20% by weight of tetraethylammonium hydroxide (9.1 g) was added dropwise thereto and refluxed for 4 hours.
(Step 3) Then, 2-isopropylphenylboronic acid (0.47 g) and dichlorobis(tris-o-methoxyphenylphosphine)palladium (2.2 mg) were added thereto and refluxed for 16 hours.
(Step 4) Then, an aqueous sodium diethyldithiacarbamate solution was added thereto and stirred at 85° C. for 5 hours. The obtained reaction solution was cooled and then washed with hydrochloric acid, ammonia water, and ion-exchange water, and as a result of adding dropwise the obtained organic phase to methanol, precipitates were formed. The precipitates were taken by filtration, and a solid obtained by drying was dissolved in toluene and purified by passing through an alumina column and a silica gel column in order through which toluene passed in advance. The obtained purified solution was added dropwise to methanol and as a result of stirring, precipitates were formed. The precipitates were taken by filtration and dried to thereby obtain polymer compound HP2 (2.3 g). Mn of the polymer compound HP2 was $7.4 \times 10^4$, and Mw was $2.3 \times 10^5$. The electron affinity of the polymer compound HP2 was 2.59 eV or less.

The polymer compound HP2 is a copolymer in which a constitutional unit derived from monomer CM2 and a constitutional unit derived from monomer CM3 are constituted at a molar ratio of 50:50, in terms of a theoretical value determined from the amounts of the added raw materials.

<Synthesis Example 7> Synthesis of Monomer CM1'

Monomer CM1' was synthesized by the following method.

[Chemical Formula 98]

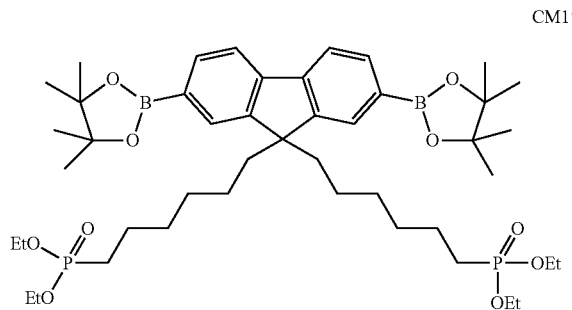

CM1'

11.73 g of monomer CM1, 8.54 g of bispinacolatodiboron, 63.7 mg of a 1,1'-bis(diphenylphosphino)ferrocene palladium dichloride-dichloromethane complex, 9.03 g of potassium acetate, and 60 ml of dimethoxyethane (dehydrated) were added to a flask, and the atmosphere within the flask was purged with nitrogen. The resultant was dipped in an oil bath of 100° C., and heated and stirred for 3 hours. After standing to cool to 40° C., 50 ml of water and 1.50 ml of toluene were added thereto to perform solution separation. 1.02 g of active carbon was added to the organic phase and stirred at room temperature for 1 hour. The resultant was filtered through a glass filter covered with Celite 545, and washed with toluene. The solvent in the filtrate and the washes was distilled off, and the resultant was dried under reduced pressure at 50° C. for 12 hours in a vacuum dryer to obtain 17.36 g of a crude product. Recrystallization from a heptane solvent were repeated three times to obtain 7.86 g of monomer CM1'.

Analysis results about the obtained monomer CM1' were as follows.
TLC-MS (DART) 859.57 ([M+H]$^+$, Exact Mass: 858.49)
$^1$H-NMR (300 MHz, CDCl$_3$) δ 0.48-0.58 (4H, m), 0.98-1.15 (8H, m), 1.23-1.29 (16H, m) 1.39 (24H, s), 1.51-1.63 (4H, m), 1.96-2.02 (4H, m) 3.99-4.07 (8H, m), 7.71 (2H, d), 7.72 (2H, s), 7.80 (2H, d)

<Synthesis Example 8> Synthesis of Electron-Transporting Material HE1

10.2 mg (0.025 mmol) of Aliquat 336, 770.3 mg of monomer CM1, and 767.1 mg of monomer CM1' were dissolved in 30 ml of toluene and added to a flask. After nitrogen bubbling for 30 minutes, 1.0 mg of dichlorobis[tri(o-methoxyphenyl)phosphine]palladium(II) was dissolved in a small amount of toluene and added thereto, and after the atmosphere within the flask was purged with nitrogen, the resultant was dipped in an oil bath of 105° C. and heated. 11 ml of an aqueous solution containing 5 wt % of sodium carbonate was added dropwise thereto, and then heated and stirred for 4 hours. Then, 46.6 mg of phenylboric acid was added thereto, and the resultant was dipped in an oil bath of 105° C. and heated and stirred for 17 hours.

After the reaction solution was allowed to cool, the aqueous phase was removed, and solution separation and washing were performed by adding 20 ml of water. Hexane was taken into a 2 L beaker and stirred, and the polymer solution was added dropwise thereto and precipitated. The obtained solid was washed with hexane and dried under reduced pressure for 12 hours or longer in a vacuum dryer of 50° C. Hexane was taken into a 2 L beaker and stirred, and a polymer solution of the thus-obtained polymer dissolved in isopropanol was added dropwise thereto and reprecipitated. The obtained solid was washed with hexane, and as a result of drying under reduced pressure for 12 hours or longer in a vacuum dryer of 50° C., 0.929 g of electron-transporting material HE1 was obtained. The LUMO level of the electron-transporting material HE1 was −2.0 ev.

<Synthesis Example 9> Synthesis of Electron-Transporting Material HE2

After an inert gas atmosphere was created in a flask, 8.7 g (0.022 mmol) of 2,8-dibromo-4-butyldibenzothiophene and 8.1 g (0.048 mmol) of 4-aza-1H-carbazole were dissolved in 218 mL of dimethyl sulfoxide. 1.3 g (0.009 mmol) of Cu$_2$O and 16.7 g (0.079 mmol) were added, then 3.2 g (0.018 mmol) of dipivaloylmethane was added, and the resultant was dipped in an oil bath of 150° C. and heated.

After the reaction solution was allowed to cool, 87 mL of toluene and 87 mL of water were added thereto, and the mixture was filtered through a glass filter covered with Celite 545, followed by solution separation and washing. The obtained organic phase was concentrated and purified by passing through a silica gel column, subsequently active carbon, and finally Celite 545. The solvent of the obtained solution was distilled off, and as a result of drying under reduced pressure for 12 hours or longer in a vacuum dryer of 50° C., 9.4 g of electron-transporting material HE2 was obtained.

The LUMO level of the electron-transporting material HE2 was −2.0 ev.

<Example 1> Preparation and Evaluation of Light-Emitting Device D1

(i) Formation of Anode and Hole-Injecting Layer

An ITO film was attached at a thickness of 45 nm to a glass substrate by the sputtering method to thereby form an anode. A film of a hole-injecting material (ND-3202) manufactured by Nissan Chemical Industries, Ltd. was formed at a film thickness of 65 nm on the anode by the spin coating method. The substrate with the film of the hole-injecting material formed was heated at 50° C. for 3 minutes on a hot plate to volatilize the solvent, and subsequently, a hole-injecting layer was formed by heating at 230° C. for 15 minutes on a hot plate.

(ii) Formation of Hole-Transporting Layer

Polymer compound HT1 was dissolved at a concentration of 0.7% by weight in xylene. A film was formed at a thickness of 20 nm on the hole-injecting layer by the spin coating method using the obtained xylene solution, and in a nitrogen gas atmosphere, a hole-transporting layer was formed by heating at 180° C. for 60 minutes on a hot plate.

(iii) Formation of Light-Emitting Layer

Polymer compound HP1 and phosphorescent compound MC1 (polymer compound HP1/phosphorescent compound MC1=70% by weight/30 by weight) were dissolved at a concentration of 1.5% by weight in xylene to prepare a xylene solution. A film was formed at a thickness of 70 nm on the hole-transporting layer by the spin coating 1.5 method using this xylene solution, and in a nitrogen gas atmosphere, a light-emitting layer was formed by heating at 130° C. for 10 minutes.

(iv) Formation of Electron-Transporting Layer

A film was formed at a thickness of 10 nm on the light-emitting layer by the spin coating method using a solution obtained by dissolving electron-transporting material HE1 at a concentration of 0.16% by weight and compound A-1 (dopant material) at a concentration of 0.04% by weight in methanol, and in a nitrogen gas atmosphere, an electron-transporting layer was formed by heating at 50° C. for 10 minutes.

(v) Formation of Cathode

The substrate with the electron-transporting layer formed was placed in a vapor deposition machine, and after pressure reduction to $1.0 \times 10^{-4}$ Pa or lower, silver (work function: 4.5 eV) as a cathode was deposited at 100 nm on the electron-transporting layer. After the deposition, the resultant was sealed using a glass substrate to thereby prepare light-emitting device D1.

(vi) Evaluation of Light-Emitting Device

EL emission mainly derived from phosphorescent compound MC1 was observed by applying voltage to the light-emitting device D1. The luminance at the time of application of 18 V was 9540 cd/m$^2$.

<Comparative Example 1> Preparation and Evaluation of Light-Emitting Device CD1

Light-emitting device CD1 was prepared in the same way as in Example 1 except that the compound A-1 was not contained in the electron-transporting layer. EL emission mainly derived from phosphorescent compound MC1 was observed by applying voltage to the light-emitting device CD1. The luminance exhibited by the light-emitting device CD1 at the time of application of 18 V was 1532 cd/m$^2$.

<Example 2> Preparation and Evaluation of Light-Emitting Device D2

Light-emitting device D2 was prepared in the same way as in Example 1 except that electron-transporting material HE2 was used instead of the electron-transporting material HE1. EL emission mainly derived from phosphorescent compound MC1 was observed by applying voltage to the light-emitting device D2. The luminance exhibited by the light-emitting device D2 at the time of application of 18 V was 13237 cd/m$^2$.

<Comparative Example 2> Preparation and Evaluation of Light-Emitting Device CD2

Light-emitting device CD2 was prepared in the same way as in Example 2 except that the compound A-1 was not contained in the electron-transporting layer. EL emission mainly derived from phosphorescent compound MC1 was observed by applying voltage to the light-emitting device CD2. The luminance exhibited by the light-emitting device CD2 at the time of application of 18 V was 301 cd/m$^2$.

<Example 3> Preparation and Evaluation of Light-Emitting Device D3

Light-emitting device D3 was prepared in the same way as in Example 1 except that electron-transporting material TAZ was used instead of the electron-transporting material HE1. EL emission mainly derived from phosphorescent compound MC1 was observed by applying voltage to the light-emitting device D3. The luminance exhibited by the light-emitting device D3 at the time of application of 18 V was 16102 cd/m$^2$.

<Comparative Example 3> Preparation and Evaluation of Light-Emitting Device CD3

Light-emitting device CD3 was prepared in the same way as in Example 3 except that the compound A-1 was not contained in the electron-transporting layer. EL emission mainly derived from phosphorescent compound MC1 was observed by applying voltage to the light-emitting device CD3. The luminance exhibited by the light-emitting device CD3 at the time of application of 18 V was 7877 cd/m$^2$.

<Example 4> Preparation and Evaluation of Light-Emitting Device D4

Light-emitting device D4 was prepared in the same way as in Example 1 except that the xylene solution used in the formation of the light-emitting layer was changed to a xylene solution prepared by dissolving polymer compound HP2 and phosphorescent compound MC2 (polymer compound HP2/phosphorescent compound MC2=64% by weight/36% by weight) at a concentration of 1.5% by weight in xylene. EL emission mainly derived from phosphorescent compound MC2 was observed by applying voltage to the light-emitting device D4. The luminance exhibited by the light-emitting device D4 at the time of application of 18 V was 548 cd/m².

<Comparative Example 4> Preparation and Evaluation of Light-Emitting Device CD4

Light-emitting device CD4 was prepared in the same way as in Example 4 except that the compound A-1 was not contained in the electron-transporting layer. EL emission mainly derived from phosphorescent compound MC2 was observed by applying voltage to the light-emitting device CD4. The luminance exhibited by the light-emitting device CD4 at the time of application of 18 V was 44 cd/m².

INDUSTRIAL APPLICABILITY

The light-emitting device according to the present invention employs a strong n-type doping material and emits light with a high luminance. Also, the light-emitting device according to the present invention can be easily produced using a coating method because the n-type doping material is relatively stable in a solvent.

The invention claimed is:

1. A light-emitting device comprising an anode, a light-emitting layer, an electron-transporting layer and a cathode,
the electron-transporting layer containing at least one electron-transporting material whose LUMO level is −3.0 eV or more and at least one dopant material selected from the group consisting of a heterocyclic compound whose SOMO level is −2.2 to −1.5 eV and a derivative thereof, wherein
the LUMO level of the electron-transporting material is smaller than the SOMO level of the heterocyclic compound, and
the derivative is one of a compound that is converted to the heterocyclic compound by activation by heat or light irradiation and a compound that is formed from the heterocyclic compound by electron donation to the electron-transporting material,
the heterocyclic compound is a compound represented by the formula (1-A), and
the derivative is a compound represented by the formula (1-B) or the formula (1-C):

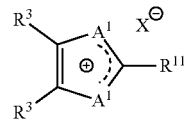
(1-A)

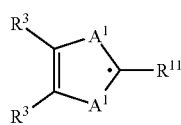
(1-B)

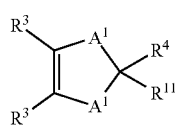
(1-C)

wherein
$A^1$ represents an oxygen atom, a sulfur atom, —$NR^5$— or —$PR^5$—; two $A^1$ are the same as or different from each other, and at least one $A^1$ is —$NR^5$— or —$PR^5$—;
$R^3$ represents a hydrogen atom, an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; —$CH_2$— in these groups is optionally substituted by an oxygen atom, a sulfur atom, —$NR^5$— or —C(=O)O—, and a portion or the whole of hydrogen atoms in these groups is optionally replaced with a halogen atom, provided that adjacent two —$CH_2$— are not substituted at the same time; two $R^3$ are the same or different and are optionally bonded to each other to form a ring, and a substituent is optionally bonded onto the ring;
$R^4$ represents a hydrogen atom, —$C(R^6)_3$, —$OR^7$, —$N(R^7)_2$ or —$Si(R^7)_3$; —$CH_2$— in these groups is optionally substituted by an oxygen atom, a sulfur atom, —$NR^5$— or —C(=O)O—, and a portion or the whole of hydrogen atoms in these groups is optionally replaced with a halogen atom, provided that adjacent two —$CH_2$— are not substituted at the same time;
$R^5$ represents an alkyl group, a cycloalkyl group, an aryl group or a monovalent heterocyclic group; —$CH_2$— in these groups is optionally substituted by an oxygen atom, a sulfur atom, —$NR^8$— or —C(=O)O—, and a portion or the whole of hydrogen atoms in these groups is optionally replaced with a halogen atom, provided that adjacent two —$CH_2$— are not substituted at the same time; when a plurality of $R^5$ are present, the plurality of $R^5$ are the same as or different from each other;
$R^6$ represents a hydrogen atom, an alkyl group, a cycloalkyl group, an aryl group or a monovalent heterocyclic group; a portion or the whole of hydrogen atoms in these groups is optionally replaced with a halogen atom; a plurality of $R^6$ are the same as or different from each other; two $R^6$ are optionally bonded to form a ring;
$R^7$ represents an alkyl group, a cycloalkyl group, an aryl group or a monovalent heterocyclic group; a portion or the whole of hydrogen atoms in these groups is optionally replaced with a halogen atom; a plurality of $R^7$ are the same as or different from each other; two $R^7$ are optionally bonded to form a ring;
$R^8$ represents an alkyl group, a cycloalkyl group, an aryl group or a monovalent heterocyclic group; a portion or the whole of hydrogen atoms in these groups is optionally replaced with a halogen atom; when a plurality of $R^8$ are present, the plurality of $R^8$ are the same as or different from each other;
$R^{11}$ represents an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group or a disubstituted amino group; —$CH_2$— in these groups is optionally substituted by an oxygen atom, a sulfur atom, —$NR^5$— or —C(=O)O—, and a portion or the whole of hydrogen atoms in these groups is optionally replaced with a halogen atom, provided that adjacent two —$CH_2$— are not substituted at the same time;

$X^-$ represents a counter anion for the cation; and wherein the electron-transporting material comprises a compound selected from the group consisting of:

(i) a polymer compound having a constitutional unit represented by the formula (ET-1):

$$\underset{}{-[Ar^{E1}]-} \quad (R^{E1})_{nE1} \qquad (ET\text{-}1)$$

wherein $nE1$ represents an integer of 1 or larger;

$Ar^{E1}$ represents an aromatic hydrocarbon group or a heterocyclic group, and these groups optionally have a substituent other than $R^{E1}$;

$R^{E1}$ represents an alkyl group, a cycloalkyl group, an aryl group, an alkoxy group, a cycloalkoxy group, an aryloxy group, a monovalent heterocyclic group, or a group represented by the formula: —$R^{E2}(-X^1)_{m1}$; when a plurality of $R^{E1}$ are present, the plurality of $R^{E1}$ are the same as or different from each other;

$X^1$ represents a monovalent group containing a heteroatom; when a plurality of $X^1$ are present, the plurality of $X^1$ are the same as or different from each other;

$R^{E2}$ represents a direct bond or an $(m1+1)$-valent group; and $m1$ represents an integer of 1 or larger; and (ii) a compound represented by the formula (H-1):

$$Ar^{H1}-\left[\{L^{H2}\}_{nH2}\{L^{H1}\}_{nH1}\{L^{H2}\}_{nH2}\right]_{nH3}-Ar^{H2} \qquad (H\text{-}1)$$

wherein $Ar^{H1}$, $Ar^{H2}$ and $L^{H1}$ each represent an aromatic hydrocarbon group or a heterocyclic group;

$L^{H2}$ represents a group represented by —N(-$L^{H21}$-$R^{H21}$)—;

$L^{H21}$ represents a single bond, an arylene group or a divalent heterocyclic group, and these groups optionally have a substituent;

$R^{H21}$ represents a hydrogen atom, an alkyl group, a cycloalkyl group, an aryl group or a monovalent heterocyclic group, and these groups optionally have a substituent;

when a plurality of $L^{H1}$ are present, the plurality of $L^{H1}$ are the same as or different from each other; when a plurality of $L^{H2}$ are present, the plurality of $L^{H2}$ are the same as or different from each other; and $n^{H1}$, $n^{H2}$ and $n^{H3}$ represent an integer of 0 or larger.

2. The light-emitting device according to claim 1, wherein the electron-transporting layer and the cathode are adjacent.

3. The light-emitting device according to claim 1, wherein a content of the dopant material in the electron-transporting layer is 1 to 50 parts by mass with respect to 100 parts by mass of the electron-transporting material.

4. The light-emitting device according to claim 1, wherein the light-emitting layer comprises a phosphorescent material.

5. The light-emitting device according to claim 1, wherein the heterocyclic compound is a compound represented by the formula (2-A), and the derivative is a compound represented by the formula (2-B) or the formula (2-C):

(2-A)

(2-B)

(2-C)

wherein $R^4$, $R^5$ and $X^-$ are the same as above;

$R^2$ represents an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; —$CH_2$— in these groups is optionally substituted by an oxygen atom, a sulfur atom, —$NR^5$— or —C(=O)O—, and a portion or the whole of hydrogen atoms in these groups is optionally replaced with a halogen atom, provided that adjacent two —$CH_2$— are not substituted at the same time; in the case where m is 2 or larger, a plurality of $R^2$ are the same as or different from each other; adjacent $R^2$ are optionally bonded to each other to form a ring;

$R^9$ represents an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; —$CH_2$— in these groups is optionally substituted by an oxygen atom, a sulfur atom, —$NR^5$— or —C(=O)O—, and a portion or the whole of hydrogen atoms in these groups is optionally replaced with a halogen atom, provided that adjacent two —$CH_2$— are not substituted at the same time; in the case where n is 2 or larger, a plurality of $R^9$ are the same as or different from each other; adjacent $R^9$ are optionally bonded to each other to form a ring;

m represents an integer of 0 to 5;

n represents an integer of 0 to 4; and $m+n$ is 2 or larger.

6. A method for producing an electron-transporting layer, comprising
a step of doping an electron-transporting material whose LUMO level is −3.0 eV or more with a heterocyclic compound whose SOMO level is −2.2 to −1.5 eV, wherein
the LUMO level of the electron-transporting material is smaller than the SOMO level of the heterocyclic compound,
the heterocyclic compound is a compound represented by the formula (1-A), and

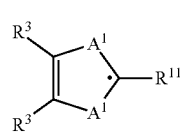

(1-A)

wherein
$A^1$ represents an oxygen atom, a sulfur atom, —$NR^5$— or —$PR^5$—; two $A^1$ are the same as or different from each other, and at least one $A^1$ is —$NR^5$— or —$PR^5$—;
$R^3$ represents a hydrogen atom, an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; —$CH_2$— in these groups is optionally substituted by an oxygen atom, a sulfur atom, —$NR^5$— or —C(=O)O—, and a portion or the whole of hydrogen atoms in these groups is optionally replaced with a halogen atom, provided that adjacent two —$CH_2$— are not substituted at the same time; two $R^3$ are the same or different and are optionally bonded to each other to form a ring, and a substituent is optionally bonded onto the ring;
$R^5$ represents an alkyl group, a cycloalkyl group, an aryl group or a monovalent heterocyclic group; —$CH_2$— in these groups is optionally substituted by an oxygen atom, a sulfur atom, —$NR^8$— or —C(=O)O—, and a portion or the whole of hydrogen atoms in these groups is optionally replaced with a halogen atom, provided that adjacent two —$CH_2$— are not substituted at the same time; when a plurality of $R^5$ are present, the plurality of $R^5$ are the same as or different from each other;
$R^8$ represents an alkyl group, a cycloalkyl group, an aryl group or a monovalent heterocyclic group; a portion or the whole of hydrogen atoms in these groups is optionally replaced with a halogen atom; when a plurality of $R^8$ are present, the plurality of $R^8$ are the same as or different from each other; and
$R^{11}$ represents an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group or a disubstituted amino group; —$CH_2$— in these groups is optionally substituted by an oxygen atom, a sulfur atom, —$NR^5$— or —C(=O)O—, and a portion or the whole of hydrogen atoms in these groups is optionally replaced with a halogen atom, provided that adjacent two —$CH_2$— are not substituted at the same time; and
wherein the electron-transporting material comprises a compound selected from the group consisting of:

(i) a polymer compound having a constitutional unit represented by the formula (ET-1):

(ET-1)

wherein
nE1 represents an integer of 1 or larger;
$Ar^{E1}$ represents an aromatic hydrocarbon group or a heterocyclic group, and these groups optionally have a substituent other than $R^{E1}$;
$R^{E1}$ represents an alkyl group, a cycloalkyl group, an aryl group, an alkoxy group, a cycloalkoxy group, an aryloxy group, a monovalent heterocyclic group, or a group represented by the formula: —$R^{E2}$(—$X^1$)$_{m1}$; when a plurality of $R^{E1}$ are present, the plurality of $R^{E1}$ are the same as or different from each other;
$X^1$ represents a monovalent group containing a heteroatom; when a plurality of $X^1$ are present, the plurality of $X^1$ are the same as or different from each other;
$R^{E2}$ represents a direct bond or an (m1+1)-valent group; and
m1 represents an integer of 1 or larger; and (ii) a compound represented by the formula (H-1):

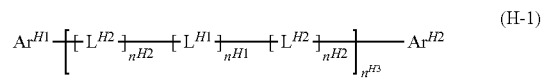

(H-1)

wherein
$Ar^{H1}$, $Ar^{H2}$ and $L^{H1}$ each represent an aromatic hydrocarbon group or a heterocyclic group;
$L^{H2}$ represents a group represented by —N(-$L^{H21}$-$R^{H21}$)—;
$L^{H21}$ represents a single bond, an arylene group or a divalent heterocyclic group, and these groups optionally have a substituent;
$R^{H21}$ represents a hydrogen atom, an alkyl group, a cycloalkyl group, an aryl group or a monovalent heterocyclic group, and these groups optionally have a substituent;
when a plurality of $L^{H1}$ are present, the plurality of $L^{H1}$ are the same as or different from each other; when a plurality of $L^{H2}$ are present, the plurality of $L^{H2}$ are the same as or different from each other; and
$n^{H1}$, $n^{H2}$ and $n^{H3}$ represent an integer of 0 or larger.

7. A method for producing a light-emitting device having an anode, a light-emitting layer, an electron-transporting layer and a cathode, comprising:
a step of providing a composition containing at least one electron-transporting material whose LUMO level is −3.0 eV or more and at least one dopant material selected from the group consisting of a heterocyclic compound whose SOMO level is −2.2 to −1.5 eV and a derivative thereof; and
a step of forming a film of the composition by a coating method to form the electron-transporting layer, wherein the LUMO level of the electron-transporting material is smaller than the SOMO level of the heterocyclic compound, wherein the derivative is one of a compound that is converted to the heterocyclic compound by activation by heat or light irradiation and a compound that is formed from the heterocyclic compound by electron donation to the electron-transporting material,
the heterocyclic compound is a compound represented by the formula (1-A), and
the derivative is a compound represented by the formula (1-B) or the formula (1-C):

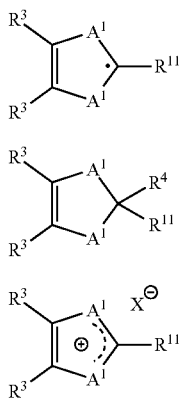

wherein
$A^1$ represents an oxygen atom, a sulfur atom, —$NR^5$— or —$PR^5$—; two $A^1$ are the same as or different from each other, and at least one $A^1$ is —$NR^5$— or —$PR^5$—;
$R^3$ represents a hydrogen atom, an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group, a halogen atom or a disubstituted amino group; —$CH_2$— in these groups is optionally substituted by an oxygen atom, a sulfur atom, —$NR^5$— or —$C(=O)O$—, and a portion or the whole of hydrogen atoms in these groups is optionally replaced with a halogen atom, provided that adjacent two —$CH_2$— are not substituted at the same time; two $R^3$ are the same or different and are optionally bonded to each other to form a ring, and a substituent is optionally bonded onto the ring;
$R^4$ represents a hydrogen atom, —$C(R^6)_3$, —$OR^7$, —$N(R^7)_2$ or —$Si(R^7)_3$; —$CH_2$— in these groups is optionally substituted by an oxygen atom, a sulfur atom, —$NR^5$— or —$C(=O)O$—, and a portion or the whole of hydrogen atoms in these groups is optionally replaced with a halogen atom, provided that adjacent two —$CH_2$— are not substituted at the same time;
$R^5$ represents an alkyl group, a cycloalkyl group, an aryl group or a monovalent heterocyclic group; —$CH_2$— in these groups is optionally substituted by an oxygen atom, a sulfur atom, —$NR^8$— or —$C(=O)O$—, and a portion or the whole of hydrogen atoms in these groups is optionally replaced with a halogen atom, provided that adjacent two —$CH_2$— are not substituted at the same time; when a plurality of $R^5$ are present, the plurality of $R^5$ are the same as or different from each other;
$R^6$ represents a hydrogen atom, an alkyl group, a cycloalkyl group, an aryl group or a monovalent heterocyclic group; a portion or the whole of hydrogen atoms in these groups is optionally replaced with a halogen atom; a plurality of $R^6$ are the same as or different from each other; two $R^6$ are optionally bonded to form a ring;
$R^7$ represents an alkyl group, a cycloalkyl group, an aryl group or a monovalent heterocyclic group; a portion or the whole of hydrogen atoms in these groups is optionally replaced with a halogen atom; a plurality of $R^7$ are the same as or different from each other; two $R^7$ are optionally bonded to form a ring;
$R^8$ represents an alkyl group, a cycloalkyl group, an aryl group or a monovalent heterocyclic group; a portion or the whole of hydrogen atoms in these groups is optionally replaced with a halogen atom; when a plurality of $R^8$ are present, the plurality of $R^8$ are the same as or different from each other;
$R^{11}$ represents an alkyl group, a cycloalkyl group, an aryl group, an alkoxy group, a cycloalkoxy group, an aryloxy group, an alkylsulfenyl group, a cycloalkylsulfenyl group, an arylsulfenyl group, a monovalent heterocyclic group or a disubstituted amino group; —$CH_2$— in these groups is optionally substituted by an oxygen atom, a sulfur atom, —$NR^5$— or —$C(=O)O$—, and a portion or the whole of hydrogen atoms in these groups is optionally replaced with a halogen atom, provided that adjacent two —$CH_2$— are not substituted at the same time; and
$X^-$ represents a counter anion for the cation; and
wherein the electron-transporting material comprises a compound selected from the group consisting of:
(i) a polymer compound having a constitutional unit represented by the formula (ET-1):

wherein
nE1 represents an integer of 1 or larger;
$Ar^{E1}$ represents an aromatic hydrocarbon group or a heterocyclic group, and these groups optionally have a substituent other than $R^{E1}$;
$R^{E1}$ represents an alkyl group, a cycloalkyl group, an aryl group, an alkoxy group, a cycloalkoxy group, an aryloxy group, a monovalent heterocyclic group, or a group represented by the formula: —$R^{E2}(-X^1)_{m1}$; when a plurality of $R^{E1}$ are present, the plurality of $R^{E1}$ are the same as or different from each other;
$X^1$ represents a monovalent group containing a heteroatom; when a plurality of $X^1$ are present, the plurality of $X^1$ are the same as or different from each other;
$R^{E2}$ represents a direct bond or an (m1+1)-valent group; and
m1 represents an integer of 1 or larger; and
(ii) a compound represented by the formula (H-1):

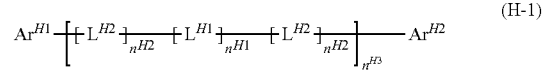

wherein
$Ar^{H1}$, $Ar^{H2}$ and $L^{H1}$ each represent an aromatic hydrocarbon group or a heterocyclic group;
$L^{H2}$ represents a group represented by $-N(-L^{H21}-R^{H21})-$;
$L^{H21}$ represents a single bond, an arylene group or a divalent heterocyclic group, and these groups optionally have a substituent;
$R^{H21}$ represents a hydrogen atom, an alkyl group, a cycloalkyl group, an aryl group or a monovalent heterocyclic group, and these groups optionally have a substituent;
when a plurality of $L^{H1}$ are present, the plurality of $L^{H1}$ are the same as or different from each other; when a plurality of $L^{H2}$ are present, the plurality of $L^{H2}$ are the same as or different from each other; and
$n^{H1}$, $n^{H2}$ and $n^{H3}$ represent an integer of 0 or larger.

\* \* \* \* \*